(12) United States Patent
Battrell et al.

(10) Patent No.: US 8,222,023 B2
(45) Date of Patent: *Jul. 17, 2012

(54) INTEGRATED NUCLEIC ACID ASSAYS

(75) Inventors: C. Frederick Battrell, Redmond, WA (US); John Gerdes, Columbine Valley, CO (US); John R. Williford, Sammamish, WA (US); Denise Maxine Hoekstra, Monroe, WA (US); Wayne L. Breidford, Seattle, WA (US); Stephen Mordue, Kirkland, WA (US); John Clemmens, Redmond, WA (US); Melud Nabavi, Seattle, WA (US); Mark Kokoris, Bothell, WA (US)

(73) Assignee: Micronics, Inc., Redmond, WA (US)

( * ) Notice: Subject to any disclaimer, the term of this patent is extended or adjusted under 35 U.S.C. 154(b) by 330 days.

This patent is subject to a terminal disclaimer.

(21) Appl. No.: 12/207,627

(22) Filed: Sep. 10, 2008

(65) Prior Publication Data

US 2009/0148933 A1 Jun. 11, 2009

Related U.S. Application Data

(63) Continuation of application No. PCT/US2007/006584, filed on Mar. 15, 2007.

(60) Provisional application No. 60/782,649, filed on Mar. 15, 2006, provisional application No. 60/844,811, filed on Sep. 14, 2006.

(51) Int. Cl.
*C12M 1/34* (2006.01)
(52) U.S. Cl. ................ 435/287.2; 435/288.5; 435/286.5
(58) Field of Classification Search .... 435/287.1–287.3, 435/287.6, 288.4, 288.5, 288.7
See application file for complete search history.

(56) References Cited

U.S. PATENT DOCUMENTS

| | | | |
|---|---|---|---|
| 4,610,678 A | 9/1986 | Weisman et al. | 604/368 |
| 4,683,195 A | 7/1987 | Mullis et al. | 435/6 |
| 4,683,202 A | 7/1987 | Mullis | 435/91 |
| 4,800,159 A | 1/1989 | Mullis et al. | 435/172.3 |
| 4,855,240 A | 8/1989 | Rosenstein et al. | 436/514 |
| 4,883,750 A | 11/1989 | Whiteley et al. | 435/6 |
| 4,943,522 A | 7/1990 | Eisinger et al. | 435/7 |
| 4,956,302 A | 9/1990 | Gordon et al. | 436/161 |
| 4,965,188 A | 10/1990 | Mullis et al. | 435/6 |
| 5,038,852 A | 8/1991 | Johnson et al. | 165/12 |

(Continued)

FOREIGN PATENT DOCUMENTS

EP    2 202 328 A    9/1988

(Continued)

OTHER PUBLICATIONS

Arar, S., et al., "Synthesis and Antiviral Activity of Peptide—Oligonucleotide Conjugates Prepared by Using Nα-(Bromoacetyl)peptides," *Bioconjugate Chem.*, 6(5): 573-577, 1995.

(Continued)

*Primary Examiner* — William H Beisner
(74) *Attorney, Agent, or Firm* — Seed IP Law Group PLLC

(57) ABSTRACT

Integrated microfluidic cartridges for nucleic acid extraction, amplification, and detection from clinical samples are disclosed. The devices are single-entry, sanitary, and disposable. The devices enable simplex or multiplex nucleic acid target detection, as for example: assay panels for multiple infectious agents, or assay panels for cancerous cell types. Methods for use of microfluidic cartridges in a fully automated, pneumatically controlled apparatus are also disclosed.

9 Claims, 28 Drawing Sheets

U.S. PATENT DOCUMENTS

| | | | |
|---|---|---|---|
| 5,075,078 A | 12/1991 | Osikowicz et al. | 422/56 |
| 5,120,643 A | 6/1992 | Ching et al. | 435/7.92 |
| 5,130,238 A | 7/1992 | Malek et al. | 435/91 |
| 5,234,809 A | 8/1993 | Boom et al. | 435/91 |
| 5,270,183 A | 12/1993 | Corbett et al. | 435/91.2 |
| 5,275,785 A | 1/1994 | May et al. | 422/56 |
| 5,304,487 A | 4/1994 | Wilding et al. | 435/291 |
| 5,354,668 A | 10/1994 | Auerbach | 435/91.1 |
| 5,427,930 A | 6/1995 | Birkenmeyer et al. | 435/91.52 |
| 5,455,166 A | 10/1995 | Walker | 435/91.2 |
| 5,498,392 A | 3/1996 | Wilding et al. | 422/68.1 |
| 5,504,013 A | 4/1996 | Senior | 436/165 |
| 5,582,989 A | 12/1996 | Caskey et al. | 435/6 |
| 5,587,128 A | 12/1996 | Wilding et al. | 422/50 |
| 5,591,645 A | 1/1997 | Rosenstein | 436/514 |
| 5,602,040 A | 2/1997 | May et al. | 436/514 |
| 5,622,871 A | 4/1997 | May et al. | 436/514 |
| 5,635,602 A | 6/1997 | Cantor et al. | 530/391.1 |
| 5,656,503 A | 8/1997 | May et al. | 436/514 |
| 5,660,990 A | 8/1997 | Rao et al. | 435/6 |
| 5,707,807 A | 1/1998 | Kato | 435/6 |
| 5,716,842 A | 2/1998 | Baier et al. | 435/283.1 |
| 5,716,852 A | 2/1998 | Yager et al. | 436/172 |
| 5,724,404 A | 3/1998 | Garcia et al. | 379/34 |
| 5,726,751 A | 3/1998 | Altendorf et al. | 356/246 |
| 5,747,349 A | 5/1998 | van den Engh et al. | 436/172 |
| 5,748,827 A | 5/1998 | Holl et al. | 385/134 |
| 5,770,460 A | 6/1998 | Pawlak et al. | 436/510 |
| 5,798,273 A | 8/1998 | Shuler et al. | 436/514 |
| 5,863,801 A * | 1/1999 | Southgate et al. | 436/63 |
| 5,906,602 A | 5/1999 | Weber et al. | 604/385.1 |
| 5,922,210 A | 7/1999 | Brody et al. | 210/767 |
| 5,932,100 A | 8/1999 | Yager et al. | 210/634 |
| 5,948,684 A | 9/1999 | Weigl et al. | 436/52 |
| 5,955,029 A | 9/1999 | Wilding et al. | 422/68.1 |
| 5,965,410 A | 10/1999 | Chow et al. | 435/91.2 |
| 5,971,158 A | 10/1999 | Yager et al. | 209/155 |
| 5,971,355 A | 10/1999 | Biegelsen et al. | 251/129.06 |
| 5,972,710 A | 10/1999 | Weigl et al. | 436/34 |
| 5,972,721 A | 10/1999 | Bruno et al. | 436/526 |
| 5,974,867 A | 11/1999 | Forster et al. | 73/61.41 |
| 5,989,813 A | 11/1999 | Gerdes | 435/6 |
| 6,007,775 A | 12/1999 | Yager | 422/57 |
| 6,018,616 A | 1/2000 | Schaper | 392/418 |
| 6,020,187 A | 2/2000 | Tam | 435/287.2 |
| 6,057,167 A | 5/2000 | Shieh et al. | 436/526 |
| 6,171,865 B1 | 1/2001 | Weigl et al. | 436/52 |
| 6,210,882 B1 | 4/2001 | Landers et al. | 435/6 |
| 6,368,876 B1 | 4/2002 | Huang et al. | 436/517 |
| 6,387,290 B1 | 5/2002 | Brody et al. | 216/99 |
| 6,399,398 B1 | 6/2002 | Cunningham et al. | 436/534 |
| 6,418,968 B1 | 7/2002 | Pezzuto et al. | 137/833 |
| 6,431,212 B1 | 8/2002 | Hayenga et al. | 137/855 |
| 6,488,896 B2 | 12/2002 | Weigl et al. | 422/101 |
| 6,541,274 B2 | 4/2003 | Nagle et al. | 436/180 |
| 6,562,209 B1 | 5/2003 | Sullivan et al. | 204/403.01 |
| 6,581,899 B2 | 6/2003 | Williams | 251/7 |
| 6,620,273 B2 | 9/2003 | Dai et al. | 156/89.11 |
| 6,632,655 B1 | 10/2003 | Mehta et al. | 435/288.5 |
| 6,720,411 B2 | 4/2004 | Mirkin et al. | 536/23.1 |
| 6,743,399 B1 | 6/2004 | Weigl et al. | 422/102 |
| 6,748,975 B2 | 6/2004 | Hartshorne et al. | 137/625.46 |
| 6,767,194 B2 | 7/2004 | Jeon et al. | 417/559 |
| 6,787,338 B2 | 9/2004 | Wittwer et al. | 435/91.2 |
| 6,815,160 B1 | 11/2004 | Chien et al. | 435/5 |
| 6,901,949 B2 | 6/2005 | Cox et al. | 137/334 |
| 6,953,675 B2 | 10/2005 | Leung et al. | 435/69.6 |
| 6,953,676 B1 | 10/2005 | Wilding et al. | 435/91.2 |
| 6,955,738 B2 | 10/2005 | Derand et al. | 156/272.6 |
| 6,974,119 B2 | 12/2005 | Brendle et al. | 251/129.11 |
| 6,974,669 B2 | 12/2005 | Mirkin et al. | 435/6 |
| 7,087,414 B2 | 8/2006 | Gerdes et al. | 435/91.1 |
| 7,141,416 B2 * | 11/2006 | Krutzik | 435/288.5 |
| 7,153,673 B2 | 12/2006 | Stern | 435/91.2 |
| 2001/0046701 A1 | 11/2001 | Schulte et al. | 435/287.2 |
| 2002/0086443 A1 | 7/2002 | Bamdad | 436/526 |
| 2002/0160518 A1 | 10/2002 | Hayenga et al. | 436/70 |
| 2002/0192676 A1 | 12/2002 | Madonna et al. | 435/6 |
| 2002/0195152 A1 | 12/2002 | Fernandes et al. | 137/803 |
| 2003/0008308 A1 | 1/2003 | Enzelberger et al. | 435/6 |
| 2003/0032028 A1 | 2/2003 | Dace et al. | 435/6 |
| 2003/0124619 A1 | 7/2003 | Weigl et al. | 435/7.1 |
| 2003/0152927 A1 * | 8/2003 | Jakobsen et al. | 435/6 |
| 2003/0175990 A1 | 9/2003 | Hayenga et al. | 436/180 |
| 2003/0215825 A1 | 11/2003 | Tong | 435/6 |
| 2004/0005718 A1 | 1/2004 | Fukushima | 436/174 |
| 2004/0018611 A1 | 1/2004 | Ward et al. | 435/287.2 |
| 2004/0081997 A1 | 4/2004 | Stern | 435/6 |
| 2004/0121364 A1 | 6/2004 | Chee et al. | 435/6 |
| 2004/0226348 A1 | 11/2004 | Bruce, III et al. | 73/53.01 |
| 2005/0013732 A1 * | 1/2005 | Battrell et al. | 435/6 |
| 2005/0019792 A1 | 1/2005 | McBride et al. | 435/6 |
| 2005/0037397 A1 | 2/2005 | Mirkin et al. | 435/6 |
| 2005/0106066 A1 | 5/2005 | Saltsman et al. | 422/57 |
| 2005/0129582 A1 | 6/2005 | Breidford et al. | 422/100 |
| 2005/0142582 A1 | 6/2005 | Doyle et al. | 435/6 |
| 2005/0186585 A1 * | 8/2005 | Juncosa et al. | 435/6 |
| 2005/0205816 A1 | 9/2005 | Hayenga et al. | 251/61.1 |
| 2005/0221281 A1 * | 10/2005 | Ho | 435/4 |
| 2005/0284817 A1 | 12/2005 | Fernandez et al. | 210/695 |
| 2006/0073484 A1 | 4/2006 | Mathies et al. | 435/6 |
| 2006/0166375 A1 | 7/2006 | Hawkins et al. | 436/524 |
| 2006/0178568 A1 | 8/2006 | Danna et al. | 600/300 |
| 2006/0263816 A1 | 11/2006 | Laikhter et al. | 435/6 |
| 2006/0292588 A1 | 12/2006 | Chou et al. | 435/6 |
| 2006/0292630 A1 | 12/2006 | Fukumoto | 435/7.1 |
| 2007/0042427 A1 | 2/2007 | Gerdes et al. | 435/7.1 |
| 2007/0183935 A1 | 8/2007 | Clemmens et al. | 422/100 |
| 2007/0219366 A1 | 9/2007 | Gumbrecht et al. | 536/25.4 |
| 2007/0292858 A1 * | 12/2007 | Chen et al. | 435/6 |
| 2008/0226500 A1 | 9/2008 | Shikida et al. | 422/68.1 |
| 2009/0061450 A1 | 3/2009 | Hunter | 435/6 |
| 2009/0148847 A1 | 6/2009 | Kokoris et al. | 435/6 |
| 2009/0181411 A1 * | 7/2009 | Battrell et al. | 435/7.92 |

FOREIGN PATENT DOCUMENTS

| | | |
|---|---|---|
| EP | 0 320 308 A2 | 6/1989 |
| EP | 0 329 822 A1 | 8/1989 |
| EP | 1 659 405 A1 | 5/2006 |
| EP | 1 707 965 A1 | 10/2006 |
| WO | 88/10315 A1 | 12/1988 |
| WO | 89/06700 A1 | 7/1989 |
| WO | 89/09284 A1 | 10/1989 |
| WO | WO 02/12896 A1 | 2/2002 |
| WO | WO 02/16904 A2 | 2/2002 |
| WO | WO 03/031977 A2 | 4/2003 |
| WO | WO 03/054523 A2 | 7/2003 |
| WO | WO 03/102546 A2 | 12/2003 |
| WO | WO 2005/022154 A1 | 3/2005 |
| WO | WO 2005/069015 A1 | 7/2005 |
| WO | 2005/106024 A1 | 11/2005 |
| WO | WO 2006/018811 A1 | 2/2006 |
| WO | WO 2006/052652 A2 | 5/2006 |
| WO | WO 2007/106579 A2 | 9/2007 |
| WO | WO 2007/106580 A2 | 9/2007 |
| WO | WO 2007/109584 A1 | 9/2007 |

OTHER PUBLICATIONS

Ausubel et al., "Current Protocols in Molecular Biology," John Wiley and Sons, Baltimore, Md., 1989.

Bongartz, J., et al., "Improved biological activity of antisense oligonucleotides conjugated to a fusogenic peptide," *Nucleic Acids Research*, 22(22): 4681-4688, 1994.

Chan, C.-M., et al., "Polymer surface modification by plasmas and photons," *Surface Science Reports* 24:1-54, 1996.

Chou Q., et al, "Prevention of pre-PCR mis-priming and primer dimerization improves low-copy-number amplifications," *Nucleic Acids Research* 20(7):1717-1723, 1992.

D'Aquila, R., et al., "Maximizing sensitivity and specificity of PCR by pre-amplification heating," *Nucleic Acids Research*, 19(13):3749, 1991.

Dean, F.B., et al., "Comprehensive human genome amplification using multiple displacement amplification," *PNAS* 99(8):5261-5266, Apr. 16, 2002.

Detter, J.C., et al., "Isothermal Strand-Displacement Amplification Applications for High-Throughput Genomics," *Genomics* 80(6):691-698, Dec. 2002.

Eritja, R. et al., "Synthesis of Defined Peptide-Oligonucleotide Hybrids Containing a Nuclear Transport Signal Sequence," *Tetrahedron* 47(24):4113-4120, 1991.

Frohman, M.A. "PCR Protocols: A Guide to Methods and Applications," Academic Press, N.Y., 1990.

Garbassi et al., *Polymer Surfaces-From Physics to Technology*, John Wiley and Sons, Baltimore, Md., 1998, pp. 238-241.

Grover, W. H. et al., "Monolithic membrane valves and diaphragm pumps for practical large-scale integration into glass microfluidic devices," *Sensors and Actuators B* 89:315-323, 2003.

Harrison, J.G. et al., "Synthesis and hybridization analysis of a small library of peptide—oligonucleotide conjugates," *Nucleic Acids Research* 26(13):3136-3145, 1998.

Innis et al., *PCR Protocols*, Academic Press, Inc., San Diego, Calif., 1990.

Kellogg, D.E., et al, "TaqStart Antibody™: "Hot Start" PCR Facilitated by a Neutralizing Monoclonal Antibody Directed Against Taq DNA Polymerase," *BioTechniques* 16(6):1134-1137, 1994.

Kwoh, D.Y., et al., "Transcription-based amplification system and detection of amplified human immunodeficiency virus type 1 with a bead-based sandwich hybridization format," *Proc. Natl. Acad. Sci. U.S.A.* 86: 1173-1177, Feb. 1989.

Lage, J.M., et al., "Whole Genome Analysis of Genetic Alterations in Small DNA Samples Using Hyperbranched Strand Displacement Amplification and Array-CGH," *Genome Research* 13:294-307, 2003.

Notomi, T., et al. "Loop-mediated isothermal amplification of DNA," *Nucleic Acids Research* 28(12): e63, i-vii, 2000.

Ohara, O., et al., "One-sided polymerase chain reaction: The amplification of cDNA," *Proc. Natl. Acad. Sci. U.S.A.* 86:5673-5677, Aug. 1989.

Pfyffer, G.E., et al., "Diagnostic Performance of Amplified *Mycobacterium tuberculosis* Direct Test with Cerebrospinal Fluid, Other Nonrespiratory, and Respiratory Specimens," *Journal of Clinical Microbiology* 34(4): 834-841, Apr. 1996.

Schachter, J., et al. "Ligase Chain Reaction to Detect *Chlamydia trachomatis* Infection of the Cervix," *J. Clin. Microbiol.* 32(10):2540-2543, Oct. 1994.

Soukchareun, S., et al., "Use of $N^\alpha$-Fmoc-cysteine(S-thiobutyl) Derivatized Oligodeoxynucleotides for the Preparation of Oligodeoxynucleotide—Peptide Hybrid Molecules," *Bioconjugate Chem.* 9:466-475, 1998.

Stetsenko, D.A., et al., "Efficient Conjugation of Peptides to Oligonucleotides by "Native Ligation"," *J. Org. Chem.* 65: 4900-4908, 2000.

Tung, C.-H., et al., "Preparation and Applications of Peptide—Oligonucleotide Conjugates," *Bioconjugate Chem.* 11(5): 605-618, Sep./Oct. 2000.

Tung, C.-H., et al., "Preparation of Oligonucleotide-Peptide Conjugates," *Bioconjugate Chem.* 2:464-465, 1991.

Unger, M.A., et al., "Monolithic Microfabricated Valves and Pumps by Multilayer Soft Lithography," *Science* 288:113-116, Apr. 7, 2000.

van Gemen, B., et al., "Quantification of HIV-1 RNA in plasma using NASBA™ during HIV-1 primary infection," *Journal of Virological Methods* 43:177-188, 1993.

Vivès, E., et al., "Selective Coupling of a Highly Basic Peptide to an Oligonucleotide," *Tetrahedron Letters* 38(7): 1183-1186, 1997.

Walker, G. T., "Empirical Aspects of Strand Displacement Amplification," *PCR Methods and Applications* 3:1-6, 1993.

Walker, G.T., et al., "Strand displacement amplification—an isothermal, in vitro DNA amplification technique," *Nucleic Acids Research* 20(7):1691-1696, 1992.

Wu, D. Y., et al., "The Ligation Amplification Reaction (LAR)—Amplification of Specific DNA Sequences Using Sequential Rounds of Template-Dependent Ligation," *Genomics* 4:560-569, 1989.

Edelstein, R. L., et al., "The BARC biosensor applied to the detection of biological warfare agents," *Biosensors & Bioelectronics* 14:805-813, 2000.

Gijs, M. A. M., "Magnetic bead handling on-chip: new opportunities for analytical applications," *Microfluid Nanofluid* 1:22-40, 2004.

Graham, D. L., et al., "Magnetoresistive-based biosensors and biochips," *TRENDS in Biotechnology* 22(9):455-462, Sep. 2004.

Joung, J., et al., "Micropumps Based on Alternating High-Gradient Magnetic Fields," *IEEE Transactions on Magnetics* 36(4):2012-2014, Jul. 2000.

Kanehisa, M., "Use of statistical criteria for screening potential homologies in nucleic acid sequences," *Nucleic Acids Research* 12(1):203-213, 1984.

Lee, G. U., et al., "Implementation of Force Differentiation in the Immunoassay," *Analytical Biochemistry* 287:261-271, 2000.

Luxton, R., et al., "Use of External Magnetic Fields to Reduce Reaction Times in an Immunoassay Using Micrometer-Sized Paramagnetic Particles as Labels (Magnetoimmunoassay)," *Anal. Chem.* 76(6):1715-1719, Mar. 15, 2004.

Østergaard, S., et al., "A novel approach to the automation of clinical chemistry by controlled manipulation of magnetic particles," *Journal of Magnetism and Magnetic Materials* 194:156-162, 1999.

PCT International Preliminary Report on Patentability for PCT/US2007/006584, dated Sep. 16, 2008 (9 pages).

PCT International Search Report and Written Opinion of the International Searching Authority for PCT/US2007/006584, mailed Jan. 18, 2008 (14 pages).

PCT International Preliminary Report on Patentability for PCT/US2007/006585, dated Sep. 16, 2008 (12 pages).

PCT International Search Report and Written Opinion of the International Searching Authority for PCT/US2007/006585, mailed Jan. 3, 2008 (17 pages).

Rida, A., et al., "Long-range transport of magnetic microbeads using simple planar coils placed in a uniform magnetostatic field," *Applied Physics Letters* 83(12):2396-2398, Sep. 22, 2003.

Staben, M. E., et al., "Particle transport in Poiseuille flow in narrow channels," *International Journal of Multiphase Flow* 31:529-547, 2005.

TechNote 303, "Lateral Flow Tests," Bangs Laboratories, Inc., Rev. #002, Apr. 11, 2008, pp. 1-7.

* cited by examiner

Valve "OPEN"

Valve "CLOSED"

IN-LINE FILTER ELEMENT FOR PNEUMATIC MANIFOLD

Fig. 11
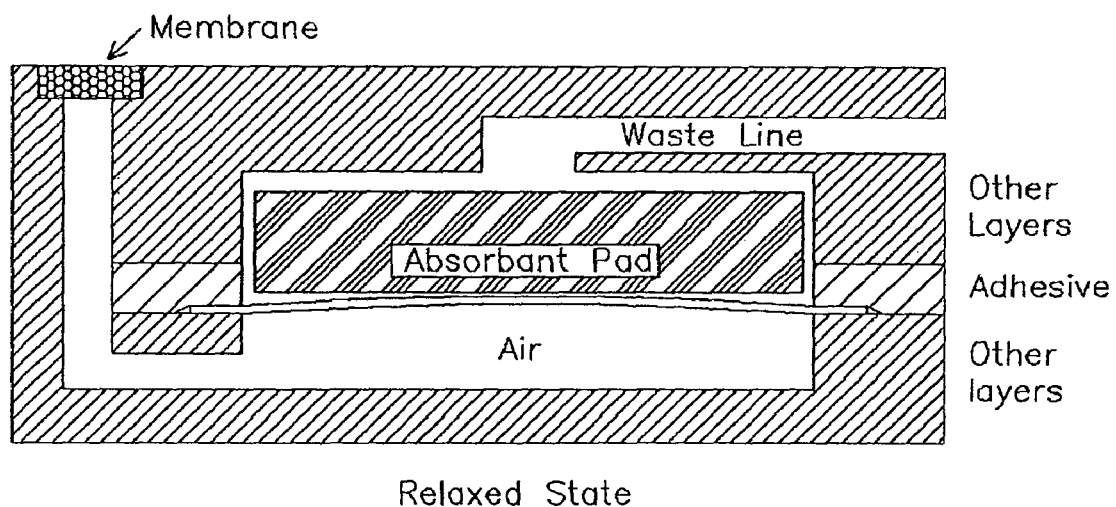
Relaxed State
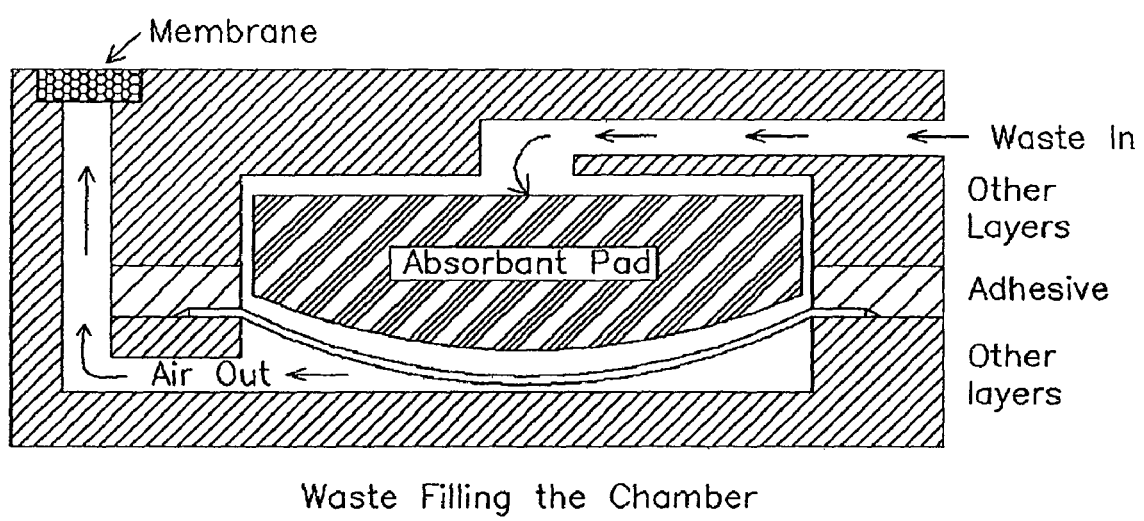
Waste Filling the Chamber

Fig. 12A
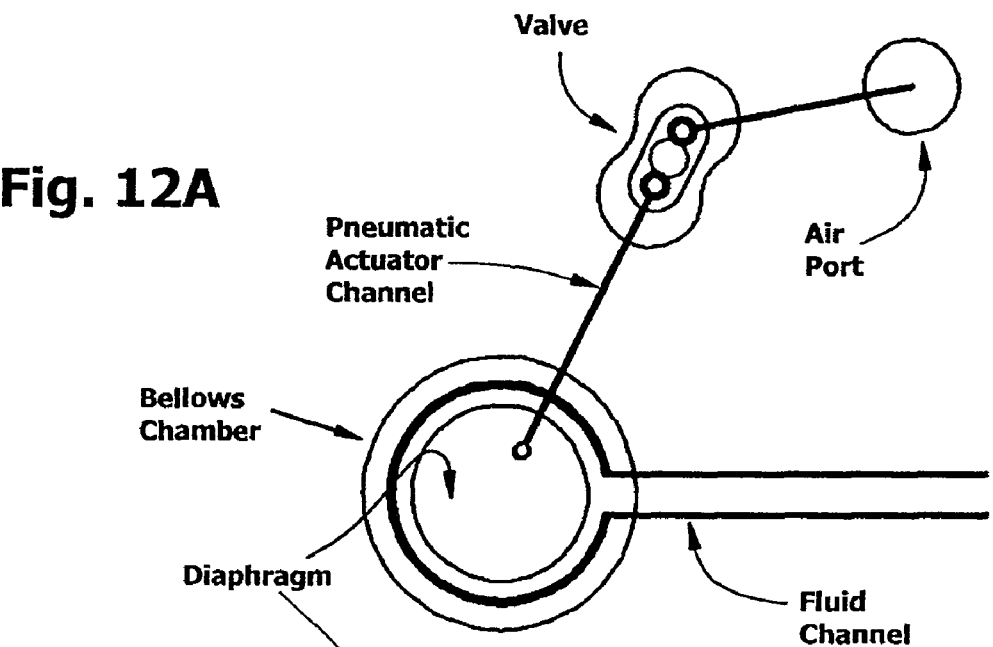
Fig. 12B
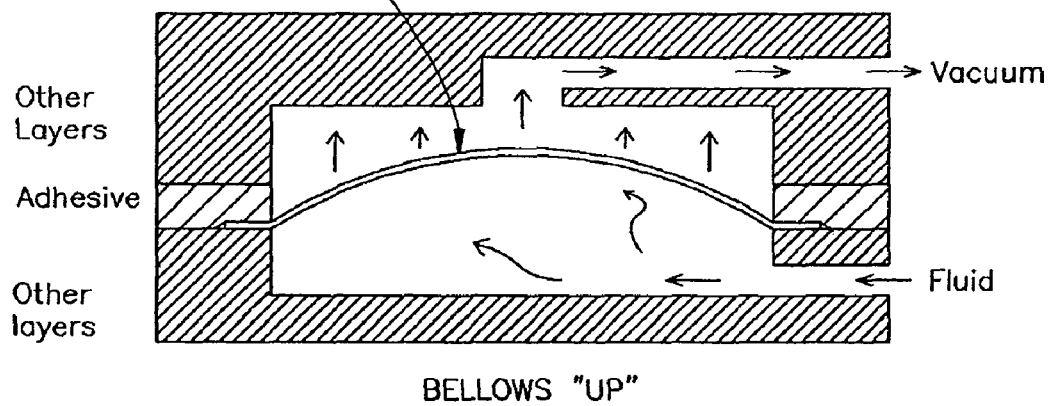
BELLOWS "UP"
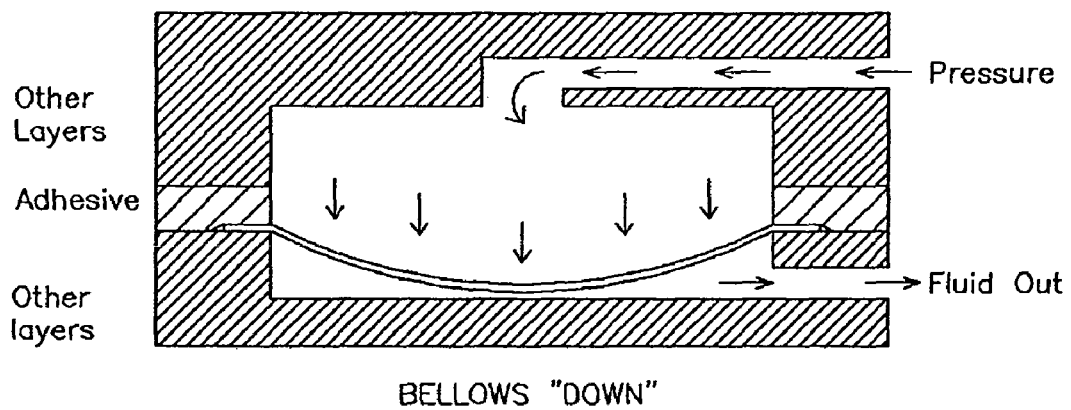
BELLOWS "DOWN"

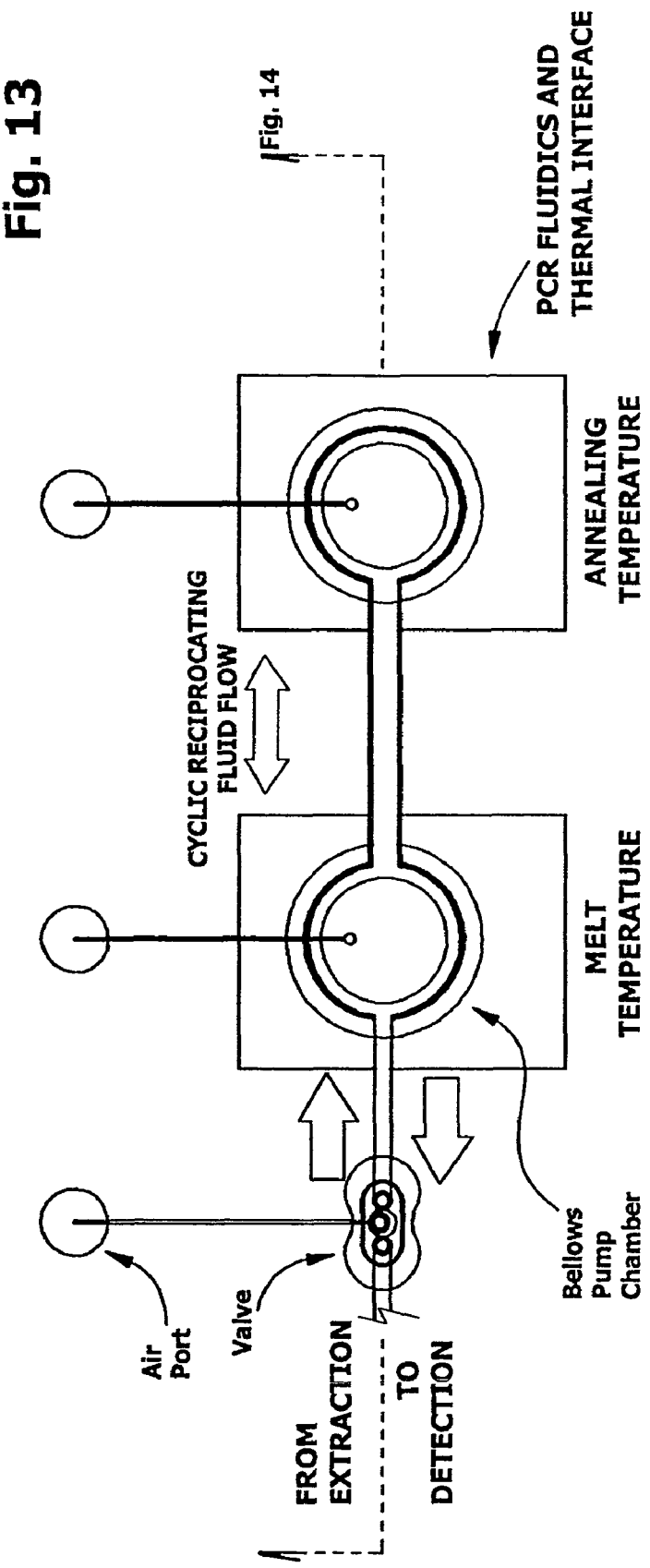

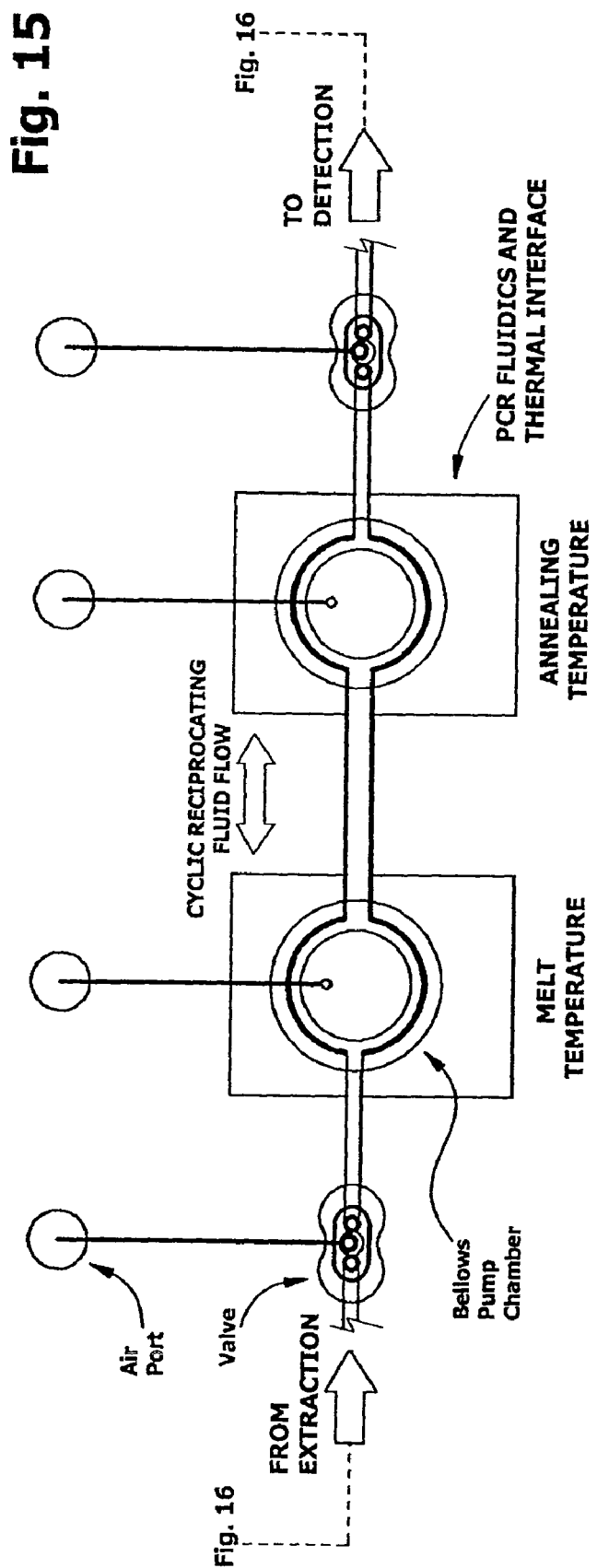

TRIPLE BELLOWS CHAMBER PCR FLUIDICS AND THERMAL INTERFACE

Laminated Overlay

Laminated Substrate

Laminated Overlay

Laminated Substrate

Microfluidic Channel

Mag Bead Reservoir

Amplification Chamber

Fig. 28

Symbols Used in the Figures

| Symbol | Description | Symbol | Description |
|---|---|---|---|
| ═══ | Microfluidic flow channel | ⊶ | Air port of pneumatic manifold |
| ⊕↗ | Process flow with valve | ⊶⊢ | Air port of pneumatic manifold with hydrophobic isolation filter |
| ⊗ | Hydraulic valve | | Sanitary vent with trap and hydrophobic isolation filter |
| ┤ | Tee in microfluidic channel | | Vent with valve |
| ⇔ | Reciprocating process flow | ▭ | Reaction, reagent, or bellows chamber |
| ⇒ | Unidirectional process flow | ○ | Waste receptacle |
| | Detection chamber with test pads and optical window | | Detection chamber with optical window | ular to 5′ and 3′ sequences of the template respectively. The mixture is first heated to denature or "melt" the double stranded target and then allowed to chill down so as to anneal or "hybridize", forming mixed primer/target hybrids. Following hybridization, a suitable polymerase can bind to the primer/target hybrids and "extend" the primers along the single stranded template, adding bases at the 3′-OH end of the primer, so as to form a complementary strand. In the presence of both forward and reverse primers, a complete copy of the original double stranded target is made. The steps of denaturation, hybridization, and polymerase extension can be repeated as often as needed to "amplify" the target copy number by several log orders, aiding in its detection. The ultimate number of copies is limited only by the molar quantity of the primers, which—it is important to recognize—are incorporated into the product.

SEQUENCE LISTING

```
<160> NUMBER OF SEQ ID NOS: 28

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
cgccagtacg atattcag                                                 18

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
acctggacat cacggctttc aac                                           23

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
cctattgcag agcgaatgac                                               20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
tgaactccat taacgccaga                                               20

<210> SEQ ID NO 5
<211> LENGTH: 19
```

```
<212> TYPE: DNA
<213> ORGANISM: Artificial Sequence
<220> FEATURE:
<223> OTHER INFORMATION: Primer

<400> SEQUENCE: 5
cgacctgacc aaatgccag                                               19

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
cctataacag cacccactat acgg                                         24

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
ctctgcgagc atggtctgg                                               19

<210> SEQ ID NO 8
<211> LENGTH: 10
<212> TYPE: PRT
<213> ORGANISM: Artificial Sequence
<220> FEATURE:
<223> OTHER INFORMATION: Peptide epitope selected on availability of
      complementary antibodies

<400> SEQUENCE: 8

Glu Gln Lys Leu Ile Ser Glu Glu Asp Leu
 1               5                  10

<210> SEQ ID NO 9
<211> LENGTH: 9
<212> TYPE: PRT
<213> ORGANISM: Artificial Sequence
<220> FEATURE:
<223> OTHER INFORMATION: Peptide epitope selected on availability of
      complementary antibodies

<400> SEQUENCE: 9

Tyr Pro Tyr Asp Val Pro Asp Tyr Ala
 1               5

<210> SEQ ID NO 10
<211> LENGTH: 11
<212> TYPE: PRT
<213> ORGANISM: Artificial Sequence
<220> FEATURE:
<223> OTHER INFORMATION: Peptide epitope selected on availability of
      complementary antibodies

<400> SEQUENCE: 10

Tyr Thr Asp Ile Glu Met Asn Arg Leu Gly Lys
 1               5                  10

<210> SEQ ID NO 11
<211> LENGTH: 10
<212> TYPE: PRT
<213> ORGANISM: Artificial Sequence
```

```
<220> FEATURE:
<223> OTHER INFORMATION: Peptide epitope selected on availability of
      complementary antibodies

<400> SEQUENCE: 11

Cys Glu Glu Glu Glu Tyr Met Pro Met Glu
1               5                   10

<210> SEQ ID NO 12
<211> LENGTH: 6
<212> TYPE: PRT
<213> ORGANISM: Artificial Sequence
<220> FEATURE:
<223> OTHER INFORMATION: Peptide epitope selected on availability of
      complementary antibodies

<400> SEQUENCE: 12

Thr Asp Phe Tyr Leu Lys
1               5

<210> SEQ ID NO 13
<211> LENGTH: 6
<212> TYPE: PRT
<213> ORGANISM: Artificial Sequence
<220> FEATURE:
<223> OTHER INFORMATION: Peptide epitope selected on availability of
      complementary antibodies

<400> SEQUENCE: 13

Asp Thr Tyr Arg Tyr Ile
1               5

<210> SEQ ID NO 14
<211> LENGTH: 11
<212> TYPE: PRT
<213> ORGANISM: Artificial Sequence
<220> FEATURE:
<223> OTHER INFORMATION: Peptide epitope selected on availability of
      complementary antibodies

<400> SEQUENCE: 14

Gln Pro Glu Leu Ala Pro Glu Asp Pro Glu Asp
1               5                   10

<210> SEQ ID NO 15
<211> LENGTH: 24
<212> TYPE: DNA
<213> ORGANISM: Artificial Sequence
<220> FEATURE:
<223> OTHER INFORMATION: 3' Primer - Peptidyl Oligomer

<400> SEQUENCE: 15
caatgtagaa cgaccccata aaca                                          24

<210> SEQ ID NO 16
<211> LENGTH: 23
<212> TYPE: DNA
<213> ORGANISM: Artificial Sequence
<220> FEATURE:
<223> OTHER INFORMATION: 3' Primer - Peptidyl Oligomer

<400> SEQUENCE: 16
gccattctaa ccaaagcatc ata                                           23

<210> SEQ ID NO 17
<211> LENGTH: 20
<212> TYPE: DNA
<213> ORGANISM: Artificial Sequence
```

```
<220> FEATURE:
<223> OTHER INFORMATION: 3' Primer - Peptidyl Oligomer

<400> SEQUENCE: 17
actcccgaca cgccatagaa                                              20

<210> SEQ ID NO 18
<211> LENGTH: 24
<212> TYPE: DNA
<213> ORGANISM: Artificial Sequence
<220> FEATURE:
<223> OTHER INFORMATION: 3' Primer - Peptidyl Oligomer

<400> SEQUENCE: 18
ctatccaaca agttcaattc atcc                                         24

<210> SEQ ID NO 19
<211> LENGTH: 22
<212> TYPE: DNA
<213> ORGANISM: Artificial Sequence
<220> FEATURE:
<223> OTHER INFORMATION: 3' Primer - Peptidyl Oligomer

<400> SEQUENCE: 19
agacgtatgt agattcgctg aa                                           22

<210> SEQ ID NO 20
<211> LENGTH: 20
<212> TYPE: DNA
<213> ORGANISM: Artificial Sequence
<220> FEATURE:
<223> OTHER INFORMATION: 3' Primer - Peptidyl Oligomer

<400> SEQUENCE: 20
ctggatgcat ctctggtcat                                              20

<210> SEQ ID NO 21
<211> LENGTH: 19
<212> TYPE: DNA
<213> ORGANISM: Artificial Sequence
<220> FEATURE:
<223> OTHER INFORMATION: 3' Primer - Peptidyl Oligomer

<400> SEQUENCE: 21
ggcgaatacc cagcgacat                                               19

<210> SEQ ID NO 22
<211> LENGTH: 23
<212> TYPE: DNA
<213> ORGANISM: Artificial Sequence
<220> FEATURE:
<223> OTHER INFORMATION: 5' Primer - Biotinylated Oligomer

<400> SEQUENCE: 22
tatctggttg atttcctgat cgc                                          23

<210> SEQ ID NO 23
<211> LENGTH: 25
<212> TYPE: DNA
<213> ORGANISM: Artificial Sequence
<220> FEATURE:
<223> OTHER INFORMATION: 5' Primer - Biotinylated Oligomer

<400> SEQUENCE: 23
aaatgatgag gcaaaaagta gaaca                                        25
```

-continued

```
<210> SEQ ID NO 24
<211> LENGTH: 19
<212> TYPE: DNA
<213> ORGANISM: Artificial Sequence
<220> FEATURE:
<223> OTHER INFORMATION: 5' Primer - Biotinylated Oligomer

<400> SEQUENCE: 24
ggacattgcc cgggataaa                                             19

<210> SEQ ID NO 25
<211> LENGTH: 18
<212> TYPE: DNA
<213> ORGANISM: Artificial Sequence
<220> FEATURE:
<223> OTHER INFORMATION: 5' Primer - Biotinylated Oligomer

<400> SEQUENCE: 25
ttacccgacg cctcaaac                                              18

<210> SEQ ID NO 26
<211> LENGTH: 22
<212> TYPE: DNA
<213> ORGANISM: Artificial Sequence
<220> FEATURE:
<223> OTHER INFORMATION: 5' Primer - Biotinylated Oligomer

<400> SEQUENCE: 26
agacgtatgt agattcgctg aa                                         22

<210> SEQ ID NO 27
<211> LENGTH: 20
<212> TYPE: DNA
<213> ORGANISM: Artificial Sequence
<220> FEATURE:
<223> OTHER INFORMATION: 5' Primer - Biotinylated Oligomer

<400> SEQUENCE: 27
ggaatgcaaa tcagtcgtca                                            20

<210> SEQ ID NO 28
<211> LENGTH: 19
<212> TYPE: DNA
<213> ORGANISM: Artificial Sequence
<220> FEATURE:
<223> OTHER INFORMATION: 5' Primer - Biotinylated Oligomer

<400> SEQUENCE: 28
gccgatgcca aatcgtcag                                             19
```

INTEGRATED NUCLEIC ACID ASSAYS

CROSS-REFERENCE TO RELATED APPLICATIONS

This application is a continuation of International PCT Patent Application No. PCT/US2007/006584, filed Mar. 15, 2007, now pending, which claims the benefit under 35 U.S.C. 119(e) of U.S. Provisional Patent Application No. 60/782,649, filed Mar. 15, 2006, and U.S. Provisional Patent Application No. 60/844,811, filed Sep. 14, 2006. These applications are incorporated herein by reference in their entireties.

STATEMENT OF GOVERNMENT INTEREST

This invention was made with government support under Contract No. UO1 AI061187, awarded by the National Institutes of Health. The government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 660115_457C1_SEQUENCE_LISTING.txt. The text file is 6 KB, was created on Feb. 4, 2009, and is being submitted electronically via EFS-Web.

BACKGROUND OF THE INVENTION

1. Field of the Invention

The present invention relates to the general fields of molecular biology and medical science, and more particularly to integrated microfluidic cartridges for nucleic acid extraction, amplification, and detection from clinical samples.

2. Description of the Related Art

There has been a dramatic transition in clinical laboratory diagnostic assays from the macroscale to the microscale, with specimen volume requirements decreasing from milliliters to microliters, and the possibility of reducing assay times from hours to minutes.

These improvements are due in part to advances in materials and fabrication, to the rapidity of mass and heat transfer at the microscale, and to increases in detection sensitivity, but also represent a continuing effort at innovation.

The engineering of microfluidic devices continues to be the focus of competitive research, and there is a neglected need for improvement in safe handling of fluids. In adapting these devices for clinical diagnosis, special features are needed to guard against and detect false positives, such as from sample contamination, and to protect the operator from exposure to biohazards. Ideally, single-entry devices are needed that seamlessly integrate sample preparation, extraction, and analysis without operator exposure.

PCR (U.S. Pat. Nos. 4,683,195, 4,683,202 and 4,965,188; all incorporated herein by reference) is used to increase the concentration of a target nucleic acid sequence in a sample without cloning, and requires only the availability of target sequence information sufficient to design suitable forward and reverse oligonucleotide primers, typically 10 to 30 base pairs in length. In practice, a molar excess of the primer pair is added to the sample containing the desired target or "template." The two primers are complementary to 5′ and 3′

Subsequent to the discovery of PCR, other distinct strategies for amplification were described. See, for example, U.S. Pat. No. 5,130,238 to Malek, entitled "Nucleic Acid Sequence Based Amplification" or NASBA [see also van Gemen et al. 1993. J Virol Methods 43:177-188]; U.S. Pat. No. 5,354,668 to Auerbach, entitled "Isothermal Methodology"; U.S. Pat. No. 5,427,930 to Burkenmeyer, entitled "Ligase Chain Reaction" or LCR [see also European Patent No. 320308; and Schachter et al. 1994. J Clin Microbiol 32:2540-2543]; U.S. Pat. No. 5,455,166 to Walker, entitled "Strand Displacement Amplification" or SDA [see also Walker J et al. 1993. PCR Methods and Applications 3:1-6; Lage J M et al. 2003. Hyperbranched strand displacement amplification. Genome Res 13:294-307; Dean F B 2002. Multiple displacement amplification. Proc NAS 99:5261-66; or Detter J C 2004. Isothermal strand displacement amplification. Genomics 80:691-698], transcription-mediated amplification [see Pfyffer et al. 1996. J Clin Micro 34:834-841]; all of which are incorporated herein by reference. These protocols have various advantages in diagnostic assays, but PCR remains the workhorse in the molecular biology laboratory.

Semi-automated devices for use with the new amplification methodologies followed shortly after the introduction of PCR. The first commercial thermocycler was manufactured under U.S. Pat. No. 5,038,852 to Cetus Corp.

In 1990, the University of Utah (U.S. Pat. No. 6,787,338) disclosed a method wherein samples and reagents were drawn into glass capillaries, which were sealed and placed in an oven, and the temperature was cycled by opening and closing the oven door.

Subsequently, the University of Pennsylvania (U.S. Pat. Nos. 5,498,392; 5,587,128; 5,955,029; 6,953,675) disclosed microfabricated silicon-based devices for performing PCR. Envisaged without particulars was a family of small, mass produced, typically one-use, disposable "chips" for rapid amplification of cellular or microbial nucleic acids in a sample. The devices included a sample inlet port, a "mesoscale" flow system, and a means for controlling temperature in one or more reaction chambers. Heating and cooling means disclosed included electrical resistors, lasers, and cold sinks. Off-chip pumps were used to control fluid flow and to deliver reagents. Printed circuits, sensors on the chip, and pre-analytical binding means for trapping and concentrating analyte were suggested. The common fluid channel, which also served as the analytical channel, was used to transport cell lysis waste (such as bacteria or blood cell lysate) to an open vent or to an off-chip site.

Analytical devices having chambers and flow passages with at least one cross-sectional dimension on the order of 0.1 µm to 500 µm were disclosed. Reaction volumes of 5 µL or lower were prophesized.

Means for detecting amplicons included, nonspecifically, DNA:DNA hybridization, either visually with fluorescent intercalating dyes or through rheological measurement, DNA binding to fluorescent probes or diamagnetic (or paramagnetic) beads; and gel electrophoresis.

While in many ways anticipating current devices, the University of Pennsylvania devices were limited to silicon chips, with sample and reagent ports under the control of external syringe pumps. Cell lysis debris exited the chip through the PCR chamber prior to amplification, and no demonstrable mechanism for isolation of the operator from a biohazardous sample or waste was provided. The design and method did not permit prior on-board incorporation of dehydrated reagents as a single-entry assay device or kit, and notwithstanding any declarations to the contrary, clearly the sharing of pump inlet and outlet ports from sample to sample poses an unacceptable risk for cross-contamination.

In U.S. Pat. No. 5,234,809, a method of purifying nucleic acids is disclosed that involves treating a biological sample, such as blood or stool, with a chaotrope in the presence of a solid substrate such as silicon dioxide or other hydrophilic, cationic solid. Earlier publications had reported the use of chaotropes and solid substrates to purify nucleic acids from agarose blocks. Depending on the nature of the solid phase, the nucleic acid could then be eluted with TE, or not. If not, PCR could be performed directly on the solid substrate, as on nucleic acid trapped on a PVDF membrane. The trapping and eluting step was reported to take about 45 minutes. However, the cited time did not include detection of amplicons. No combination of nucleic acid trapping, amplification and detection of PCR amplicons in a one-step device was disclosed. Interestingly, performance of PCR on eluted filtrates from silica filter pads was not claimed. No multiplexed on-board detection channel was provided.

In U.S. Pat. No. 5,989,813, amplicons are prepared by amplification of target nucleic acid sequences in the presence of forward and reverse primers conjugated with biotin and digoxigenin, respectively, for use in lateral flow assays. The amplicons are bound to particles with streptavidin and agglutinate in the presence of antibody to digoxigenin. By lateral flow, bifunctional amplicon complexes are detected as trapped aggregates excluded from the fibrous matrix. Other solids are interferences in the assay. In a second variant of the lateral flow format, avidin conjugates are wicked into a membrane and migrate until encountering a detection strip. Accumulation of dyed particles at the detection strip is detected. The assays are generally dependent on flow rate in the materials, particle size and pore dimensions as well as laminar barriers to diffusion. No multiplexed on-board detection utility was provided.

Other designs and methods of PCR thermocycling have since been introduced and patented. U.S. Pat. No. 6,210,882 to the Mayo Clinic described means for non-contact heating and cooling for thermocycling reactions. U.S. Pat. No. 5,965,410 to Caliper described means for thermocycling by Joule heating, that is, by the passage of electric current through the buffer of the reaction vessel. U.S. Patent Application 20040081997 to Caliper described PCR reactions in which primers, dNTPs, and the target nucleic acid sequence (template) were first mixed, denatured and re-annealed before polymerase was added (the so-called "hot start" polymerase reaction). Hot Start PCR was earlier suggested to improve product yield and specificity (D'Aquila et al, 1991. Nucleic Acids Res 19:37-49; Chou et al, 1992. Nucleic Acids Res 20:1717-1723; Kellogg et al, 1994. Biotechniques 16: 1134-1137).

Another system for controlling temperature on a microfluidic device is described in U.S. Pat. No. 6,541,274. This patent is directed to a reactor system having a plurality of reservoirs in a body. A heat exchanger and circulating pump is connected with the reservoirs to control the temperature. Other examples of existing devices for controlling temperature on a microfluidic device include radiant heat as described in U.S. Pat. No. 6,018,616, a temperature controlled block as described in U.S. Pat. No. 6,020,187, and other cumulative improvements still being filed with the USPTO.

U.S. Pat. No. 5,716,842 to Biometra described a reactor having a serpentine linear flow microchannel, which crisscrosses heating elements at different temperatures for PCR. U.S. 2001/0046701 to Sentron describes the use of primer attached to particulate reagents for PCR in a serpentine channel followed by absorption-enhanced H-filtration to recover the amplicons. U.S. Pat. No. 5,270,183 describes a reaction chamber coiled around various heating manifolds.

In U.S. Patent Application 2003008308, CalTech described a "rotary microfluidic channel" with multiple temperature zones, so that thermocycling can be performed by circulation of the reaction mixture around an inventive circular channel. The application also teaches the use of accessory channels "formed within an elastomeric material and separated from the flow channel by a section of an elastomeric membrane, the membrane being deflectable into or retractable from the substantially circular flow channel in response to an actuation force applied to the control channel" (Para. 9, FIGS. 3A, 3B). These elastomeric elements were termed "isolation valves" but also served as positive displacement pumps in the devices, again by impinging on the fluid channel under positive pneumatic pressure, whereby the elastomeric element was reversibly deformed and protruded into the fluid channel in the manner of a series of plunger-type peristaltic pump elements. Heating for thermocycling was accomplished with Peltier device, resistive heater, heat exchanger or an indium tin oxide element. By immobilizing the polymerase in one segment of the circular channel not contacted with a hot heating element, use of thermolabile polymerases was suggested.

Proposed detection means included, non-specifically, tagging targets with then-known fluorophores (e.g., as "molecular beacons" or "FRET" tags), chromophores, radioisotopes, luminescence labels, mass labels, enzyme-conjugated oligomeric labels, or by gel electrophoresis. Detection by measuring the capacitance of the reaction solution was disclosed.

U.S. Patent Application 20050019792 to Fluidigm described another elastomeric valve. Other details are provided in U.S. Patent Application 20020195152 to Fluidigm. Pneumatic valves were modified to incorporate a platen which compresses a fluid channel in an elastomeric body, closing or throttling the channel. Devices consisting of blind flow channels, which serve as reaction chambers, and are preloaded with reagents at time of manufacture, were also proposed.

U.S. Patent Application 20060073484 to Mathies described single channel or dense network microfluidic devices under control of a pneumatic manifold. The method involved the use of immunoaffinity capture of target pathogens, followed by lysis and detection by polymerase chain reaction (PCR) with capillary electrophoresis (CE). Pneumatically switchable control valves, consisting of a PDMS elastic film sandwiched between a glass fluidic and pneumatic manifold layer (with optional via layer interposed), were used to either open channels by applying vacuum or close channels by applying pressure (see FIG. 1C of U.S. Patent Application 20060073484). Similar structures were also used as pumps for dispensing reagents (see FIG. 5C of U.S. Patent Application 20060073484). [See also, William H. Grovera et al. 2003. Monolithic membrane valves and diaphragm pumps for practical large-scale integration into glass microfluidic devices. Sensors and Actuators B 89 (3):315-323.] PDMS films were particularly preferred because silane elastomers bond to the glass plates of these devices.

U.S. Patent Application 20050129582 co-assigned to Micronics teaches microfluidic devices having channels, valves, pumps, flow sensors, mixing chambers and optical detectors for performance of chemical and biochemical assays, and is herein incorporated in full by reference. Improved thermal transitions were disclosed, enabling performance of PCR more than 4 times faster than conventional thermocyclers. Thermal ramping rates of up to 17 C/sec were demonstrated by selection of suitable plastic substrates and dimensions.

Co-assigned patents and patent applications relevant to the development methods for nucleic acid and antibody bioassays in a microfluidic assay format include U.S. Pat. No. 6,743,399 ("Pumpless Microfluidics"), U.S. Pat. No. 6,488,896 ("Microfluidic Analysis Cartridge"), U.S. Patent Applications 2005/0106066 ("Microfluidic Devices for Fluid Manipulation and Analysis"), 2002/0160518 ("Microfluidic Sedimentation"), 2003/0124619 ("Microscale Diffusion Immunoassay"), 2003/0175990 ("Microfluidic Channel Network Device"), 2005/0013732 ("Method and system for Microfluidic Manipulation, Amplification and Analysis of Fluids, For example, Bacteria Assays and Antiglobulin Testing"), U.S. Patent Application 2007/0042427, "Microfluidic Laminar Flow Detection Strip", and unpublished documents "Microfluidic Cell Capture and Mixing Circuit", "Polymer Compositions and Hydrogels", "Microfluidic Mixing and Analytical Apparatus," "System and method for diagnosis of infectious diseases", and "Microscale Diffusion Immunoassay Utilizing Multivalent Reactants", all of which are hereby incorporated in full by reference.

Other illustrations of microfluidic devices and their components may be found in U.S. Pat. Nos. 5,726,751; 5,724,404; 5,716,852; 5,747,349; 5,748,827; 5,922,210; 5,932,100; 5,974,867; 5,971,158; 5,972,710; 5,948,684; 6,007,775; 6,171,865, and 6,387,290 (hereby incorporated by reference in their entirety).

U.S. Pat. No. 5,582,989 teaches the use of multiplex PCR to detect genetic errors in multiple target exons. Purified gDNA was prepared by the standard methods of the time, followed by PCR, with detection by agarose gel electrophoresis, or by Southern blot. A simplified, integrated microfluidic approach to genetic analysis was not anticipated.

U.S. Pat. No. 5,582,989, incorporated herein by reference, teaches the use of multiplex PCR to detect infectious agents in clinical samples. The key teaching of the procedure is a high-salt buffer used to extract the DNA from proteins, which are salted out. DNA was then further purified by phenol:chloroform extraction before PCR. Finally, PCR was performed using a Perkin Elmer 9600 thermocycler (Norwalk, Conn., USA). The protocol was described as taking about a day to complete. No on-board multiplexed detection utility was provided.

U.S. Pat. No. 7,087,414 to Applera described a two stage assay including a preparative step in which a mixed primer pool was used for preliminary rounds of amplification (to no more than 1000 copies per target), and the reaction mixture was then split into separate parallel reaction microwells for subsequent second-stage amplifications, termed "boost" cycles, in which single, target-specific primer pairs were used. Amplification was followed by detection in separate analytical channels. Microfluidic devices with integrated one-step extraction, amplification and detection were not anticipated. No on-board multiplexed detection utility was provided.

Accordingly, there remains an unfulfilled need for an integrated, one-step microfluidic assay device capable of sample processing and nucleic acid capture, amplification of target sequences, and detection of positive results. There is a need for devices that deliver results in real time with minimal delay. This need is particularly apparent in the fight against infectious diseases—where patients must be evaluated and treated without the option of a return visit—where rapid identification of an etiological agent is used for real time monitoring and control of epidemics—where specialized facilities for handling biohazardous samples may not be available—where the testing must be performed absent skilled microbiologists—and where the cost of more complex diagnostic services is prohibitive.

Ease of use would be improved if multiple results were displayed in parallel, as for example the results of a panel of tests, in a user friendly, visual detection chamber.

BRIEF SUMMARY OF THE INVENTION

Physicians faced with a patient having generalized malaise, or an unpathognomic syndrome such as gastroenteritis and diarrhoea, or the onset of a respiratory syndrome beginning with runny nose or lymphadenitis, typically rely on epidemiological and statistical considerations in deciding what to prescribe. However, in a world where travelers can arrive from the other side of the world in the space of a night's passing, these considerations are often useless.

Etiological agents that produce gastroenteritis, diarrhoea, dysentery, or cholera-like symptoms can be clinically confused, particularly when presented early in their course, and can require laboratory testing. Differential diagnosis of the causative agent can be critical in prescribing proper treatment.

For example, diarrhoea caused by enterohemorrhagic *E. coli*, often the serotype O157H7 (referring to capsular and flagellar antigenic markers), might not best be treated with cytolytic antibiotics because the resultant bolus of toxin released when the bacteria lyse can overwhelm the host.

Respiratory pathogens have symptoms that can overlap in clinical examination. Differential diagnosis of the causative agent can be critical in prescribing proper treatment.

For example, failure to treat *S. pyogenes* aggressively with bacteriocidal antibiotics can result in permanent damage to the myocardium. Data has conclusively shown that decreased lifespans and increased cardiac-related morbidity and mortality is related to untreated "strep throat", particularly in childhood. In numerous surveys of third world countries lacking access to antibiotics, the prevalence of heart disease early in life can be as much as 30% or even 70% of the population.

Therefore, in an effort to reduce the pervasive dangers of the spread of infectious diseases, we have been lead by a molecular biological nostrum, "extract-amplify-detect,", to design microfluidic devices that are sanitary, compact, easy to use, require small sample volumes, and offer differential laboratory diagnosis of a plurality of microbes or viruses in real time at the point-of-care.

One goal of this project has been the development of a seamless interface between sample preparation, amplification, and target detection in a microfluidic device. Surprisingly, all steps in the assay protocol, from extraction of nucleic acid, to amplification, to detection, can be performed in about 4 minutes in a single-entry self-contained cartridge resembling a card.

Other embodiments include an on-board "multiplex detection chamber", whereby multiple results, as from a panel of tests, are displayed in a user-friendly visual format.

The disclosed single-entry microfluidic devices utilize a plurality of microfluidic channels, valves, filters, pumps, liquid barriers, on-board reagent reservoirs, and other elements organized as a combination of fluidic subcircuits that extract nucleic acids from the sample, amplify putative target nucleic acid sequences, and detect assay results in a format accessible to the user.

Pathogens from clinical samples that would have confusing or inconclusive results by gel electrophoresis of amplified products, and would require confirmatory Southern Blot, are readily identified in minutes by the methods described here.

In current embodiments, extraction is accomplished in a microchannel 4 cm or less in length, without pretreatment with proteinases or phenol:chloroform precipitation and associated centrifugations.

Also disclosed are improvements in the microfluidic device format that address the hazardous nature of the specimens to be analyzed, overcoming drawbacks of past devices. In selected embodiments, we demonstrate an integrated approach to specimen handling and extraction in disposable, single-entry devices, where the specimen is inserted or pipetted into the device, sealed inside, and the assay is then conducted without further exposure of the operator to the specimen. On-board waste sequestration and decontamination is also provided.

In another aspect of the invention, we also show that peptidyl-conjugates to the 5' tail of amplification primer sets are generally applicable in polymerase-dependent amplification protocols and are further robust, surprisingly retaining full antigenicity and binding integrity following amplification. We show that an immobilized antibody, for example a monoclonal antibody, specific to a peptidyl hapten-conjugated amplification primer will capture the target amplicon tagged with the primer. By using a second primer tagged with a second affinity ligand, methods employing target specific detection complexes are readily designed. Oligopeptides have not previously been used as primers in PCR amplification, or other amplification protocols, or used as means for tagging and discriminating mixed PCR products in multiplex target detection protocols. These complexes thus serve essentially as means for interrogating a peptidyl-primer amplicon library. Unexpectedly, this method has more breadth than prior art methods of tagging primers, permitting simultaneous separation and detection of an essentially infinite number of amplicons by the step of tagging each amplicon with a unique peptide hapten and employing the corresponding antibody to immobilize it. The magnetic bead assays illustrated here are one embodiment of this discovery.

BRIEF DESCRIPTION OF THE SEVERAL VIEWS OF THE DRAWINGS

FIG. 11 is a sectional view of a waste sequestration chamber with sanitary vent.

FIG. 12 is a plan and sectional view of a bellows chamber with elastomeric diaphragm.

FIG. 13 is a plan view of an amplification subcircuit having two reciprocating bellows pump chambers with independently controllable fixed temperature thermal interfaces.

FIG. 15 is a plan view of an amplification subcircuit having two reciprocating bellows pump chambers with independently controllable fixed temperature thermal interfaces and with through-flow.

FIG. 28 is a key to the graphical symbols used in FIGS. 1-4.

DETAILED DESCRIPTION OF THE INVENTION

Figure 1:
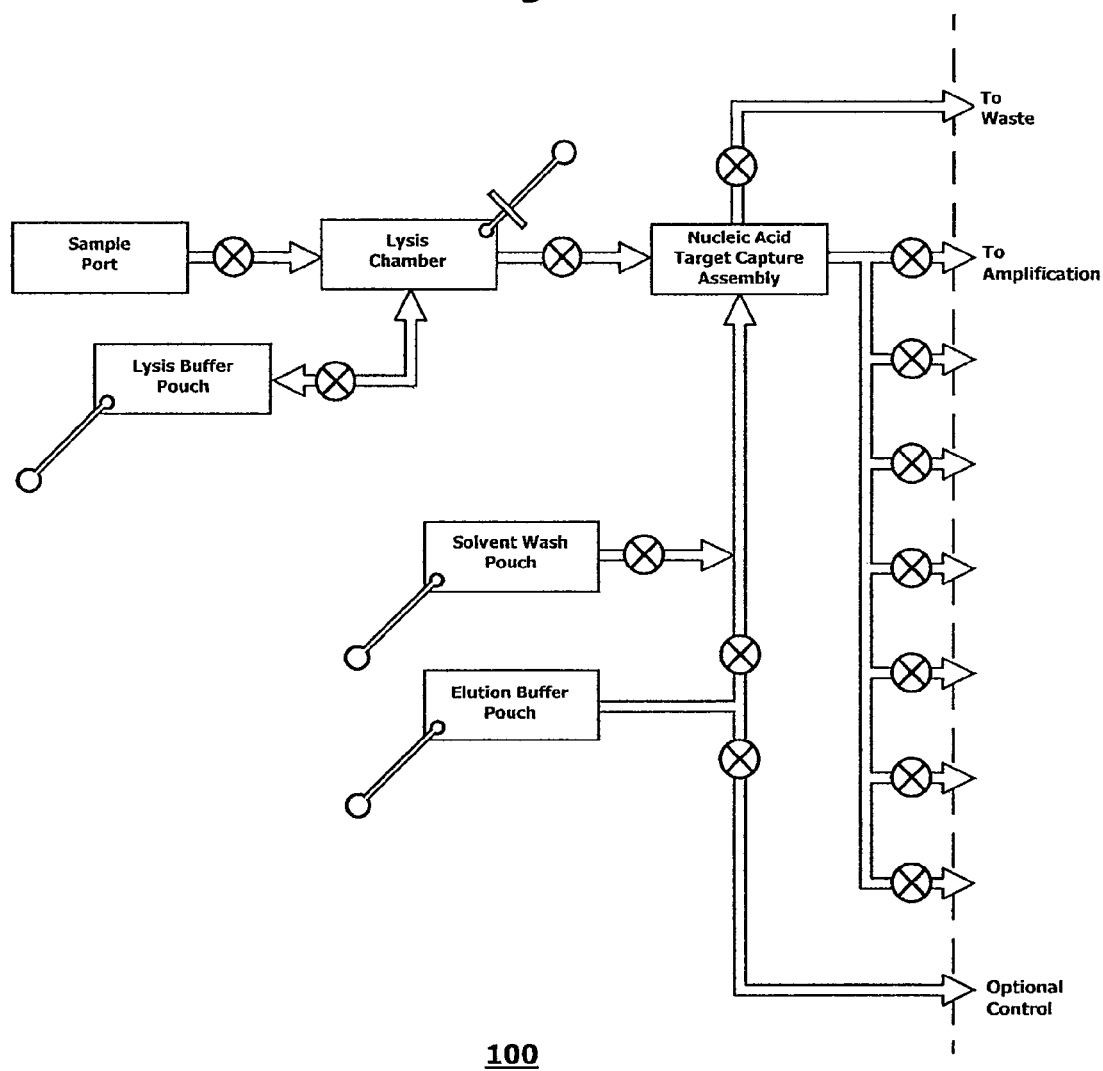
FIG. 1 is a schematic of a microfluidic sample-extraction subcircuit.

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

The following definitions are provided as an aid in interpreting the claims and specification herein. Where works are cited by reference, and definitions contained therein are inconsistent in part or in whole with those supplied here, the definition used therein may supplement but shall not supercede or amend the definition provided herein.

1. Definitions

Test samples: Representative biosamples include, for example: blood, serum, plasma, buffy coat, saliva, wound exudates, pus, lung and other respiratory aspirates, nasal aspirates and washes, sinus drainage, bronchial lavage fluids, sputum, medial and inner ear aspirates, cyst aspirates, cerebral spinal fluid, stool, diarrhoeal fluid, urine, tears, mammary secretions, ovarian contents, ascites fluid, mucous, gastric fluid, gastrointestinal contents, urethral discharge, synovial fluid, peritoneal fluid, meconium, vaginal fluid or discharge, amniotic fluid, semen, penile discharge, or the like may be tested. Assay from swabs or lavages representative of mucosal secretions and epithelia are acceptable, for example mucosal swabs of the throat, tonsils, gingival, nasal passages, vagina, urethra, rectum, lower colon, and eyes, as are homogenates, lysates and digests of tissue specimens of all sorts. Mammalian cells are acceptable samples. Besides physiological fluids, samples of water, industrial discharges, food products, milk, air filtrates, and so forth are also test specimens. In some embodiments, test samples are placed directly in the device; in other embodiments, pre-analytical processing is contemplated.

Bioassay Target Molecule: or "analyte of interest", or "target molecule", may include a nucleic acid, a protein, an antigen, an antibody, a carbohydrate, a cell component, a lipid, a receptor ligand, a small molecule such as a drug, and so forth. Target nucleic acids include genes, portions of genes, regulatory sequences of genes, mRNAs, rRNAs, tRNAs, siRNAs, cDNA and may be single stranded, double stranded or triple stranded. Some nucleic acid targets have polymorphisms, deletions and alternate splice sequences. Multiple target domains may exist in a single molecule, for example an immunogen may include multiple antigenic determinants. An antibody includes variable regions, constant regions, and the Fc region, which is of value in immobilizing antibodies.

Pathogen: an organism associated with an infection or infectious disease.

Pathogenic condition: a condition of a mammalian host characterized by the absence of health, i.e., a disease, infirmity, morbidity, or a genetic trait associated with potential morbidity.

Nucleic acid: The terms "nucleic acid," "polynucleotide," and "oligonucleotide" are used herein to include a polymeric form of nucleotides of any length, including, but not limited to, ribonucleotides and deoxyribonucleotides. Relatively short nucleic acid polymers are often used as "primers" or "probes". The definition encompasses nucleic acids from natural sources which can be methylated or capped, and also synthetic forms, which can contain substitute or derivatized nucleobases and may be based on a peptide backbone. Nucleic acids are generally polymers of adenosine, guanine, thymine, and cytosine and their "deoxy-" forms, but may also contain other pyrimidines such as uracil and xanthine, or spacers and universal bases such as deoxyinosine. Deoxynucleic acids may be single-stranded or double-stranded depending on the presence or absence of complementary sequences, and on conditions of pH, salt concentration, temperature, and the presence or absence of certain organic solvents such as formamide, n,n-dimethylformamide, dimethylsulfoxide, and n-methylpyrrolidinone.

"Target nucleic acid sequence" or "template": As used herein, the term "target" refers to a nucleic acid sequence in a biosample that is to be amplified in the assay by a polymerase and detected. The "target" molecule can be present as a "spike" or as an uncharacterized analyte in a sample, and may consist of DNA, cDNA, gDNA, RNA, mRNA, rRNA, or miRNA, either synthetic or native to an organism. The "organism" is not limited to a mammal. The target nucleic acid sequence is a template for synthesis of a complementary sequence during amplification. Genomic target sequences are denoted by a listing of the order of the bases, listed by convention from 5' end to 3' end.

Reporter, "Label" or "Tag": refers to a biomolecule or modification of a biomolecule that can be detected by physical, chemical, electromagnetic and other related analytical techniques. Examples of detectable reporters include, but are not limited to, radioisotopes, fluorophores, chromophores, mass labels, electron dense particles, magnetic particles, dyed particles, QDots, spin labels, molecules that emit chemiluminescence, electrochemically active molecules, enzymes, cofactors, enzymes linked to nucleic acid probes, and enzyme substrates. Reporters are used in bioassays as reagents, and are often covalently attached to another molecule, adsorbed on a solid phase, or bound by specific affinity binding.

Ligand: any molecule for which there exists another molecule (i.e., an "antiligand" or ligand binding molecule) that binds with specific affinity to the ligand with stereochemical recognition or "fit" of some portion of the ligand by the ligand binding molecule. Forces between ligand and binding molecule are typically Van der Waals, hydrogen bond, hydrophobic bond, and electrostatic bond. Ligand binding is not typically covalent and is thus distinguished from "crosslinked" and "derivatized". As used herein, the term "ligand" is reserved for binding moieties that are not "Peptidyl haptens".

Peptidyl hapten: Refers to a subclass of haptens that is a peptide fragment. As used herein, peptidyl haptens are used with their complementary antibody to the peptide fragment as a means for capturing two-tailed amplicons.

Hapten is a "molecular key" recognized by an antibody, and when bound to an immunogenic carrier and introduced into a vertebrate, a hapten will elicit formation of antibodies specific for the hapten or epitope. These molecular keys have stereochemical specificity, are generally exposed on the surface of the carrier, and are of lower molecular weight than the carrier. Illustrative examples include small-molecule derivatives of native proteins, RNA loop-stem structures, a drug or steroid such as digoxigenin, the carbohydrate side-chains that decorate a mucopeptide, and short chain peptides or helices of non-native proteins such as diphtheria toxin or toxoid. Even a dipeptide or a lipid, when conjugated on a suitable immunogenic carrier, can produce an antibody response, and affinity-captured antibody specific to the dipeptide or lipid itself, not the immunogen, can be produced by absorbing out the non-specific antibodies in an antiserum or by preparing a monoclonal antibody by lymphocyte selection. Although a hapten is not immunogenic of itself, it has very finely directed immunospecificity and is recognized by a very limited set of complementary antibodies.

As used herein, short chain peptides are a preferred hapten for tagging amplicons as used to create peptidyl-tagged amplicon libraries because of their robust chemistry, compatibility with enzymes as primer labels, and essentially infinite immunospecificity.

Capture agent: or "affinity capture agent" is a generic term for a complementary partner in an affinity binding pair and is generally used to capture a ligand or hapten by binding it to a solid phase. Affinity binding pairs include streptavidin:biotin, antibody:antigen, hapten:antibody, and antigen:antibody, for example and either member of the affinity binding pair may be the capture agent.

Test pad area—or test strip, or test field, or simply "test pad", as used herein, is an area or zone occupied by an affinity capture agent. The area is 3-dimensional at a nanomolecular level and is generally formed on the surface of a substrate in a liquid flow path. The test pad is generally the site in the assay where the assay endpoint is observed or measured, and as such may be housed in a detection chamber with optical window.

Heterogeneous capture or immobilization: refers use of affinity binding pairs to concentration an analyte or detection complex on a solid phase surface, particle, or porous adsorbent material. Heterogeneous or solid phase capture may be achieved with capture agents such as immobilized antigen, antibody, avidin, nickel-NTA, lectin, or other ligand/receptor systems. As referred to herein, the molecular complex formed by heterogeneous capture is the "immobilized reporter complex". Such complexes are stabilized by non-covalent and cooperative binding.

Immobilized: Assays can be built up from reagents that serve to capture and concentrate the analyte at a defined location or surface in the device, such as a test pad. The terms "immobilize" or "immobilized" as used herein indicate that analyte and affinity capture reagent binding is effectually irreversible under conditions of the assay.

Probe: A "probe" is a nucleic acid capable of binding to a target nucleic acid by complementary base pairing with sufficient complementarity to form a stable double helix at room temperature. Probes may be labeled with reporter groups. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. Tools for selection of a probe sequence, length, and hybridization conditions are generally familiar to those skilled in the art.

Amplification: As used here, the term "amplification" refers to a "template-dependent process" that results in an increase in the concentration of a nucleic acid sequence relative to its initial concentration. A "template-dependent process" is a process that involves "template-dependent extension" of a "primer" molecule. A "primer" molecule refers to a sequence of a nucleic acid that is complementary to a known portion of the target sequence. A "template dependent extension" refers to nucleic acid synthesis of RNA or DNA wherein the sequence of the newly synthesized strand of nucleic acid is dictated by the rules of complementary base pairing of the target nucleic acid and the primers.

Amplicon refers to a double stranded DNA product of a prior art amplification means, and includes double stranded DNA products formed from DNA and RNA templates.

Two-tailed Amplicon refers to a double stranded DNA product of an amplification means in which tagged primer pairs are covalently incorporated, a first primer conjugated with a peptide hapten or epitope, a second primer conjugated with an affinity reporter, tag or "ligand". As used herein, the two-tailed amplicon functions as a "hetero-bifunctional" tether, and forms a molecular detection complex on a solid substrate.

Primer: as used herein, is a single-stranded polynucleotide or polynucleotide conjugate capable of acting as a point of initiation for template-directed DNA synthesis in the presence of a suitable polymerase and cofactors. Primers are generally at least 7 nucleotides long and, more typically range from 10 to 30 nucleotides in length, or longer. The term "primer pair" refers to a set of primers including a 5' "forward" or "upstream" primer that hybridizes with the complement of the 5' end of the DNA template to be amplified and a 3' "reverse" or "downstream" primer that hybridizes with the 3' end of the sequence to be amplified. Note that both primers have 5' and 3' ends and that primer extension always occurs in the direction of 5' to 3'. Therefore, chemical conjugation at or near the 5' end does not block primer extension by a suitable polymerase. Primers may be referred to as "first primer" and "second primer", indicating a primer pair in which the identity of the "forward" and "reverse" primers is interchangeable. Additional primers may be used in nested amplification.

In the preferred embodiment, the first primer is a mono-specific or class-specific oligonucleotide conjugated to a peptide hapten or epitope recognized by a specific antibody. And the second "primer" is an oligonucleotide conjugated to a hapten, to a biotin, a digoxin, a polysaccharide, a phycoerythrin dye, a fluorophore, to an affinity binding agent, to an Fc fragment of an antibody, to a nickel chelator such as NTA, or to a lectin, and so forth, at or near the 5' terminus. Primers can be selected to be "substantially complementary" to the sequence on the template to which it is designed to hybridise and serve as a site for the initiation of synthesis.

Polymerases are enzymes defined by their function of incorporating nucleoside triphosphates, or deoxynucleoside triphosphates, to extend a 3' hydroxyl terminus of a primer molecule. For a general discussion concerning polymerases, see Watson, J. D. et al, (1987) Molecular Biology of the Gene, 4th Ed., W. A. Benjamin, Inc., Menlo Park, Calif. Examples of polymerases include, but are not limited to, *E. coli* DNA polymerase I, "Klenow" fragment, Taq-polymerase, T7 polymerase, T4 polymerase, T5 polymerase and reverse transcriptase. Examples of reverse transcriptases include HIV-1 reverse transcriptase from the human immunodeficiency virus type 1, telomerase, M-MuLV reverse transcriptase from the Moloney murine leukemia virus, and AMV reverse transcriptase from the avian myeloblastosis virus.

It should be noted that reverse transcriptase is commonly used in research to apply the polymerase chain reaction technique to RNA targets. The classical PCR technique can only be applied directly to DNA, but by using reverse transcriptase to synthesize cDNA from RNA, PCR analysis of RNA targets is possible. The technique is collectively called Reverse Transcription-Polymerase Chain Reaction (RT-PCR).

Complementary (with respect to nucleic acids) refers to two single-stranded nucleic acid sequences that can hybridize to form a double helix. The matching of base pairs in the double helix of two complementary strands is not necessarily absolute. Selectivity of hybridization is a function of temperature of annealing, salt concentration, and solvent, and will generally occur under low stringency when there is as little as 55% identity over a stretch of at least 14-25 nucleotides. Stringency can be increased by methods well known in the art. See M. Kanehisa, Nucleic Acids Res. 12:203 (1984). Regarding hybridization of primers, a primer that is "perfectly complementary" has a sequence fully complementary across the entire length of the primer and has no mismatches.

A "mismatch" refers to a site at which the base in the primer and the base in the target nucleic acid with which it is aligned are not complementary.

Complementary (with respect to immunobinding) refers to antibody:immunogen or antibody:hapten binding that is immunospecific.

Magnetic Microbead: refers to a "nanoparticle", "bead", or "microsphere", or by other terms as known in the art, having at least one dimension, such as apparent diameter or circumference, in the micron or nanometer range. An upper range of such dimensions is 600 um, but typically apparent diameter is under 200 nm, and may be 1-50 um or 5-20 nm, while not limited to such. Such particles may be composed of, contain cores of, or contain granular domains of, a paramagnetic or superparamagnetic material, such as the $Fe_2O_3$ and $Fe_3O_4$ ($\alpha$-Fe crystal type), $\alpha'$-FeCo, $\epsilon$-Cobalt, CoPt, $CrPt_3$, $SmCO_5$, Nickel and nickel alloys, $Cu_2MnAl$, $\alpha$-FeZr, $Nd_2Fe_{14}B$, NoTi, for example. Preferred are the Ferrites, defined as ferrimagnetic or ceramic compound materials consisting of various mixtures of iron oxides such as Hematite ($Fe_2O_3$) or Magnetite ($Fe_3O_4$) and iron oxides in alloys with other metals. These materials as used generally are particles having dimensions smaller than a magnetic domain, and may be formed into particles, beads or microspheres with binders such as latex polymers (generically), silica, as is generally well known and inclusive of such materials as are commercially available.

Particularly preferred are nanoparticles of $Fe_3O_4$ with diameters in the 50 nm-100 um range as are commercially available for magnetic bioseparations. These particles are "superparamagnetic", meaning that they are attracted to a magnetic field but retain no residual magnetism after the field is removed. Therefore, suspended superparamagnetic particles tagged to the biomaterial of interest can be removed from a matrix using a magnetic field, but they do not agglomerate (i.e., they stay suspended) after removal of the field. Also of interest are nickel and cobalt microbeads. These beads may be reactive with peptides containing histidine.

Paramagnetic beads have the property that they align themselves along magnetic flux lines and are attracted from areas of lower magnetic flux density to areas of higher magnetic flux density.

It should be recognized that magnetic microbeads may be composite materials. Such beads may further contain other micro- or nanoparticles agglomerated with a binder. Composites with RF-tags, QDots, up-converting fluorophores, colloid sols and clays, and the like are contemplated for use in the present invention. A magnetic bead need not be formed entirely of a magnetic material, but may instead comprise both magnetic and non-magnetic materials.

Microbeads may themselves be colloidal and have chromogenic properties, or may be combined with other colloidal metal particles with chromogenic properties. Mixed suspensions of differently modified microbeads may be used.

Microbeads are by no means simply commodities. They may be modified with surface active agents such as detergents to control their rheological properties, as in ferrofluids. The surface of microbeads may be modified by adsorption or covalent attachment of bioactive molecules, including immunoaffinity agents, antibodies, enzymes, dyes, fluorescent dyes, fluorescent quenchers, oligomers, peptide nucleomers, and the like, and more specifically by coating with streptavidin or single stranded DNA oligomers, for example. These and other cumulative prior art skills are incorporated herein in full without full recitation of their scope, as a full recitation is unnecessary to understand the principles of the current invention except insofar as to recognize that the microbeads of interest herein are comprised of at least one paramagnetic element therein, as would be readily recognized by those skilled in the prior arts.

Suitable matrices for microbeads include polystyrene, divinylbenzene, polyvinyltoluene, polyester, polyurethane, with optional functional groups selected from SO3, COOH, NH2, Glycidyl (COC), OH, Cl, Tosyl, aldehyde, and sulfhydryl. Particles often range from 0.3 to 5 um or larger. Latex particles of 100 nm, and 1, 5, 20, 50 or 100 um are commercially available in bulk. Silica may be used as a matrix or as a capsule. Derivatized silane includes OH, NH2, COOH and more. Particles often range from 0.5 to 3 um. Dextran may also be used as a matrix. Particles often range from 20-50 nm. Polysaccharide may also be used with silane as silica fortified microbeads of particle size around 250 nm. Agarose and cellulose matrices include particles in the range of 1-10 um, and may be activated for introduction of functional groups. Protein particles, such as of gelatin and albumin, have long been used for magnetic microspheres. These are readily activated for amine, carboxyl, hydroxyl and sulfhydryl linkages with ligands or tags. Liposomes are somewhat more refractory to chemical derivatization, but have been used to make magnetic particles. Naked iron oxide, and other paramagnetic metal particles are also known, and may be derivatized by adding sulfhydryl groups or chelators. These particles often have sizes of 5 to 300 nm. Certain types of particle populations are known to be uniform in size; in others the heterogeneity may be controlled or selected.

Such microbeads may be readily prepared. For example, carboxyl-modified microbeads containing ~20-60% magnetite are made by dispersing a (magnetite)/styrene/divinylbenzene ferrofluid mixture in water, and emulsion-polymerizing the monomers to trap the magnetite in a polymer matrix of microbeads of ~1 μm diameter. The magnetite is thus dispersed throughout the solid beads. Other prior art means for synthesizing and modifying microbeads are commonly known.

Suitable microbeads for practicing the present invention may also be purchased from vendors such as Bang's Laboratories, Inc. (Fishers Ind.) and Polysciences, Inc (Warrington Pa.), as well as numerous suppliers of specialty modified microbeads such as Bioscience Beads (West Warwick R.I.). Tradenames of such beads, again not as a comprehensive recitation, include Estapor® SuperParaMagnetic Microspheres, COMPEL™ Uniform Magnetic Microspheres, Dynabeads® MyOne™ Microspheres, and the like. Cobalt paramagnetic microbeads are sold as Dynabead's MyOne TALON. BioMag Plus microbeads from Polysciences have an irregular shape, and thus more surface area for affinity chemistry.

Populations—of microbeads are generally used to assay populations of assay targets. A population as used herein refers to a set of members sharing some common element or property. For example, a population of beads may be similar in that the beads share a common tag, such as an avidin coat, or a barcode. A population of nucleic acids comprising an assay target may simply share a target nucleic acid sequence, or may contain a common tag. A population of antibodies may share a common specificity. And so forth.

Paramagnetic and Superparamagnetic are taken as functionally synonymous for the present purposes. These materials when fabricated as microbeads, have the property of responding to an external magnetic field when present, but dissipating any residual magnetism immediately upon release of the external magnetic field, and are thus easily resuspended and remain monodisperse, but when placed in proximity to a magnetic field, clump tightly, the process being fully reversible by simply removing the magnetic field.

Magnetic Force Field: is the volume defined by the magnetic flux lines between two poles of a magnet or two faces of a coil. Electromagnets and driving circuitry can be used to generate magnetic fields and localized magnetic fields. Permanent magnets may also be used. Preferred permanent magnetic materials include NdFeB (Neodymium-Iron-Boron $Nd_2Fe_{14}B$), Ferrite (Strontium or Barium Ferrite), AlNiCo (Aluminum-Nickel-Cobalt), and SmCo (Samarium Cobalt). The magnetic forces within a magnetic force field follow the lines of magnetic flux. Magnetic forces are strongest where magnetic flux is most dense. Magnetic force fields penetrate most solids and liquids. A moving magnetic force field has two vectors: one in the direction of travel of the field and the other in the direction of the lines of magnetic flux.

Reagent refers broadly to any chemical or biochemical agent used in a reaction, including enzymes. A reagent can include a single agent which itself can be monitored (e.g., a substance that is monitored as it is heated) or a mixture of two or more agents. A reagent may be living (e.g., a cell) or non-living. Exemplary reagents for a nucleic acid amplification reaction include, but are not limited to, buffer, metal ion (for example magnesium salt), chelator, polymerase, primer, template, nucleotide triphosphate, label, dye, nuclease inhibitor, and the like. Reagents for enzyme reactions include, for example, substrates, chromogens, cofactors, coupling enzymes, buffer, metal ions, inhibitors and activators. Not all reagents are reactants.

Detergent: Includes anionic, cationic, zwitterionic and nonionic surfactants.

Robustness: refers to the relative tolerance of an assay format to variability in execution, to materials substitutions, and to interferences, over a range of assay conditions. Robustness generally increases with the strength of the detection signal generated by a positive result. Robustness negatively correlates with the difficulty and complexity of the assay.

Specificity: Refers to the ability of an assay to reliably differentiate a true positive signal of the target biomarker from any background, erroneous or interfering signals.

Sensitivity: Refers to the lower limit of detection of an assay where a negative can no longer be reliably distinguished from a positive.

Stability: during storage, any compositional change measured in a parameter, for example activity, concentration, degradation, viscosity, pH, or particle composition, that is greater than 10% over time, denotes instability. Changes less than or equal to 10% connote stability. The time period over which stability is measured is relative depending on the intended utility of the composition. Accelerated stability at higher temperature is sometimes taken as a more speedy way of extrapolating stability over longer periods of time than are actually measured.

Endpoint: "Endpoint" or "datapoint" is used here as shorthand for a "result" from either qualitative or quantitative assays, and may refer to both stable endpoints where a constant plateau or level of reactant is attained, and to rate reactions, where the rate of appearance or disappearance of a reactant or product as a function of time (i.e., the slope) is the datapoint.

Microfluidic cartridge: a "device", "card", or "chip" with fluidic structures and internal channels having microfluidic dimensions. These fluidic structures may include chambers, valves, vents, vias, pumps, inlets, nipples, and detection means, for example. Generally, microfluidic channels are fluid passages having at least one internal cross-sectional dimension that is less than about 500 µm and typically between about 0.1 µm and about 500 µm, but we extend the upper limit of the range to 600 um because the macroscopic character of the bead suspensions used here have a dramatic effect on the microfluidic flow regime, particularly as it relates to restrictions in the fluid path. Therefore, as defined herein, microfluidic channels are fluid passages having at least one internal cross-sectional dimension that is less than 600 um. The microfluidic flow regime is characterized by Poiseuille or "laminar" flow. The particle volume fraction ($\phi$) and ratio of channel diameter to particle diameter (D/d) has a measurable effect on flow characteristics. (See for example, Staben M E et al. 2005. Particle transport in Poiseuille flow in narrow channels. Intl J Multiphase Flow 31:529-47, and references cited therein).

Microfluidic cartridges may be fabricated from various materials using techniques such as laser stenciling, embossing, stamping, injection molding, masking, etching, and three-dimensional soft lithography. Laminated microfluidic cartridges are further fabricated with adhesive interlayers or by thermal adhesiveless bonding techniques, such by pressure treatment of oriented polypropylene. The microarchitecture of laminated and molded microfluidic cartridges can differ.

Microfluidic channel: also termed "microchannel", is a fluid channel having variable length, but one dimension in cross-section less than 500 um. Microfluidic fluid flow behavior in a microfluidic channel is highly non-ideal and laminar and may be more dependent on wall wetting properties, roughness, liquid viscosity, adhesion, and cohesion than on pressure drop from end to end or cross-sectional area. The microfluidic flow regime is often associated with the presence of "virtual liquid walls" in the channel. However, in larger channels, head pressures of 10 psi or more can generate transitional flow regimes bordering on turbulent, as can be important in rinse steps of assays.

Microchannels constructed of layers formed by extrusion molding may have more rounded channel profiles and a radius on each "via". The internal channel surfaces of injection molded parts are also somewhat smoother. The flow characteristics of the channels are significant because of the profound surface effects in the microflow regime. Surface tension and viscosity compound surface roughness effects. The most narrow dimension of a channel has the most profound effect on flow. It follows that flow in channels that are based on rectangular or circular cross-sectional profiles is controlled by the diagonal width or diameter, and design is typically varied to take advantage of this behavior. Reduction of taper in the direction of flow leads to a wicking effect for diameters below 200 microns. Conversely, flow can be stopped by opening up a channel to form a bulb unless pressure is applied. Vias in a channel can be designed to promote directional flow, a sort of solid state check valve.

Microfluidic pumps: include for example, bulbs, bellows, diaphragms, or bubbles intended to force movement of fluids, where the substructures of the pump have a thicknesses or other dimension of less than 1 millimeter. Such pumps include the mechanically actuated recirculating pumps described in U.S. Pat. No. 6,743,399 to Weigl and U.S. 2005/0106066 to Saltsman, commonly assigned to the applicant. Such pumps may be robotically operated or operated by hand. Electroosmotic pumps are also provided. Such pumps can be used in place of external drives to propulse the flow of solubilized reagents and sample in microfluidic device-based assays.

Bellows Pump: is a device formed as a cavity, often cylindrical in shape, bisected in coronal section by an elastomeric diaphragm to form a first and a second half-chamber which are not fluidically connected. The diaphragm is controlled by a pneumatic pulse generator connected to the first half-chamber. Positive pressure above the diaphragm distends it, displacing the contents of the second half-chamber, negative gauge pressure (suction) retracts it, expanding the second half chamber and drawing fluid in. By half-chamber, it should be understood that the effective area of the diaphragm is the lesser of the volume displacement under positive pressure and the volume displacement under suction pressure, and it thus optimal when the first and second half chambers are roughly symmetrical or equal in volume above and below the diaphragm. The second half-chamber is connected to a fluid in-port and out-port. The fluid in-port and out-port may be separate ports or a single port, but in either case, are under valve control. As described above, a pneumatic pulse generator is pneumatically connected to the first half-chamber, generally by a microchannel, which is also valved. In the complete apparatus, pneumatic actuation is programmable. Thus, programmable pneumatic pressure logic used by the pulse generator has two functions, to actuate the diaphragm on signal, and to open and close valves on signal. When the pulse generator is off-cartridge, nipples or inlets, a pneumatic manifold and solenoid valves are provided.

In use, fluid enters the second half-chamber of a bellows pump through the inlet valve when negative pressure is applied to the diaphragm (or passively, when fluid is pushed in by a second bellows pump). Then, when positive pressure is applied to the diaphragm, the fluid contents of the chamber are displaced out through the outlet valve. Similarly, positive and negative pressure signals control valve opening and closing. By supplying a train of positive and negative pressure pulses to a diaphragm, fluid can be moved in and out of a bellows pump chamber. This fluid motion becomes directional by the application of synchronized valve logic, thus the pumping action.

Pairs of bellows pumps, i.e., "dual bellows pumps", can mix suspensions of beads or particles in fluids when configured with a first diaphragm pressure-actuated and a second diaphragm passive so as to force reciprocating flow between the two bellows chambers after the inlet and outlet valves are closed. Reciprocating flow can also be obtained by synchronously actuating both diaphragms with alternating or inverted pneumatic pulses. Similarly, a multiplicity of bellows pumps can be fluidly connected in series to perform a mixing function.

Microfluidic valves: include a genus of hydraulic, mechanic, pneumatic, magnetic, and electrostatic actuator flow controllers with at least one dimension smaller than 500 um. A representative flap valve of the genus is described in U.S. Pat. No. 6,431,212. Also included are check valves. One class of valves refers to a configuration in which a flow channel and a control channel intersect and are separated by an elastomeric membrane that can be deflected into or retracted from the flow channel in response to an actuation force in the control channel. Patents describing species of microfluidic valves include U.S. Pat. Nos. 5,971,355, 6,418, 968, 6,518,99, 6,620,273, 6,748,975, 6,767,194, 6,901,949, and U.S. Patent Application 2002/0195152 and 2005/02005816, several of which are commonly assigned to the applicant, and all of which are incorporated herein by reference.

Check valve: is a one way valve. Microscale versions of ball-spring, flap, and flip-flop valves are check valves.

Passive shut-off valves: are wettable inserts or coatings in microfluidic channels that swell when immersed, closing the microchannel off to further flow in either direction. Analogously, "surface tension valves" consisting of a ring of hydrophobic material on the walls of a microchannel have been disclosed to delay or stop the flow of a reagent. Stop flow can also be achieved by widening the taper of a microfluidic channel diameter.

Self-priming: connotes a microfluidic channel that is fabricated from a material or is treated so that the channel is wettable and capillary flow begins generally without the need to prime the channel.

Via: A step in a microfluidic channel that provides a fluid pathway from one substrate layer to another substrate layer above or below, characteristic of laminated devices built from layers.

"Air ports" refer to the arms of a pneumatic manifold under programmable control of external servomechanisms. The pneumatic manifold may be charged with positive or negative gauge pressure. Operating pressures of ±5 to 10 psig have been found to be satisfactory.

Squeeze bulbs: are micro-"basting" devices that, when squeezed, serve to generate a hydraulic pressure head in a microfluidic device and to promote mixing, and may be made of polyurethane, for example.

Pillow: an on-board reagent pack formed from a deformable sacculus, for example a mylar microbag, optionally enclosed in a pneumatically actuated device for puncturing to bag to release its contents at a controlled time. Co-laminates of a metal and a plastic are preferred for stability considerations.

Blister pack: an on-board reagent pack under a deformable (or elastic) diaphragm. Used to deliver reagents by pressurizing the diaphragm and may appose a "sharp", such as a metal chevron, so that pressure on the diaphragm ruptures the "pillow" (see pillow). These may be used with check valves or closable vents to produce directional fluid flow and reagent delivery. Elastic diaphragms are readily obtained from polyurethane, polysilicone and polybutadiene, and nitrile for example (see elastomer). Deformable, inelastic diaphragms are made with polyethylene terephthalate (PET), mylar, polypropylene, polycarbonate, or nylon, for example. Other suitable materials for the deformable film include parafilm, latex, foil, and polyethylene terephthalate. Key factors in selecting a deformable film include the yield point and the deformation relaxation coefficient (elastic modulus).

Use of these devices permits delivery or acceptance of a fluid while isolating the contents of the microfluidic device from the external environment, and protecting the user from exposure to the fluid contents.

Isolation or "isolated": "Forward isolation" refers here to protection of the user from exposure to clinical materials potentially contaminated with an infectious agent or toxin. "Reverse isolation" refers to protection of the assay device from spurious exogenous contamination, such as with a nucleic acid, that may cause false positives.

Single entry: refers to a microfluidic device, card or cartridge that requires, or permits, only a single introduction of sample, and the assay is then conducted within a self-contained, sealed system. Such devices optionally contain a device for sealing or locking the sample port and an on-board means for disinfecting the contents of the device and any waste following completion of the assay. In one embodiment, the device can be discarded after use without special precautions.

Waste chamber or "pack": is a cavity or chamber that serves as a receptacle for sequestering discharged sample, rinse solution, and waste reagents. Typically also includes a wicking material (see wick). Waste packs may also be sealed under an elastic isolation membrane sealingly attached to the body of the microfluidic device. This inner membrane expands as the bibulous material expands, thus enclosing the waste material. The cavity outside the isolation membrane is vented to atmosphere so that the waste material is contained and isolated. Waste packs may optionally contain dried or liquid sterilants.

Wick: is a bibulous material used to propulse fluid flow by capillary wetting in place of, or in concert with, microfluidic pumps. The bibulous core typically includes a fibrous web of natural or synthetic fibers, and also often includes certain absorbent gelling materials usually referred to as "hydrogels," "superabsorbent" or "hydrocolloid" materials. Materials include papers, sponges, diaper materials, Contec-Wipe, and others. Dessicants may also be used, such as calcium sulfate, calcium sulfate, silica gel, alone or in combination with bibulous materials.

Trap: a fluid trap with dam that further isolates a waste reservoir from a vent.

Vent: a pore intercommunicating between an internal cavity and the atmosphere. A "sanitary" or "isolation vent" also contains a filter element that is permeable to gas, but is hydrophobic and resists wetting. Optionally these filter elements have pore diameters of 0.45 microns or less. These filters function both in forward and reverse isolation. Filter elements of this type and construction may also be placed internally, for example to isolate a valve or bellows pump from the pneumatic manifold controlling it.

Test field: refers to the site in the microfluidic device-based assay where the assay endpoint is observed or measured, such as an optical window, and is optionally a detection chamber containing test pads.

Nucleic Acid Target Capture Assembly refers to a combination of a solid phase nucleic acid affinity binding substrate and a means for positioning the binding substrate in the fluid path of a microfluidic device. Binding substrates include filters, beads, frits, fluidized beds, and solid surfaces in general. Materials include silica, derivatized silica, alumina, zirconia, treated latex beads, and the like. Means for positioning can be as simple as direct deposition of beads in a microfluidic channel, or more complex such as by mounting a filter membrane or frit in the fluid path of the channel. A filter membrane can be inserted in a cutout in a layer, can be glued in place, can be fitted in place in the manner of a filter plug, or can be contained in a pre-assembled housing and pressure fitted in place. A frit is generally pressure fitted or etched in place.

Elastomer: In general, elastomers deform when force is applied, but then return to their original shape when the force is removed. The elasticity exhibited by elastomeric materials can be characterized by a Young's modulus. Elastomeric materials utilized in the microfluidic devices disclosed herein typically have a Young's modulus of between about 1 Pa-1 TPa, in other instances between about 10 Pa-100 GPa, in still other instances between about 20 Pa-1 GPa, in yet other instances between about 50 Pa-10 MPa, and in certain instances between about 100 Pa-1 MPa. Elastomeric materials having a Young's modulus outside of these ranges can also be utilized depending upon the needs of a particular application.

Some microfluidic devices described herein are fabricated from an elastomeric polymer such as polyisoprene, polybutadiene, polychlorophene, polyisobutylene, poly(styrene-butadiene-styrene), nitriles, the polyurethanes and the polysilicones. GE RTV 615, a vinyl-silane crosslinked (type) silicone elastomer (family), and polydimethysiloxane (PDMS) membrane available HT-6135 and HT-6240 membranes from Bisco Silicons (Elk Grove, Ill.) are useful in selected applications. The choice of materials typically depends upon the particular material properties (e.g., solvent resistance, stiffness, gas permeability, and/or temperature stability) required for the application being conducted. Additional elastomeric materials that can be used in the manufacture of the components of the microfluidic devices described in Unger et al 2000 Science 288:113-116. Some elastomers of the present devices are used as diaphragms and in addition to their stretch and relax properties, are also selected for their porosity, impermeability, chemical resistance, and their wetting and passivating characteristics. Other elastomers are selected for their thermal conductivity. Micronics Parker Chomerics Thermagap material 61-02-0404-F574 (0.020" thick) is a soft elastomer (<5 Shore A) needing only a pressure of 5 to 10 psi to provide a thermal conductivity of 1.6 W/m-° K.

Deformable films, lacking elasticity, are also used in the microfluidic devices of the invention.

Lateral flow Assay: refers to a class of conventional assays wherein particle aggregation, agglutination or binding is detected by applying a particle-containing fluid to a fibrous layer such as a permeable membrane and observing the chromatographic properties as the particles and particle aggregates move into and through the material. Penetration of clumps of particles is impeded, whereas free particles penetrate between the fibers. Similarly, free particles may accumulate as clumps in zones of the fibrous layer treated with affinity binding agents. The devices and methods described here are not lateral flow assays.

"Conventional" is a term designating that which is known in the prior art to which this invention relates.

"About" and "generally" are broadening expressions of inexactitude, describing a condition of being "more or less", "approximately", or "almost" in the sense of "just about", where variation would be insignificant, obvious, or of equivalent utility or function, and further indicating the existence of obvious minor exceptions to a norm, rule or limit.

Herein, where a "means for a function" is described, it should be understood that the scope of the invention is not limited to the mode or modes illustrated in the drawings alone, but also encompasses all means for performing the function that are described in this specification, and all other means commonly known in the art at the time of filing. A "prior art means" encompasses all means for performing the function as are known to one skilled in the art at the time of filing, including the cumulative knowledge in the art cited herein by reference to a few examples.

Means for extracting: refers to various cited elements of a device, such as a solid substrate, filter, filter plug, bead bed, frit, or column, for capturing target nucleic acids from a biological sample, and includes the cumulative knowledge in the art cited herein by reference to a few examples.

A means for polymerizing, for example, may refer to various species of molecular machinery described as polymerases and their cofactors and substrates, for example reverse transcriptases and TAQ polymerase, and includes the cumulative knowledge of enzymology cited herein by reference to a few examples.

Means for Amplifying include thermocycling and isothermal means. The first thermocycling technique was the polymerase chain reaction (referred to as PCR) which is described in detail in U.S. Pat. Nos. 4,683,195, 4,683,202 and 4,800, 159, Ausubel et al. Current Protocols in Molecular Biology, John Wiley and Sons, Baltimore, Md. (1989), and in Innis et al., ("PCR Protocols", Academic Press, Inc., San Diego Calif., 1990). Polymerase chain reaction methodologies are well known in the art. Briefly, in PCR, two primer sequences are prepared that are complementary to regions on opposite complementary strands of a target sequence. An excess of deoxynucleoside triphosphates are added to a reaction mixture along with a DNA polymerase, e.g., Taq polymerase. If the target sequence is present in a sample, the primers will bind to the target and the polymerase will cause the primers to be extended along the marker sequence by adding on nucleotides. By raising and lowering the temperature of the reaction mixture, the extended primers will dissociate from the template to form reaction products, excess primers will bind to the template and to the reaction products and the process is repeated. By adding fluorescent intercalating agents, PCR products can be detected in real time.

One isothermal technique is LAMP (loop-mediated isothermal amplification of DNA) and is described in Notomi, T. et al. Nucl Acid Res 2000 28:e63.

strand Displacement Amplification (SDA) is another method of carrying out isothermal amplification of nucleic acids which involves multiple rounds of strand displacement and synthesis, i.e., nick translation (Walker et al. Nucleic Acids Research, 1992: 1691-1696). A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Another nucleic acid amplification technique is reverse transcription polymerase chain reaction (RT-PCR). First, complementary DNA (cDNA) is made from an RNA template, using a reverse transcriptase enzyme, and then PCR is performed on the resultant cDNA.

Another method for amplification is the ligase chain reaction ("LCR"), disclosed in EPO No. 320 308. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qβ Replicase, may also be used as still another amplification method in the present invention. In this method, a replicative sequence of RNA that has a region complementary to that of a target is added to a sample in the presence of an RNA polymerase. The polymerase will copy the replicative sequence that can then be detected.

Still further amplification methods, described in GB Application No. 2 202 328, and in PCT Application No. PCT/US89/01025, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989, Proc. Natl. Acad. Sci. U.S.A., 86: 1173; Gingeras et al., PCT Application WO 88/10315). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNAs are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPO No. 329 822 disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase D, resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al. in PCT Application WO 89/06700 disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M. A., In: "PCR Protocols: A Guide to Methods and Applications", Academic Press, N.Y., 1990; Ohara et al., 1989, Proc. Natl. Acad. Sci. U.S.A., 86: 5673-567).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989, Genomics 4: 560).

Means for detecting: as used herein, refers to an apparatus for displaying an endpoint, i.e., the result of an assay, and may include a detection channel and test pads, and a means for evaluation of a detection endpoint. Detection endpoints are evaluated by an observer visually in a test field, or by a machine equipped with a spectrophotometer, fluorometer, luminometer, photomultiplier tube, photodiode, nephlometer, photon counter, voltmeter, ammeter, pH meter, capacitative sensor, radio-frequency transmitter, magnetoresistometer, or Hall-effect device. Magnetic particles, beads and microspheres having or impregnated color or having a higher diffraction index may be used to facilitate visual or machine-enhanced detection of an assay endpoint. Magnifying lenses in the cover plate, optical filters, colored fluids and labeling may be used to improve detection and interpretation of assay results. Means for detection of magnetic particles, beads and microspheres may also include embedded or coated "labels" or "tags" such as, but not limited to, dyes such as chromophores and fluorophores; radio frequency tags, plasmon resonance, spintronic, radiolabel, Raman scattering, chemoluminescence, or inductive moment as are known in the prior art. Colloidal particles with unique chromogenic signatures depending on their self-association are also anticipated to provide detectable endpoints. QDots, such as CdSe coated with ZnS, decorated on magnetic beads, or amalgamations of QDots and paramagnetic $Fe_3O_4$ microparticles, optionally in a sol gel microparticulate matrix or prepared in a reverse emulsion, are a convenient method of improving the sensitivity of an assay of the present invention, thereby permitting smaller test pads and larger arrays. Fluorescence quenching detection endpoints are also anticipated. A variety of substrate and product chromophores associated with enzyme-linked immunoassays are also well known in the art and provide a means for amplifying a detection signal so as to improve the sensitivity of the assay. Detection systems are optionally qualitative, quantitative or semi-quantitative. Visual detection is preferred for its simplicity, however detection means can involve visual detection, machine detection, manual detection or automated detection.

Means for heating and cooling: A number of means for thermocycling a liquid filled chamber have been described in the prior art. These prior art means include convective and conductive heating elements such as electroresistors, hot air, lasers, infrared radiation, Joule heating, TEC or Peltier devices, heat pumps, endothermic reactants, and the like, generally in conjunction with a heat sink for dissipating heat during chill-down parts of the cycle. Heating means may also include heating by the motion of magnetic beads driven by a high frequency magnetic field.

Heating and cooling devices for thermocycling fall into two categories: ramped and fixed temperature. Fixed temperature devices maintain a relatively constant temperature in a reaction, and at least two reaction chambers are needed for thermocycling. Ramped heating devices will vary the temperature between at least two set points, and therefore only one reaction chamber is required for thermocycling. Combinations of heating elements are possible. Peltier devices may be used for both fixed temperature and ramped applications. Water baths are not well adapted to ramped temperature control for thermocycling.

Generally, heating and cooling means interface with a fluidics member so as to effect heat exchange with the liquid contents. For PCR, the relevant elements forming the microfluidic channels or chambers where heat exchange takes place are termed as part of the "PCR fluidics and thermal interface" assembly.

Means for isolating include impermeable cartridge body, gas permeable hydrophobic venting, bibulous padding in waste chamber, disinfectant in waste chamber, elastomeric membrane separating pneumatic actuator from blister pack, valve with elastomeric membrane actuated by suction pressure, suction pressure in said sample entry port, rubberized nipple in sample entry port, snap-lock closure over sample entry port, on-board reagent pack, and single-entry sample port.

Unless the context requires otherwise, throughout the specification and claims which follow, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

2. Detailed Description

The assays of the present invention have three stages: extraction, amplification, and detection. The microfluidic devices disclosed here are formed from three fluidic subcircuits corresponding to these functions integrated together in a single device.

Referring now to the figures, FIG. 1 is a schematic of a microfluidic subcircuit 100 for sample processing and nucleic acid extraction. Sample, for example stool, urine, whole blood or plasma, can be fluid, solid or a mixture of both. In one embodiment, fluid sample is pipetted or drawn into a liquid sample port. In another embodiment, sample is first fluidized and then introduced into a liquid sample port. In another embodiment, a swab having the material of interest is inserted into a chamber within the device; the neck of the swab is then broken off, and the device is sealed (as in FIG. 27). Pretreatment is envisaged when necessary.

Following introduction of the sample into the device, in the integrated devices of the invention, the remaining assay steps are automated or semi-automated. The device contains safeguards to prevent operator exposure to biohazardous material after the device is sealed.

A bellows pump and associated check valves is optionally used to effect fluid transport. Capillary action or wicking may also be used.

To remove vegetable, mucous, and unwanted particulate matter, fluidized sample is optionally pre-filtered through a depth filter, for example made of polypropylene fibers, and then mixed with lysis buffer, to release the target nucleic acid contents from associated debris and contaminants. Optionally, the prefilter may be used to separate the cellular and plasma components of blood.

Lysis buffer in the lysis buffer pouch contains a chaotrope in combination with a detergent to reduce associations between nucleic acids and adherent molecules, and optionally contains a nuclease inhibitor and chelator such as EDTA to reduce nucleic acid degradation prior to wash.

We have used 4.5M guanidinium thiocyanate (GSCN), in combination with detergents such as sarcosine and Triton X-100, with weakly acidic buffer, to remove sufficient hemoglobin from whole blood so as to render the nucleic acid suitable for PCR. The method is also successful with stool. Gram negative bacteria are lysed with this treatment.

Mixing of the sample and the lysis buffer at the microscale requires ingenuity. Adaptation of biochemistry to microscale fluid reactors has required novel engineering. In our experience, for example, a preferred mixing mechanism in the microfluidic devices of the present invention is a reduction in one cross-sectional dimension of a channel so as to approach expected diffusional path lengths at achievable linear flow velocities. Generally this is done in laminated or molded devices by holding microfluidic channel width constant and reducing the depth of the channel from about 75 microns (3 mil) to about 25 microns (1 mil). The practice ensures that macromolecules and solutes adequately mix over a predictable length of microchannel at manageable head or suction pressures ($\Delta P$) of generally less than or equal to $\pm 10$ psig. Pneumatic actuators are provided so as to permit refluxing solution between the lysis chamber and the lysis buffer pouch. Elastomeric membranes ensure forward and reverse isolation.

The lysate is then passed through a nucleic acid target capture assembly, which has non-specific, reversible affinity for nucleic acids. The target capture material is generally an electropositive hydrophilic material, typically also rich in hydroxyl groups. Suitable target capture materials are described in U.S. Pat. No. 5,234,809, which is incorporated herein in full by reference. The target capture assembly may be, for example, a silica surface, a fiber matrix or filter composed of materials such as silica, a bed of silica or aluminum oxide beads, a fritted plug of derivatized zirconium, and the like, adapted to the dimensions, hydrostatic pressures, and flow rates of a microfluidic device. Beads may be coarse or fine, but are preferably generally homogeneous in size. Fibers may be coarse or fine, and loosely packed or tightly packed, as is required to obtain the necessary surface to volume ratio, flow rate and acceptable pressure drop. Means for sealing the fiber pad to the walls of a microfluidic chamber include rabbet or mortise construction, gasket or adhesive as sealant, plastic solvent or sonic welding, pressure fit, or elements of prepackaged modular construction that can be snap fit into place so that all fluid must egress through the filter bed. For membrane filters, supporting ribs may be microfabricated with a laser.

Following discharge of the lysate from the nucleic acid target capture assembly to waste under control of a valve, the retentate is then rinsed with wash reagent from the solvent wash pouch, and the wash reagent is also discharged to waste under valve control. Wash reagent can consist of anhydrous ethanol, 70% to 95% ethanol in water, acetone, or acetone, ethanol, water mixtures, optionally with buffer. The solvent is stored on-board in a foil-lined "blister pack", which is punctured at a programmed time under pneumatic control, so that the contents wash the nucleic acid target capture assembly retentate and pass to waste. Wash reagent removes lipids, EDTA and salts not compatible with PCR amplification, while precipitating nucleic acids. After the wash rinse is completed, the target capture material is briefly dried under a stream of sterile filtered air to remove residual ethanol or acetone.

Following satisfactory washing, the nucleic acid retentate is eluted from the target capture member with elution buffer from the elution buffer pouch. "Slug elution" is one procedure that optimizes recovery through use of the chamber diaphragm so that elution buffer flows back and forth over the target capture member before passing into the amplification subcircuits as will be shown in FIG. 2.

This procedure yields nucleic acids that can be used in PCR immediately, without the need for intermediate isolation (or purification) as was a drawback of earlier procedures. The elution buffer, containing target nucleic acids, is used directly to rehydrate a dried "PCR mix" containing reagents and enzymes, whereupon PCR is commenced. Other means for amplification are also contemplated.

Serendipitously, elution in the target capture assembly shears high molecular weight genomic DNA into fragments more suitable for PCR, an added advantage in detecting low copy number targets. And because the process takes place entirely within the closed device, there is essentially no risk of contamination following sample input.

By using the eluate itself as the rehydration medium for the dehydrated PCR mix in the amplification subcircuits, target sequences are not further diluted.

Accordingly, elution buffer, by design, serves as PCR buffer. Elution buffer is designed to be bifunctional, and seamlessly integrates sample preparation and PCR amplification in a way not previously attempted at the microscale.

Amplification

Amplification by PCR is a cycle of denaturation, annealing, and extension, as is well known in the art.

Figure 2:
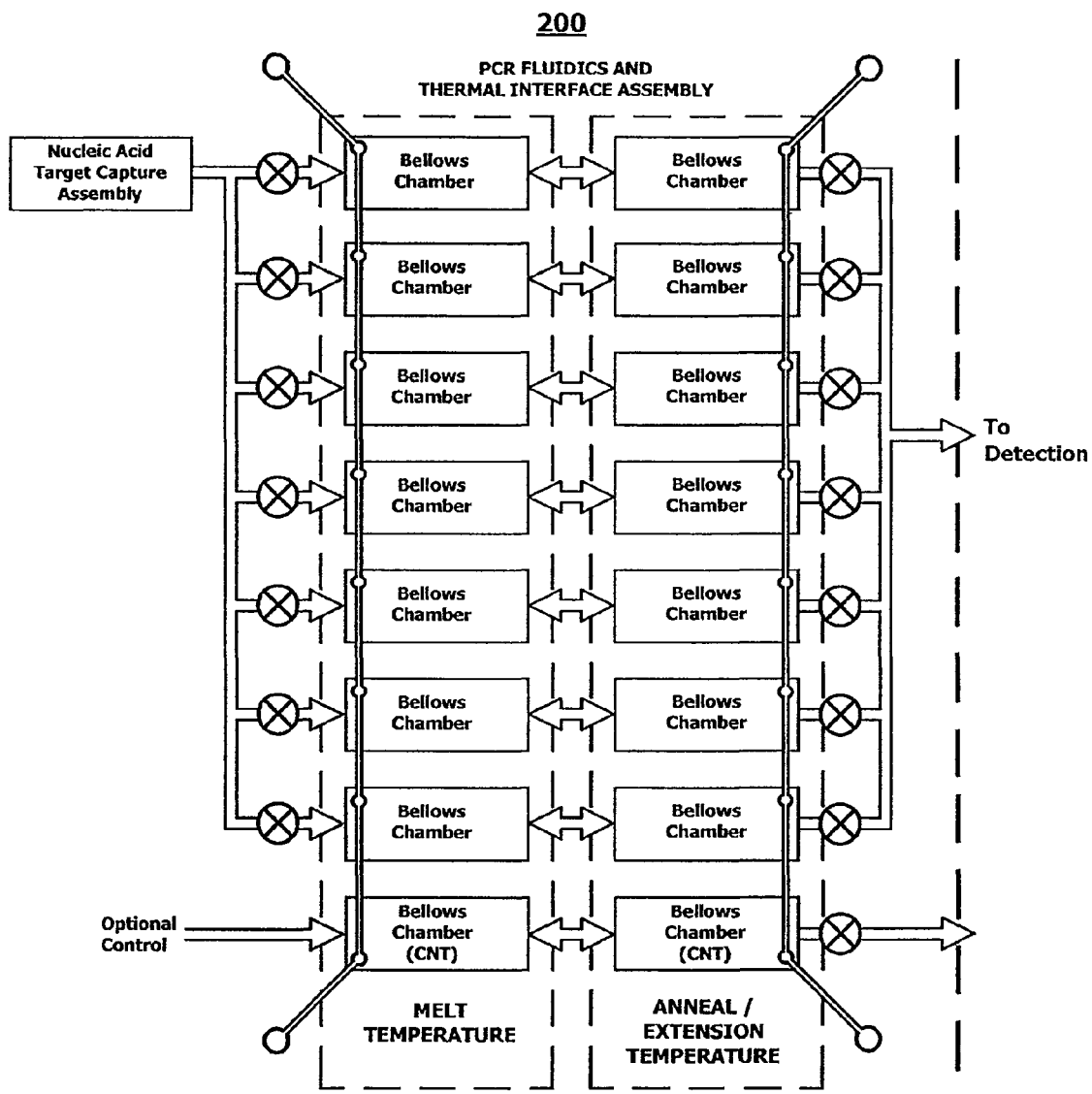
FIG. 2 is a schematic of a PCR amplification microfluidic subcircuit with variable temperature thermal interface.

Turning now to FIG. 2, the nucleic acid eluate is transported through microfluidic channels by ganged valves under pneumatic control into one or more channels or chambers for amplification. This part of the amplification subcircuit makes up the "PCR fluidics and thermal interface" 200, and is designed to optimize heat exchange and mixing. In the amplification channels or chambers, the eluate serves to rehydrate pre-spotted, dehydrated PCR mix. PCR mix includes an optimized concentration of a magnesium salt selected from magnesium acetate, chloride, sulfate, or the like, as is required for polymerase activity, a buffer for optimal pH, and surface active agents. The dehydrated reagents optionally include sodium chloride and sodium citrate matched to the melt curves of the primers to be used in the PCR reaction. Simultaneously, reagents and control template in the control amplification channel (which does not receive sample) are rehydrated with elution buffer directly from the elution buffer chamber. This negative control chamber is used to check for nucleic acid contamination in the device.

In our experience, mixing is not required to rehydrate the PCR reagents. Heating causes convective mixing in the amplification channel or chamber, which vigorously dissolves and distributes the reagents and matrix. Passivation of the amplification subcircuits is accomplished by pretreatment and by incorporation of suitable passivating substances in the dried PCR mix.

The embodiment of FIG. 2 contains two chambers within each arm of the PCR fluidics and thermal interface assembly. These are associated with separate temperature requirements for thermocycling in the PCR protocol. In subsequent examples, other configurations will be illustrated.

The assay device as depicted in FIG. 2 calls for two TEC blocks in thermal contact with the amplification channel or chamber, with fixed temperature control. One block is associated with a bellows pump which serves as a chamber for melting double stranded templates and dissociating primers, and the other for annealing and polymerase extension. Control for the temperature blocks is generally handled off-device and is integrated with control of the pneumatics. Other means for heating and cooling are well known in the art.

The temperature may be fixed or ramped, depending on the design of the PCR fluidics and thermal interface assembly. Assay devices with fixed temperature stations are conceived. Thermocycling with two or three temperature stations, each with a different fixed temperature, accomplishes denaturation, annealing and extension by either cycling the PCR reaction mix between temperature stations back and forth or by circular fluid flow. Single station thermocycling is also contemplated.

It should be noted that the optimal temperature for extension of primers with native TAQ polymerase is about 72° C., but it is known in the art that extension also occurs in PCR thermocycling if a separate 72° C. incubation is not used. The temperature of the annealing chamber can be set between 20 and 85° C. degrees, more preferentially between 50 and 80° C., and most preferentially between 55 and 75° C., depending on salt concentration and primer sequence, and the denaturation chamber is conventionally set at about 95° C., more preferentially at 96 to 100° C., to obtain complete melting and dissociation of the double stranded templates and primers. Complete cycle times of under a minute are readily obtained. Cycle times of less than 30 sec have been routinely demonstrated.

Figure 3:
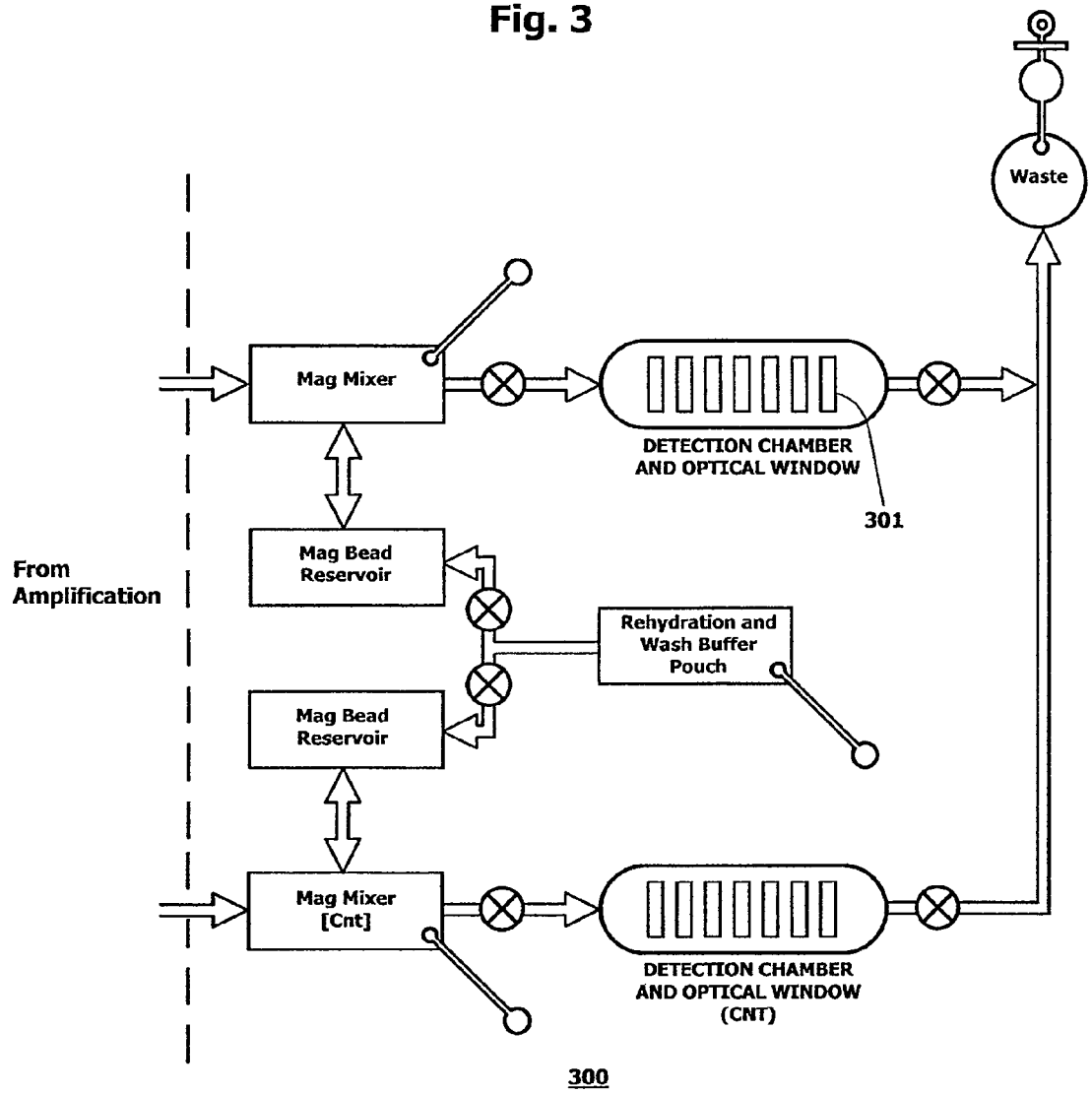
FIG. 3 is a schematic of a microfluidic target detection subcircuit.

Valves under ganged pneumatic control are used to direct flow from the PCR fluidics to the detection subcircuits of FIG. 3. It can thus be seen that there are two primary classes of pneumatic control elements. These comprise diaphragm—both of which are provided with pneumatic interconnects for connection to an external controllable pneumatic actuation manifold. Both classes pneumatic control elements are similar in construction, comprising a liquid inlet, a liquid outlet, and an elastomeric diaphragm separating liquid from the pneumatic interconnect, and differ in that the valves comprise a dam separating the liquid inlet from the liquid outlet and the bellows chambers are open so that the diaphragm when extended fills the chamber and expels the liquid, and when retracted from the chamber by suction pressure in the pneumatic interconnect, draws in the liquid. Thus both classes of elements serve to control the steps of the automated assay. The pneumatic control elements may be ganged for simplicity of control or may be operated independently by design of the valve logic and pneumatic interconnect circuitry. The pneumatic interconnect circuitry is thus oftimes complex, requiring extensive design and experimentation.

Detection by Magnetic Capture Beads

Turning now to the FIG. 3 schematic, a detection subcircuit 300 is shown. The amplification products are first mixed with magnetic capture beads in the mag mixing chamber. These beads are stored in the mag bead reservoir chambers until use. The beads are coated with avidin or other capture agent. Avidin for example will capture biotin-conjugated primers and two-tailed amplicons. Anti-digoxigenin will capture digoxigenin-conjugated primers and two-tailed amplicons.

The magnetic capture beads are typically stored in a dried form and are reconstituted with rehydration and wash buffer from the rehydration and wash buffer pouch before mixing with the amplification products. Bead-bound capture agent is in excess, and both unextended and extended ligand-labeled primers are bound by the beads. Rehydration and mixing is under the control of valves.

The size of magnetic beads preferred in the assay are about 0.01 to 50 microns, more preferably 0.5 to 10 microns, and most preferentially 0.8 to 2.8 microns, mean diameter. Homogeneously sized beads are preferred. Suitable beads may be obtained from Dynal Invitrogen (Carlsbad Calif.), Agencourt Bioscience Corp (Beverly Mass.), Bang's Laboratories, Inc. (Fishers Ind.), Polysciences, Inc (Warrington Pa.), Bioscience Beads (West Warwick R.I.), Bruker Daltonics (Nashville Tenn.) and AGOWA (Berlin Del.), for example.

Following mixing of the magnetic capture beads and the amplification products, the reaction mixture is moved into a detection chamber as shown in FIG. 3. Flow control is provided hydraulically with bellows pumps, or is driven by moving the beads (which are paramagnetic) in a magnetic field. The detection chamber contains test pads 301 coated with antibody against peptide hapten tags on the amplicon as will be described with respect to FIGS. 5 and 26. Further description of a selected embodiment of a detection chamber containing test pad strips is provided with FIGS. 21 and 22. The detection chamber is typically provided with an optical window for visual or machine observation of detection events.

A separate detection channel or chamber for a negative control is optionally provided, because the detection of any amplicons in the negative control reaction would invalidate the assay and indicate contamination of the device or reagents. A positive control may also be provided.

In the detection channel or chamber, the magnetic capture beads and captive amplicons, after optional rinse to waste, are contacted with an array, strip or matrix of test pads 301 having defined geometry. The test pads were treated to immobilize capture antibody or antibodies prior to assembly of the device, for example, on polystyrene, by low pressure gas plasma treatment of plastic areas delimited by a mask, followed by application of the antibody and drying.

In a preferred embodiment, the beads are directed to the test pad surface by the magnetic field and provide a close encounter with the antibody or capture agent. This promotes binding interaction between the hapten and the antibody, so that binding occurs very rapidly without the need for extended incubation. Once bound, the magnetic field is turned off and the test pads are readily washed to remove residual unbound particles.

In practice, the time from amplification to data presentation is less than 4 minutes. Magnetic fields include, conveniently, permanent magnets and electromagnets.

In another preferred embodiment, magnetic bead capture for detecting nucleic acid amplicons permits the design of a detection station with multiple test pads. The capture chamber or channel may contain a panel of test pads (see FIG. 21), each addressable in a "multiplex detection format" by a different hapten:anti-peptidyl hapten antibody pair, or by other ligand:capture agent pairs. Multiplexed display of detection results provides an improved level of convenience for the user.

Figure 4:
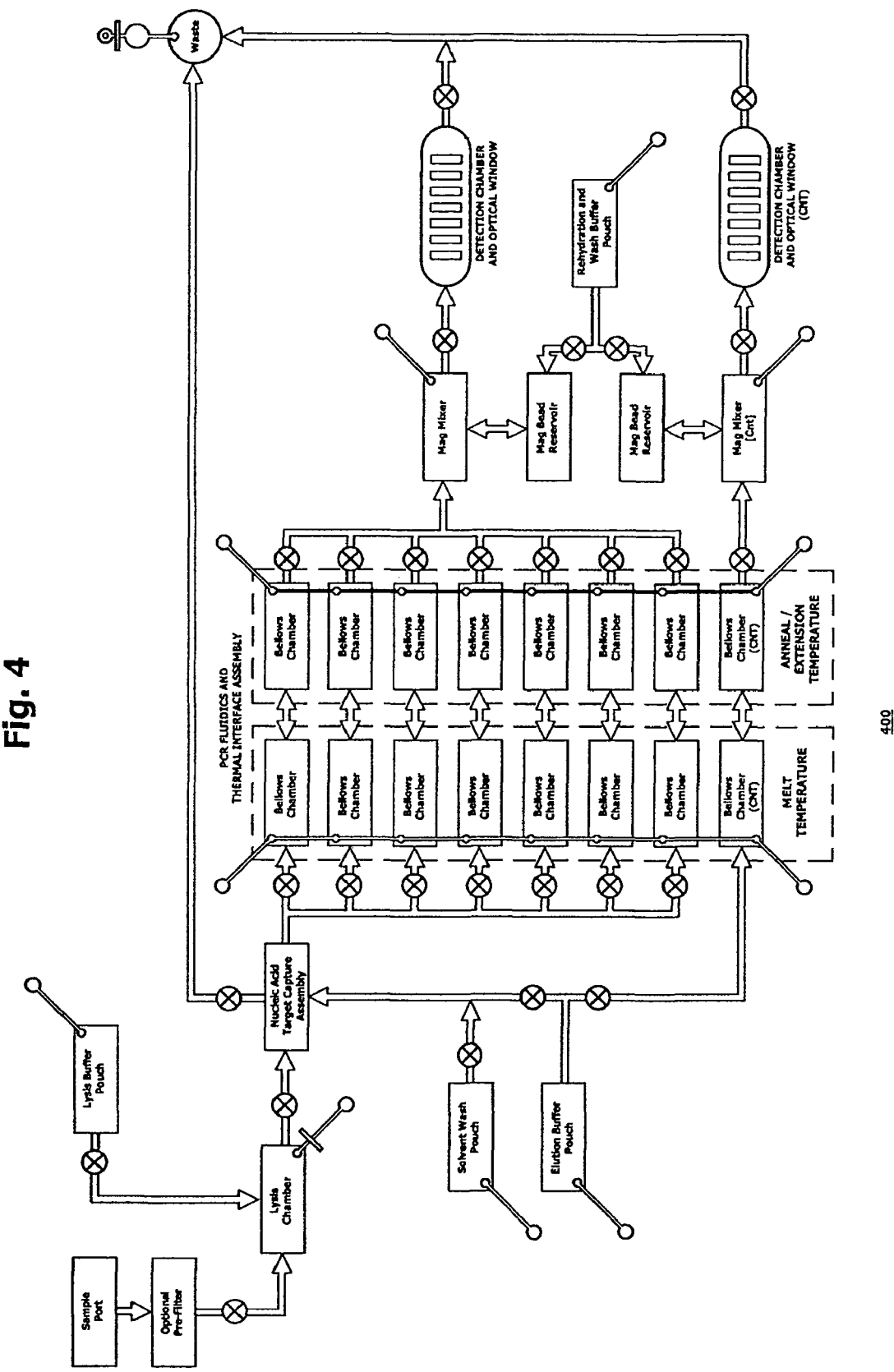
FIG. 4 is a schematic of an integrated device, combining the microfluidic extraction, PCR amplification and detection subcircuits of FIGS. 1, 2, and 3.

FIG. 4 illustrated how the three microfluidic subcircuits, sample extraction 100, target amplification 200, and signal detection 300, are integrated on a single microfluidic card 400. A pneumatic control sequence is used to move fluids. Pneumatic signals are sent to valves, or directly raise or lower diaphragms, transmitting positive or negative pressure to the fluid while keeping the sample isolated.

Also shown in FIG. 4 is the capacity to expand the number of amplification channels, each with one or more separated primer pairs in the PCR mix, and then recombine the products for true multiplex detection at the detection station. In some embodiments, 64 or more amplification channels are provided. More preferred are 16 or fewer channels selected to perform the required differential diagnosis and present the detection event in a visually accessible form. Valves and pumps are ganged on the pneumatic manifold to simplify the command logic. In another embodiment, multiple samples can be analyzed on a single card.

In general, the preferred microfluidic cartridges are comprised of the following elements, a. A sample entry port, a nucleic acid target capture assembly chamber, a lysis buffer chamber, a wash reagent chamber, an elution buffer chamber, a rehydration buffer chamber, a vented waste chamber, a PCR fluidics and thermal interface assembly, a mag mixer chamber, a mag bead reservoir, and a detection chamber; and further comprising, b. A first microchannel fluidically and valvedly interconnecting the sample port and the lysis chamber;

c. A second microchannel fluidly interconnecting the lysis chamber with the nucleic acid target capture assembly chamber;

d. A third microchannel fluidically and valvedly interconnecting the lysis chamber with the lysis buffer pouch chamber;

e. A fourth microchannel fluidically and valvedly interconnecting the nucleic acid target capture assembly chamber and the wash buffer chamber;

f. A fifth microchannel fluidically and valvedly interconnecting the nucleic acid target capture assembly chamber and the elution buffer chamber;

g. A sixth microchannel fluidically and valvedly interconnecting the nucleic acid target capture assembly chamber and at least one PCR fluidics and thermal interface assembly (multiple parallel assemblies are shown in FIG. 4);

h. A seventh microchannel fluidically and valvedly interconnecting at least one PCR fluidics and thermal interface assembly and at least one mag mixer chamber;

i. An eighth microchannel fluidically and valvedly interconnecting at least one mag mixer chamber and the rehydration buffer chamber, the sixth microchannel further comprising a mag bead reservoir interposed between the rehydration buffer chamber and the mag mixer chamber;

j. A ninth microchannel fluidically and valvedly interconnecting the mag mixer chamber and at least one detection chamber;

k. A tenth microchannel fluidically and valvedly interconnecting the nucleic acid target capture assembly chamber and the vented waste chamber;

l. An eleventh microchannel fluidically and valvedly interconnecting the detection chamber and the vented waste chamber; and, further comprising a plurality of internal pneumatic control elements comprising diaphragm-operated valves and bellows chambers, wherein said plurality of internal pneumatic control elements are provided with pneumatic interconnect circuitry for connection to an external controllable pneumatic actuation manifold.

Minor equivalent variants, for example interconnection of the fourth and fifth microchannels (i.e., whereby the lysis buffer and elution buffer share a common pathway to the nucleic acid target capture assembly chamber) would not have a functional effect on device performance. Similarly, the tenth and eleventh microchannels may share a common portal to the waste chamber. Major variants in the layout of the PCR fluidics and thermal interface assembly are possible, and will be discussed below. These include single or multiple interfaces with interfacing reaction chambers on the cartridge. Obviously, other microchannels and functionalities may be added, for example a chamber between the nucleic acid capture assembly and the amplification assembly for use in forming cDNA from mRNA. Other obvious variants include reconfiguring the cartridge for isothermal amplification protocol by eliminating the multi-temperature interface of the PCR fluidics and thermal interface assembly.

More generally, the cartridges comprise:

a. a means for extracting nucleic acids from a biosample;

b. a means for synthesizing amplicons;

c. A means for detecting amplicons; and,

Wherein the means for extracting nucleic acids from a biosample comprises a fluidic subcircuit for extracting nucleic acids from a biosample with solid phase; the means for synthesizing amplicons comprises a fluidic subcircuit for synthesizing amplicons without mixing element; and the means for detecting amplicons comprises a fluidic subcircuit with detection chamber and optical window in a single integrated disposable member, and the fluidics of the single integrated member are controllable by a plurality of pneumatic control elements comprising diaphragm-operated valves and bellows chambers, wherein the plurality of pneumatic control elements are provided with pneumatic interconnect circuitry for connection to an external controllable pneumatic actuation manifold.

In automated or semi-automated configuration, the microfluidic cartridge is inserted into an apparatus (not shown). The apparatus comprises an off-cartridge pneumatic actuation manifold with pneumatic interconnect ports and circuitry for connection to and control of the plurality of valved elements and bellows diaphragms of the microfluidic cartridge. The apparatus is run by a microprocessor with valve logic programming configured to control the pneumatic actuation of the valve and diaphragm elements. The apparatus optionally further has an off-device magnetic field for manipulation of a magnetic microbead reagent, and the magnet is optionally mounted in a movable carriage.

Figure 5:
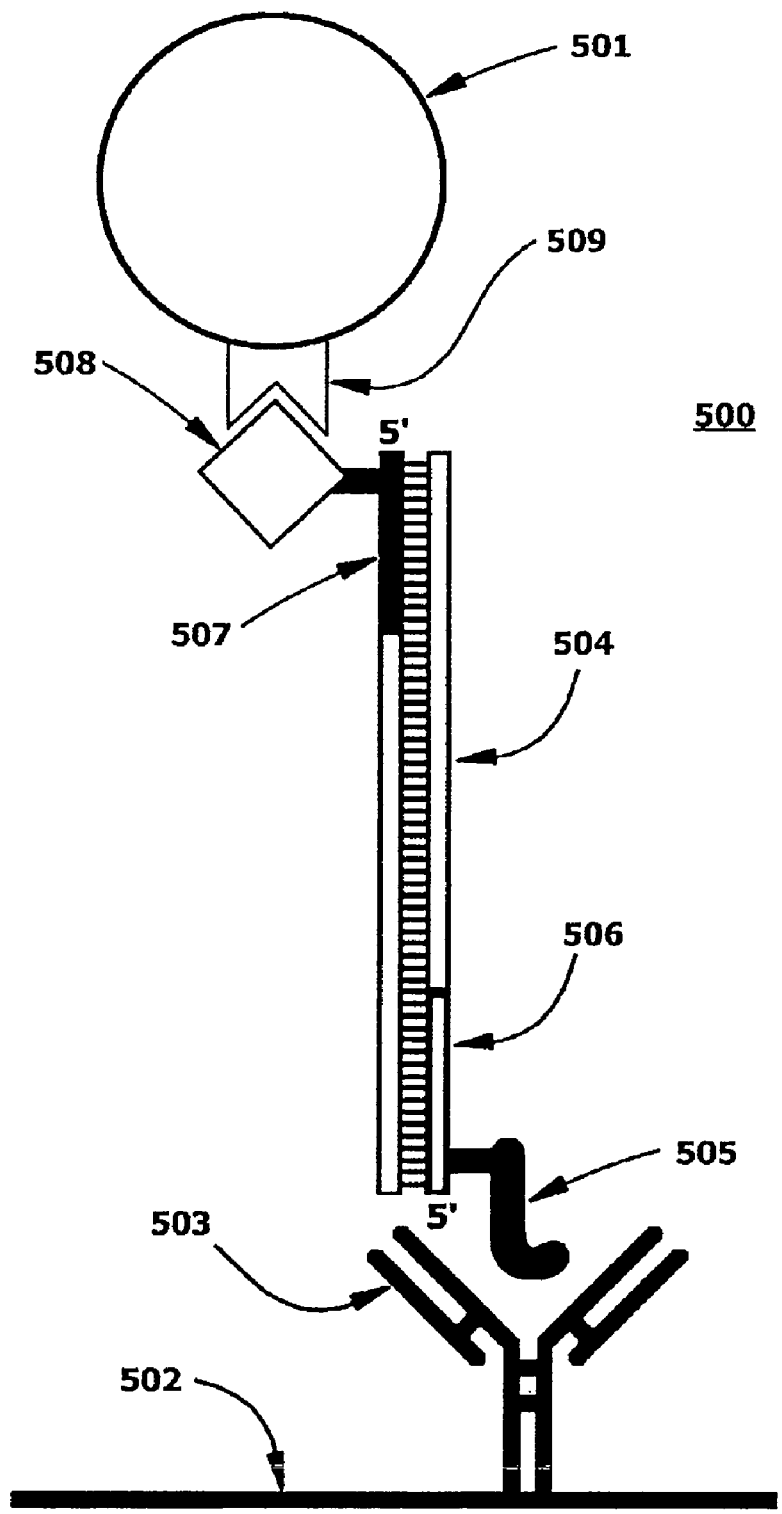
FIG. 5 is a schematic of a positive detection event depicting a two-tailed amplicon and immunommobilization of a magnetic capture bead on a test pad.

A positive target signal molecular detection complex is illustrated in FIG. 5. The molecular detection complex 500 of FIG. 5 depicts a paramagnetic bead 501 immobilized on test pad 502. The tether between bead and capture antibody 503 is formed by a two-tailed amplicon 504, in this case with first primer 506 tagged with peptidyl hapten 6 and second primer 507 tagged with biotin 508, for illustration. The paramagnetic beads are coated with bound avidin 509.

As shown, the immobilized antibody or antibodies on test pad 301 will capture two tailed amplicons. The biotin ligand is captured by an avidin-coated bead, and the magnetic bead or other reporter group in turn is immobilized on the test pad. A sufficient number of immobilized beads, as present in a few microliters of reagent, result in a visual coloration of the test pad. As would be obvious to one skilled in the art, magnetic beads can be prepared with labeling aids such as QDots, dyes, RFIDs, etc, so as to be detectable when immobilized on the respective test pads.

Thus a "positive detection event" results when an amplicon, labeled with a biotin-tailed primer on a first end and a peptidyl hapten-tailed primer on a second end, becomes tethered to a test pad. After release of the magnetic field, those test pads to which magnetic beads are tethered indicate a positive result for that species of peptidyl hapten-tailed amplicon. Those test pads to which no magnetic beads are tethered indicate a negative result for the respective peptidyl hapten-tagged amplicon. Because the species of peptidyl hapten is known, because the antibody is highly specific, and the test pad is assigned to detection of a particular primer sequence, the detection event can be interpreted as positive detection of the particular nucleic acid sequence corresponding to the test pad, and by inference is diagnostic of a pathogen or pathogenic condition.

Figure 6:
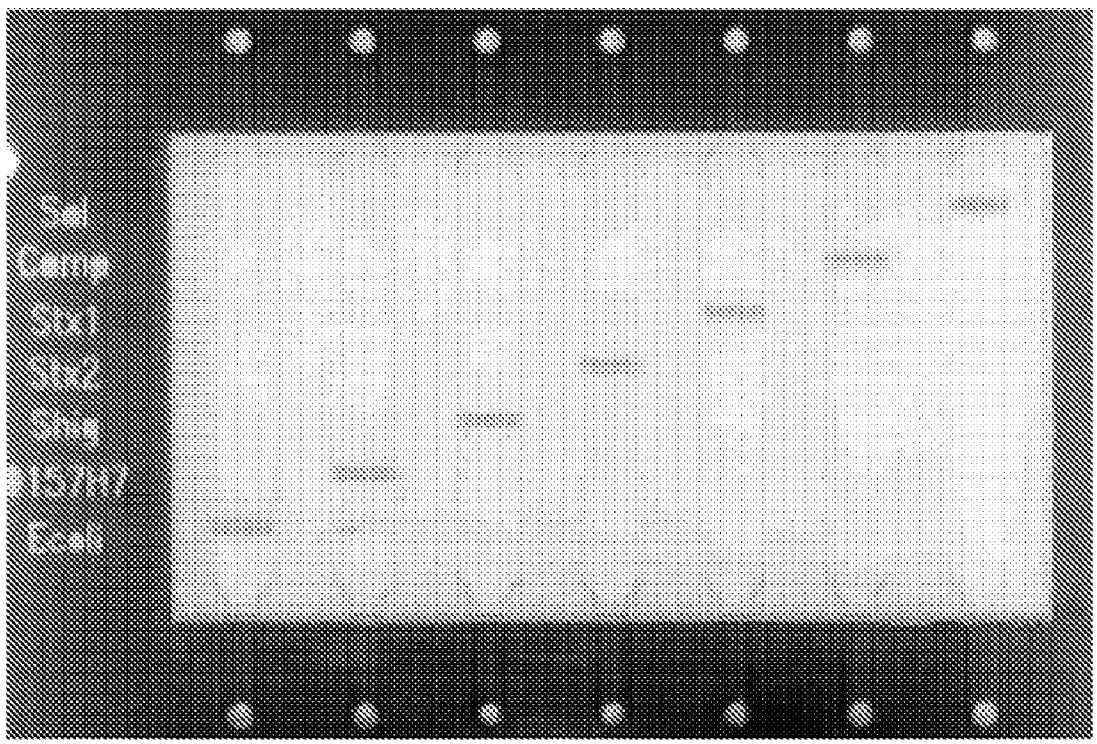
FIG. 6 is a photograph of analytical data for enteric pathogen targets obtained with a device of FIG. 4.

Positive detection events using magnetic beads are easily detected visually as shown in FIG. 6, a significant advantage for any point-of-care assay device or kit of the present embodiment.

In a negative control, typically no two-tailed amplicons will exist absent contamination, so the test pads corresponding to all analytes will remain colorless. As a positive control, a known template may be incorporated in the amplification chamber as a positive control. Because of the discrimination provided by the anti-peptidyl hapten antibodies, the positive control may be an internal control.

FIG. 6 is a photograph of multiple test pad strips mounted in parallel detection chambers. Each strip represents a binding event with a different amplicon formed from primer pairs selected for the enteric pathogens or virulence factors: *Salmonella typhi* (Sal), *Campylobacter jejuni* (Camp), Stx1 (Shiga Toxin 1), Stx2 (Shiga Toxin 2), *Shigella dysenteriae* (Shig), enterohemorrhagic *E coli* O157H7 (marked as 157H7), and a non-pathogenic *E. coli* (Ecoli) as a positive control. Positive reactions are clearly visible without instrumentation.

Figure 21:
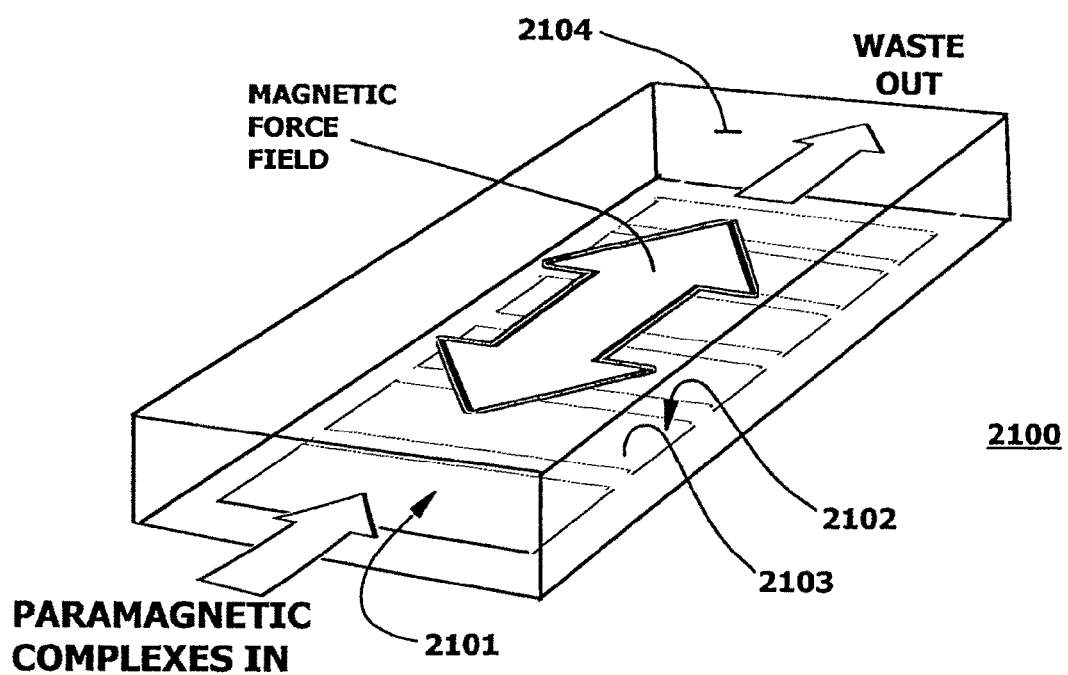
FIG. 21 is a plan view of a multiplex detection chamber and optical window.

The detection station shown in FIG. 6 consists of seven vertical multiplex detection channels mounted in parallel in an optical window. Each channel contains 7 test pad strips, and each test pad is about 2×0.5 mm. A perspective view of a detection channel is shown in FIG. 21. Evident in the photograph is the visual clarity provided by populations of magnetic beads bound to a test pad in the form of the molecular structure described in FIG. 5.

In addition, the engineering of integrated, automatic microfluidic devices of the invention has required the development and improvement of individual microfluidic elements or members. These include microfluidic channels, chambers, valves, valve trees, filters, capture filters, isolation filters, pneumatic manifolds, blister packs (reagent pouches), waste sequestration chambers, sanitary vents, bellows chambers, bellows pumps, thermal heat-exchange interfaces, in-line mixers, on-card wiring, optical windows, test pads, and microchannel-depositions of dehydrated reagents. And also programmable interface elements include pneumatic control manifolds, optical scanners, and movable undercarriages for magnetic beads.

Microfluidic channels preferentially have a rectangular cross-section. Wall roughness is dependent on method of fabrication. A preferred method of fabrication involves lamination of thin sheets, stencil cut with a laser or other cutting device, to build up layers containing fluid and pneumatic circuitry. Microchannels constructed of layers formed by injection molding may have more rounded channel profiles and a radius on each 'via'. The internal channels of injection molded parts are also somewhat smoother.

In the microfluidic flow regime, a virtual wall of bound solvent builds up on the solid substrate, but the thickness of the virtual wall can be reduced in part by passivating fluid contacting surfaces.

Figure 7A:
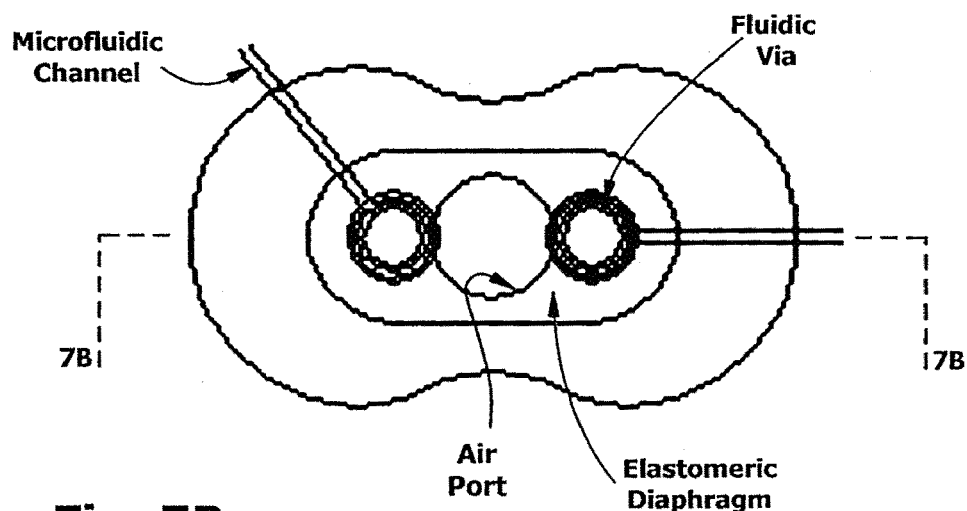
FIG. 7 is a plan and section of a pneumatic valve element, connected to a pneumatic manifold, for controlling fluid flow in a microfluidic channel.
Figure 7B:
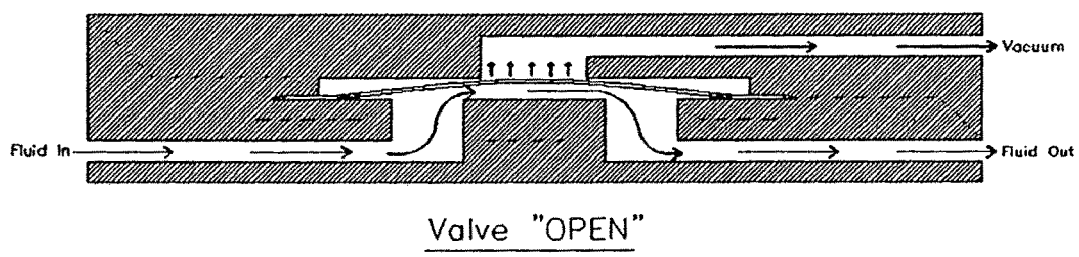
Figure 7C:
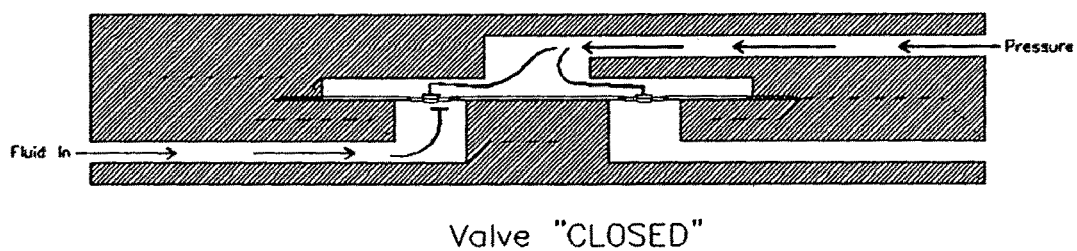

FIG. 7 is a plan and sectional view of a pneumatic on-off valve of the inventive devices, which relies on a pneumatic control diaphragm to open and close an interconnecting port between two vias in the valve. The diaphragm is typically an elastic material that rests on the dam between the two fluid vias and when pulled up by a vacuum, it tents sufficiently that fluid can flow under it. Conversely, under positive pressure, the diaphragm presses down on the mouths of the vias, preventing fluid flow. Above the diaphragm, a via connects the valve with a microfluidic channel with pneumatic interconnect built into a separate layer of the device, which is in operation plugged in to interconnect to the arms of a complex pneumatic manifold used to control the assay.

FIGS. 7B and C are sectional views of the on-off valve of FIG. 7A and show its workings. An elastomeric diaphragm mounted above an inlet and outlet via controls fluid flow. In this embodiment, when the diaphragm is pulled up, fluid flows over the dam from inlet to outlet. When the diaphragm is pressurized, fluid flow is cut off. Diaphragms are held in place between plastic laminates by two-sided adhesive layers.

Figure 8:
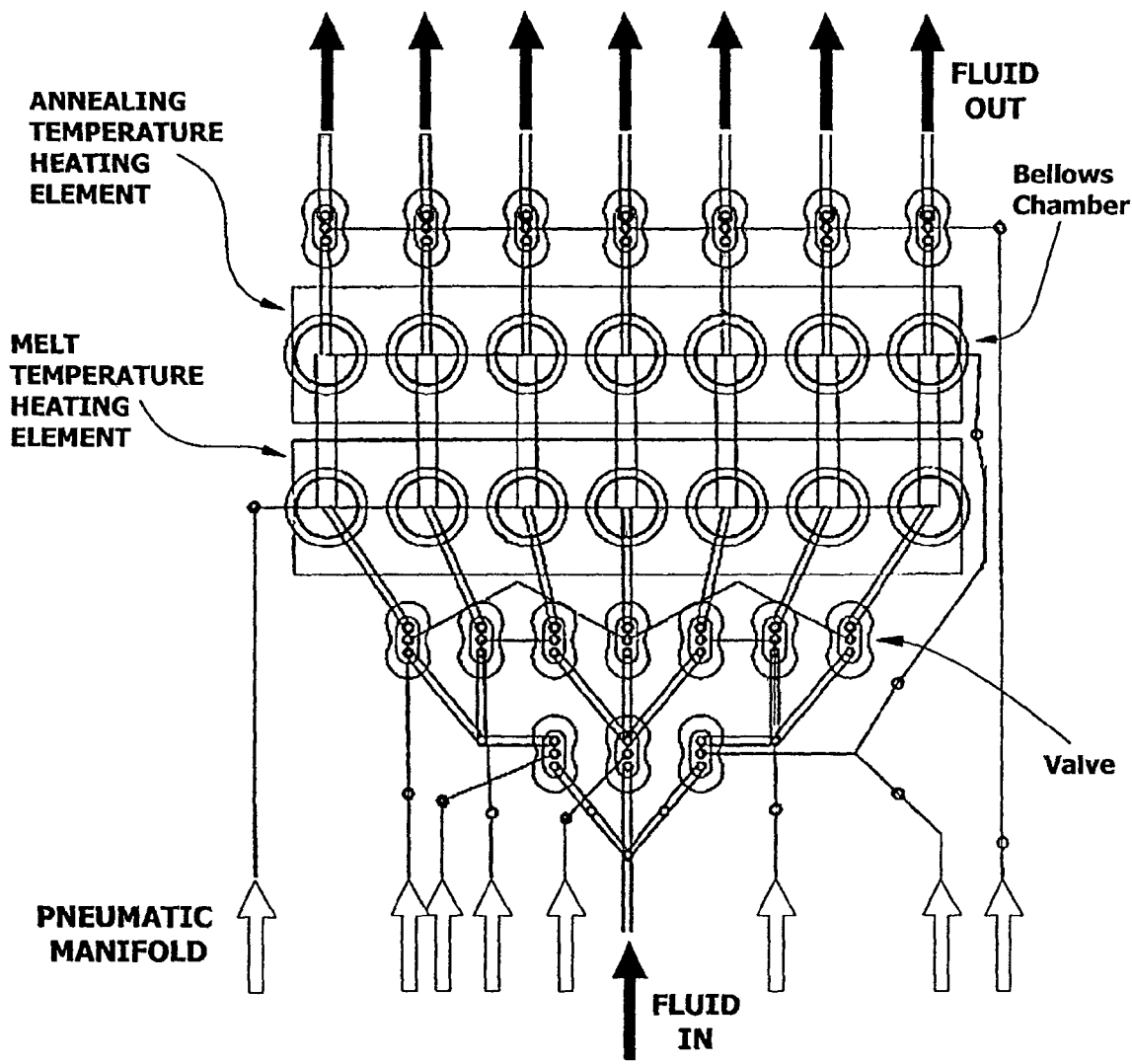
FIG. 8 is a microfluidic valve distribution tree.

FIG. 8 depicts an array of valves for distribution of a fluid. The fluid side of the valve tree and the collateral pneumatic control system are generally built into separate layers above and below the diaphragm respectively.

Program instructions for applying pressure and vacuum to the valves and pumps requires design of the valve logic to operate the device, so that each device is in fact a mechanical invention on its own four legs. An off-device microprocessor is programmed with an instruction set to control the pneumatic operation of the devices. The microprocessor, associated solenoids, and positive and negative pneumatic pressure sources are located off-device on an associated analytical instrument into which the microfluidic devices are inserted.

Figure 9A:
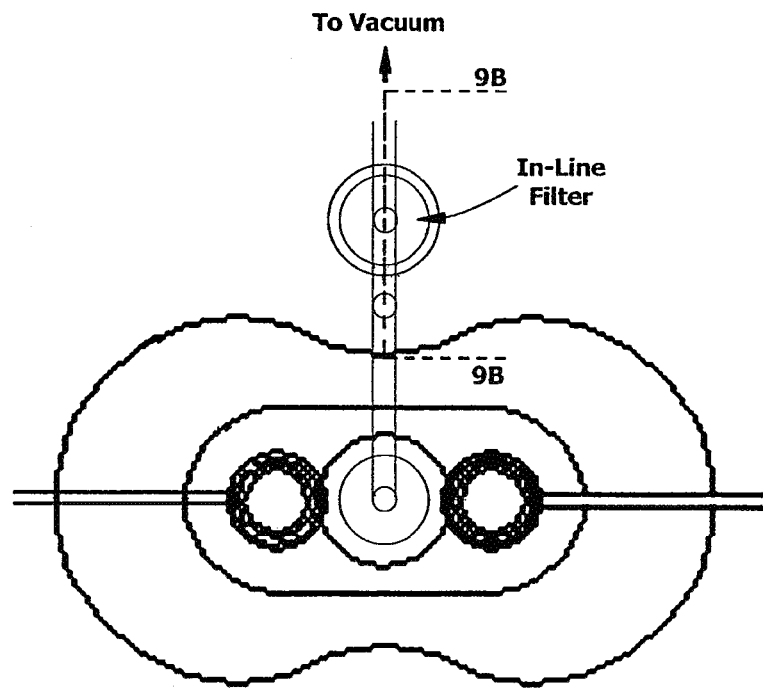
FIG. 9 is a plan and section of a pneumatic valve with in-line sanitary isolation filter in the pneumatic manifold.
Figure 9B:
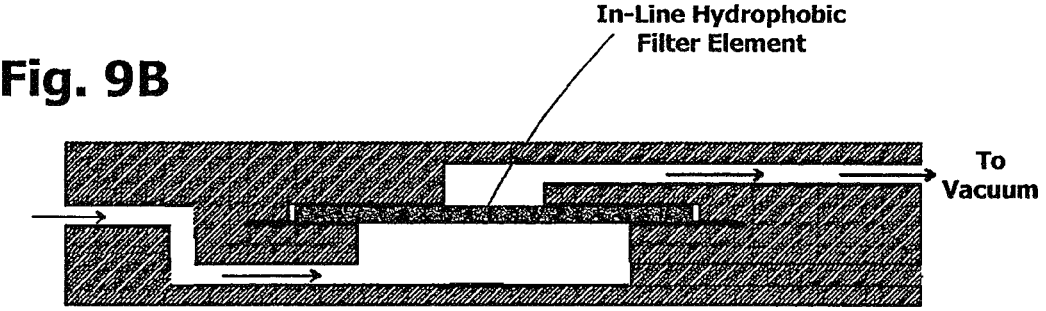

FIG. 9 depicts plan and section of a modified on-off valve having a sanitary filter in-line with the pneumatic channel controlling the diaphragm in the valve. In this embodiment, if the diaphragm fails, contamination of the pneumatic manifold with the fluid contents of the device is avoided. FIG. 9B shows a partial section, which includes a fluid trap below the hydrophobic membrane. These membranes are used in sterile processing because gas flow is permitted but aqueous liquids are stopped at the filter. Filter membrane pore size can be 0.45 microns and can be validated for sterile processes.

Figure 10A:
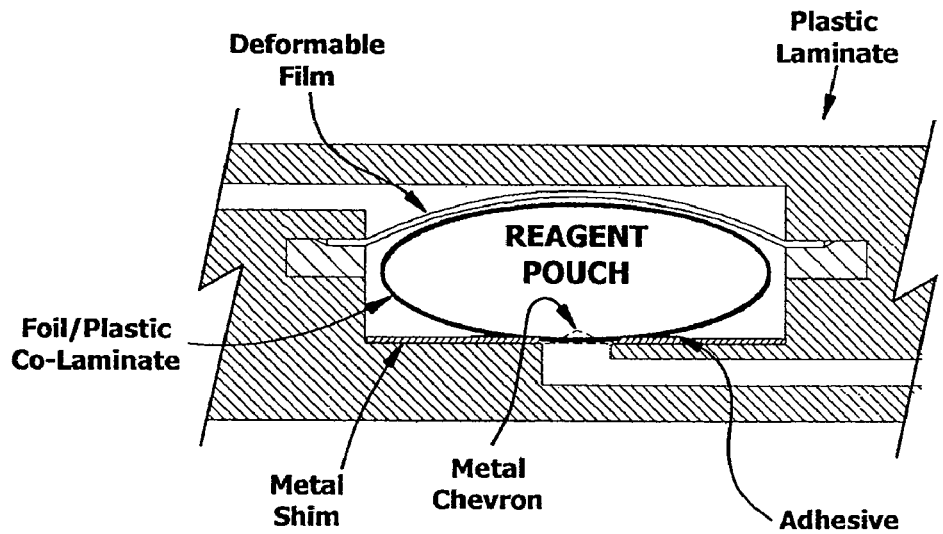
FIG. 10 is a sectional view of a blister pack in operation.
Figure 10B:
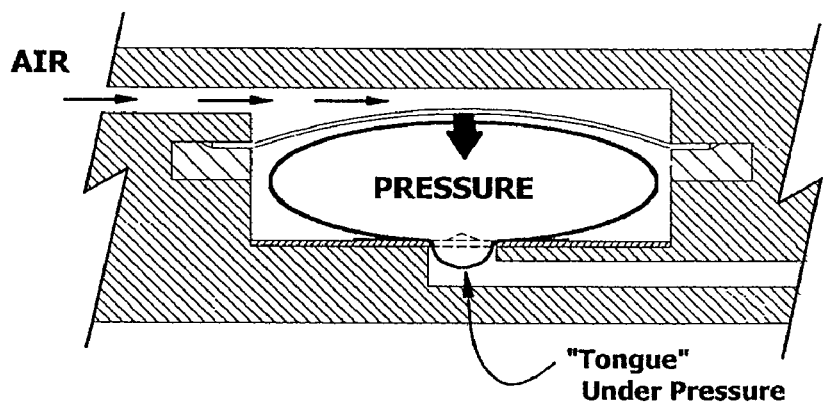
Figure 10C:
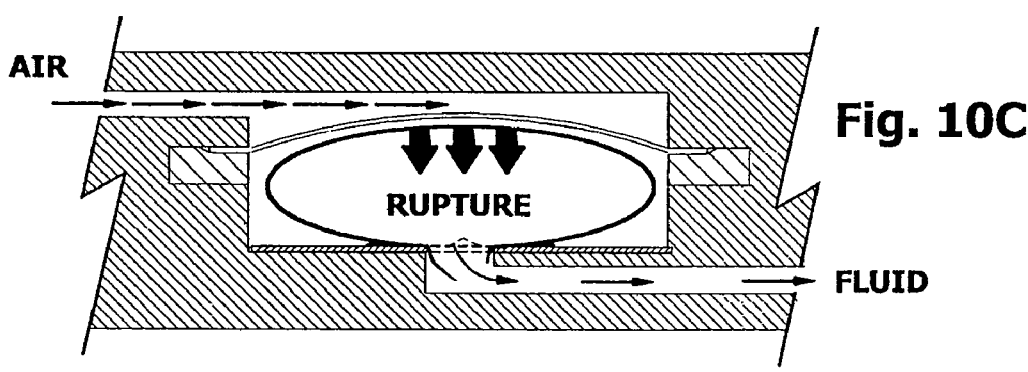
Figure 14A:
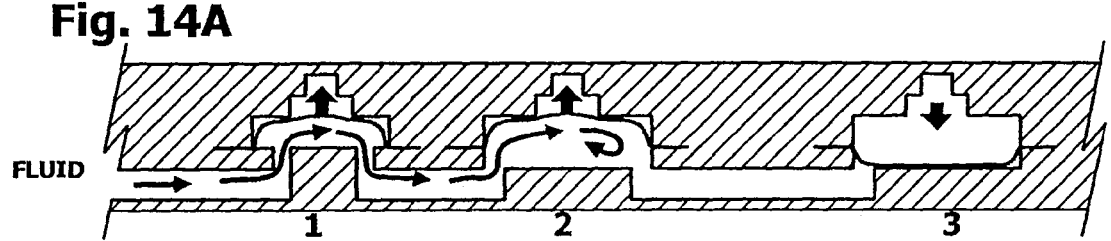
FIG. 14 is a sectional view of the device of FIG. 13 in operation. Thermocycling occurs as fluid flows back and forth between the two chambers with independently controllable fixed temperature thermal interfaces.
Figure 14B:
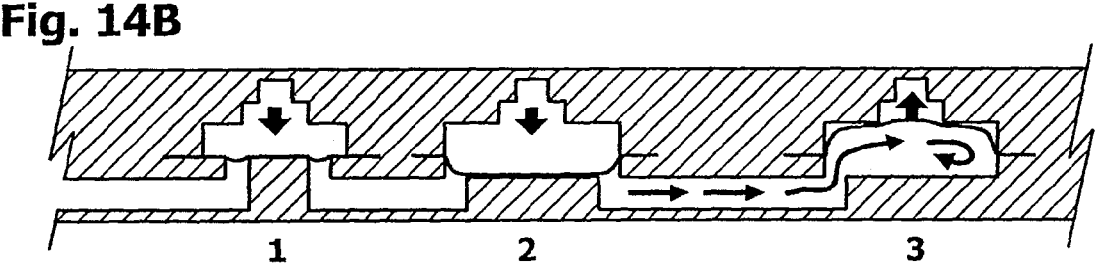
Figure 14C:
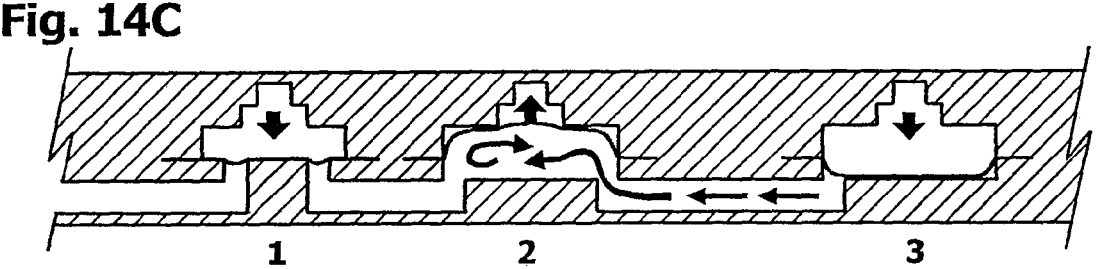
Figure 14D:
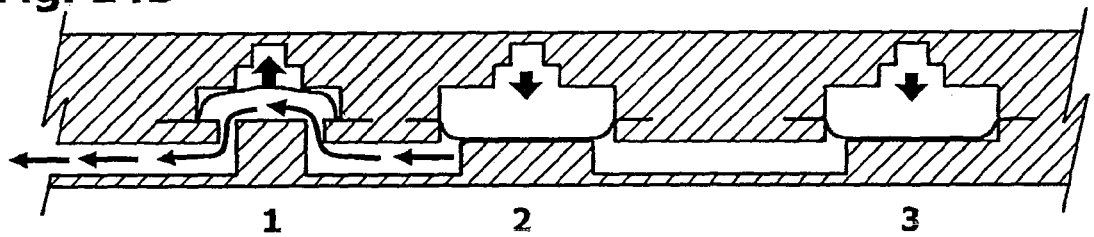
Figure 16A:
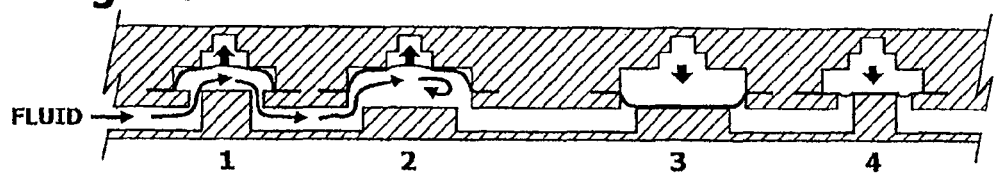
FIG. 16 is a sectional view of the device of FIG. 15 in operation. Thermocycling occurs as fluid flows back and forth between the two chambers with independently controllable fixed temperature thermal interfaces and with through-flow.
Figure 16B:
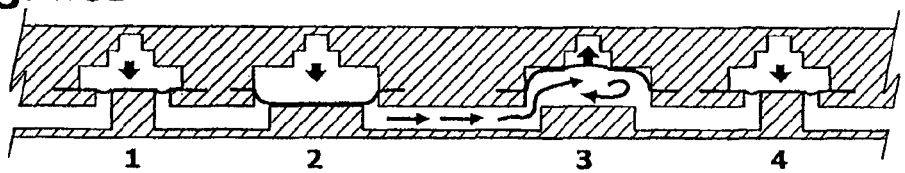
Figure 16C:
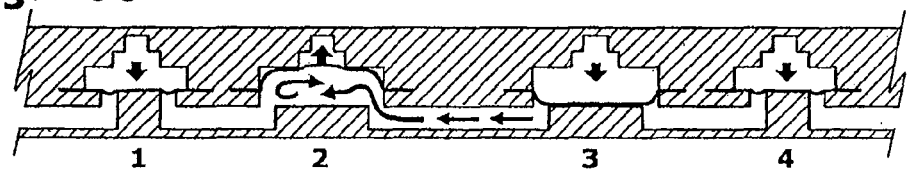
Figure 16D:
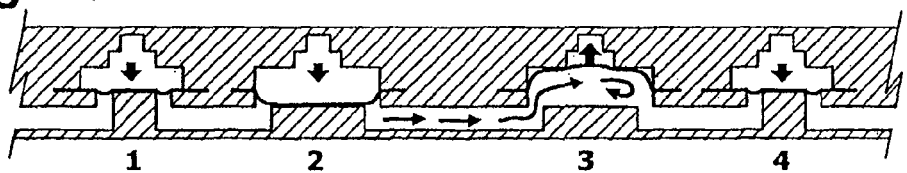
Figure 16E:
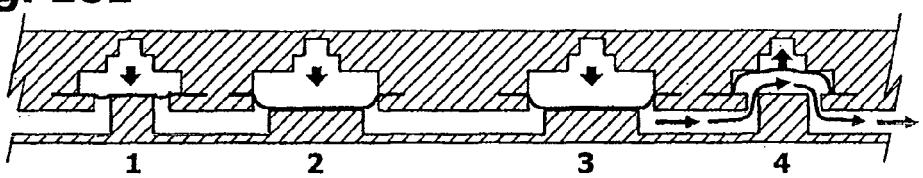

FIG. 10 illustrates a sectional view of a blister pack containing a reagent pouch used to store on-board reagents during transport and prior to use. Reagents are loaded at the time of manufacture and are released under pneumatic control in the proper sequence during the assay. A deformable membrane between the reagent pouch and the airport avoids possible contamination of the device with material introduced in the air supply. As air pressure accumulates above the deformable membrane (FIG. 10A, B, C in sequence), downward pressure on the reagent pouch forces a tongue of the reagent pouch through an orifice in a shim inserted below the pouch. The pouch is glued to the shim by adhesive except where it protrudes into the orifice. A cutting sharp or chevron is located in the orifice, so that air pressure deforms the pouch, bringing it into contact with the sharp, thus rupturing the pouch and releasing the reagent contents.

Throughout the design of these devices, double layers of protection are provided so that contaminated waste does not leave the device. As illustrated in FIG. 11, fluid waste entering the waste sequestration receptacle first encounters a fibrous, bibulous pad. As the pad swells, it displaces the elastomeric diaphragm or deformable film that isolates it from the outside vent. In the event of failure of the deformable film, a hydrophobic filter mounted in the vent via stops fluid leaks.

Pads are made of materials similar to those found in absorbent articles such as disposable diapers. The absorbent core typically includes a fibrous web, which can be a nonwoven, airlaid web of natural or synthetic fibers, or combinations thereof. Fibrous webs used in such absorbent articles also often include certain absorbent gelling materials usually referred to as "hydrogels," "superabsorbent" or "hydrocolloid" materials to store large quantities of the discharged body fluids. These materials absorb through capillary or osmotic forces, or a combination of both (see U.S. Pat. Nos. 4,610,678 and 5,906,602, herein incorporated by reference). The bibulous diaper or pad of fiber material is optionally treated with a dessicant. Fiber pads are typically cellulosic. Dessicants include calcium sulfate, gypsum, calcium chloride, and silica gel.

All air displaced as the liquid reagents are introduced into the microfluidic assay channel exits the device through a sanitary vent with filter which is hydrophobic and permeable to gas but not liquid, thus protecting the operator to exposure to biohazards.

Guanidinium salts, alcohol, and detergents function in the waste chamber as disinfectants. A disinfectant may be used in combination with the above. When designed appropriately, the device can be discarded after use without special precautions.

Figure 27:
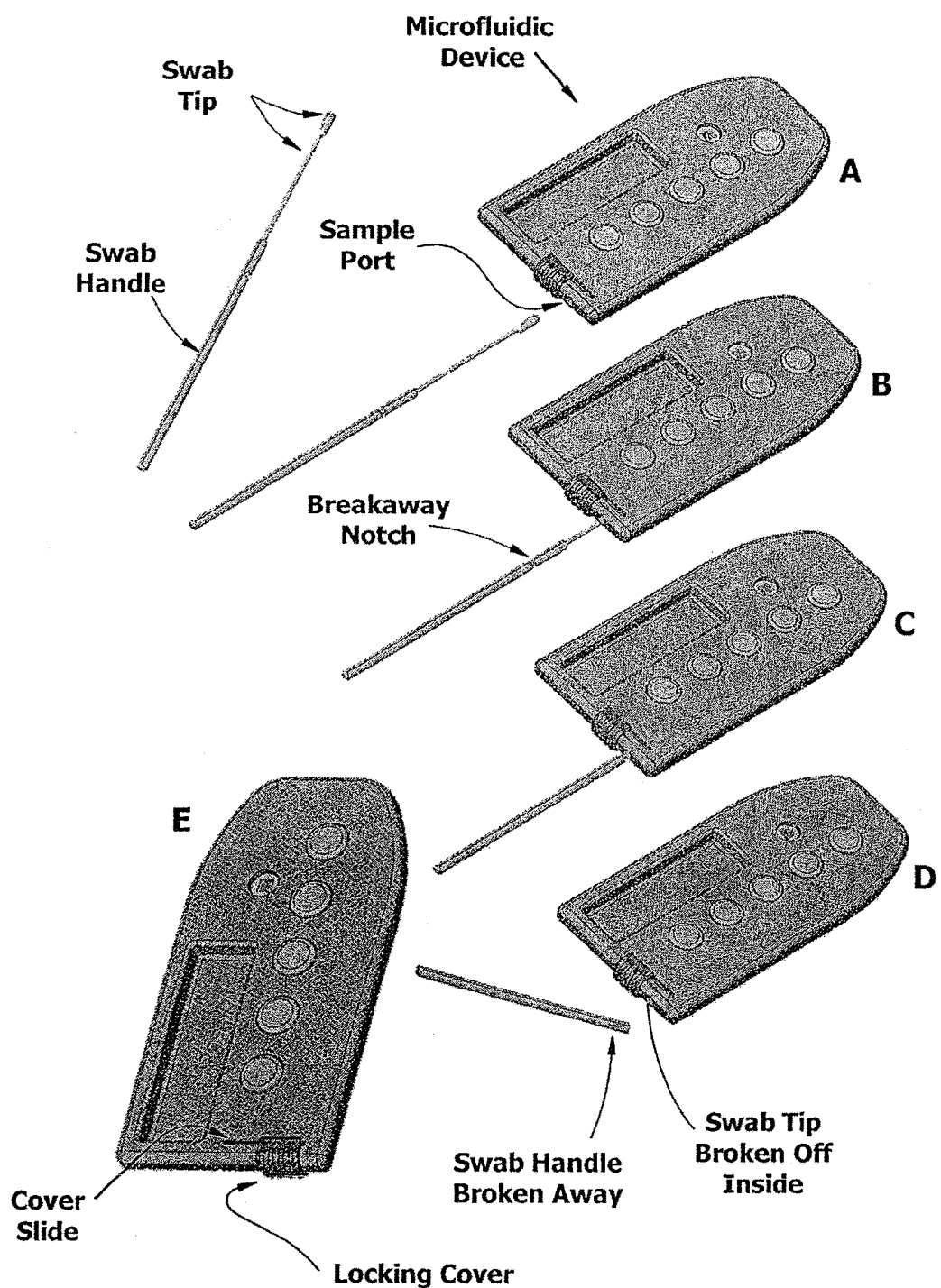
FIG. 27 is a more generalized schematic of a positive detection event depicting a two-tailed amplicon as a tether for immobilization of a reporter group on a solid substrate.

The architecture of the microfluidic device of FIG. 27 has been engineered so that once a sample is placed in the device, exposure of the operator to its contents is avoided. The design ensures a single-entry, disposable device for medical or environmental testing. Optional sealing and locking mechanisms covering the sample port are flushed with lysis buffer following sample insertion and closure for safety in handling.

FIG. 12A shows a schematic of a bellows chamber with pneumatic actuator channel under valved control. The bellows chamber is supplied with an elastomeric membrane and under suction pressure, will draw in fluid through the fluid entry channel FIG. 12B shows two sectional views of a bellows chamber in operation. In the upper view, an elastomeric diaphragm has been pulled up under vacuum toward the air port, drawing fluid into the device. On the downstroke, when the diaphragm is pressurized, fluid is forced out of the chamber body. The bellows chambers can also be used as pumps, and deliver positive and suction head pressure. When used in combination with check valves, unidirectional pump flow occurs.

These bellows chambers can be used, we have found, as reaction chambers, as in PCR. Thermocycling can be achieved by pairs of bellows chambers fluidly interconnected and separately temperature controlled so that fluid passes back and forth from chamber to chamber as the diaphragms are alternated in pressurized and vacuum configurations. This reciprocal flow also can be used as a mixing device, as it has been in ELISA reactions on microfluidic devices.

By forming the base of the bellows chamber out of thin laminated films with high thermal conductivity coefficients, we have found that they make excellent heat exchangers and permit rapid thermocycling in a compact package. In a preferred embodiment, the underside of the device is separated from the heat source by a plastic film having a thermal conductivity of greater than about 1 W/m-° K.

FIG. 13 is a plan view of a pair of bellows chambers configured as a PCR fluidics and thermal interface assembly of the invention. Two fixed temperature interfaces are used, one under each bellows chamber, forming a PCR fluidics and thermal interface. Only a single valve is required. Fluid moves back and forth between the chamber under control of pneumatic actuators on the left and right. Fluid entering the first chamber encounters denaturing temperature conditions. Upon passage into the second bellows chamber, the temperature is reduced so that annealing with primers can take place. Extension occurs on addition of polymerase and continues until the strands again separate under denaturing, or "melt" conditions. The cycle is repeated by alternating compression and rarefaction over the two diaphragms, producing cyclic reciprocating flow between the chambers. After the required number of cycles, the amplified material is expelled from the chambers to the detection station.

The operation of two bellows chambers as a reaction vessel for PCR is explained with reference to the sectional views of FIG. 14. The process has four steps, illustrated as Figs. A, B, C and D, and three microfluidic elements, numbered 1, 2, and 3. Microfluidic element 1 is a valve. Elements 2 and 3 are bellows chambers. Bellows chamber 3 is dead-ended. All elements are fluidly interconnected.

In step A, valve 1 and bellows 2 are under negative pressure, so that the valve opens and fluid is drawn into the first bellows chamber. Note the elastomeric diaphragm separating the fluid and the pneumatic manifold. This corresponds to the first step in PCR, where the sample is mixed with primer pairs and denatured. In step B, the valve closes, sealing the system. Bellows chamber 2 empties under positive pressure and bellows chamber 3 fills under negative pressure. This corresponds to annealing and extension. In step C, the first round products are returned to bellows chamber 2, where strand separation again occurs. Steps B and C are repeated for the required number of cycles. Then the fluid is expelled from the chambers by opening valve 1 and pressurizing bellows chambers 2 and 3. Heating results in convective mixing.

FIG. 15 describes a variant of the above. Sample enters from the left. Here net fluid flow is from left to right. Product exits to the detection station on the right. Two valves are used. As before, the two bellows chambers function as PCR reaction fluidics and thermal interface.

The process has five steps, illustrated as FIGS. 16A, 16B, 16C, 16D and 16E and four microfluidic elements, numbered 1, 2, 3 and 4. Microfluidic elements 1 and 4 are valves. Elements 2 and 3 are bellows chambers. Bellows chamber 2 has a fixed temperature corresponding to the nucleic acid melt temperature; bellows chamber 3 has a fixed temperature corresponding to the temperature required in PCR for annealing and extension. All members are fluidly interconnected by microchannels. Total volume of the PCR fluidics is about 50 uL.

In step A, valve 1 and bellows 2 are under negative pressure, so that the valve opens and fluid is drawn into the first bellows chamber. Note the elastomeric diaphragms separating the fluid and the pneumatic manifold. This corresponds to the first step in PCR, where the sample is mixed with primer pairs and denatured. In step B, the valve closes, sealing the system. Bellows chamber 2 empties under positive pressure and bellows chamber 3 fills under negative pressure. This corresponds to annealing and extension. In step C, the first round products are returned to bellows chamber 2, where strand separation again occurs. Steps B and C are repeated for the required number of cycles. In step D, the fluid is transported to bellows chamber 3. Then the fluid is expelled from the PCR fluidics by opening valve 13 and pressurizing bellows chambers 2 and 3. Upon exiting valve 4, the reaction mixture can be mixed with magnetic beads as described in FIGS. 3 and 4.

Figure 17:
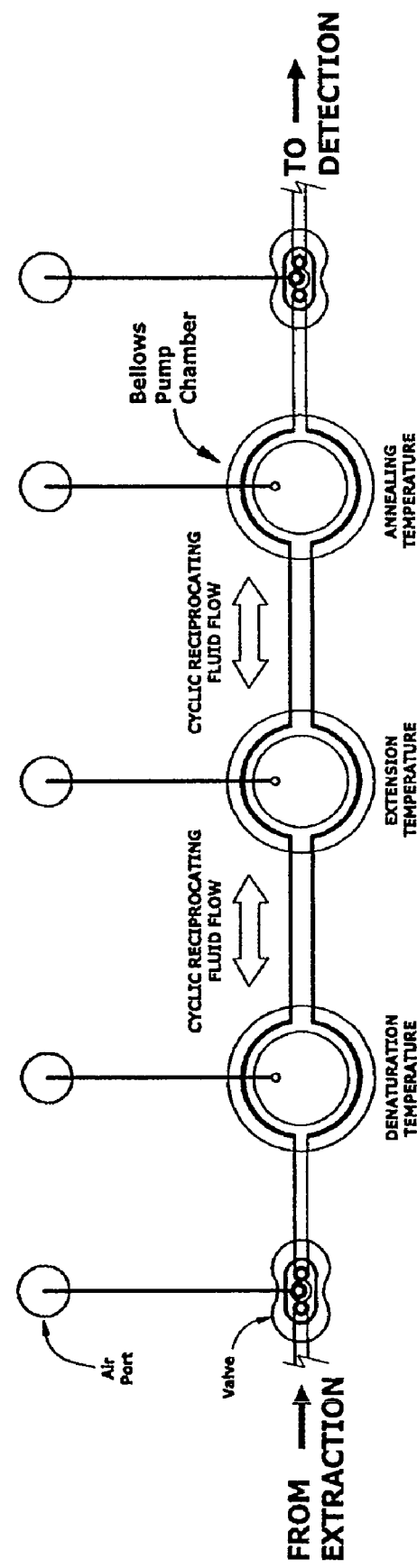
FIG. 17 is a plan view of an optional amplification subcircuit having three reciprocating bellows pump chambers with independently controllable fixed temperature thermal interfaces and with through-flow.

FIG. 17 shows a three bellows chamber embodiment, having three fixed temperature stations corresponding to melt temperature, extension temperature, and annealing temperature. A preferred temperature for extension is slightly higher than for annealing and can be provided for in a separate reaction vessel. As in FIG. 15, the reaction mixture does not exit the PCR fluidics by crossing through the hot side, but instead exits from the annealing chamber or vessel on the right.

Figure 18:
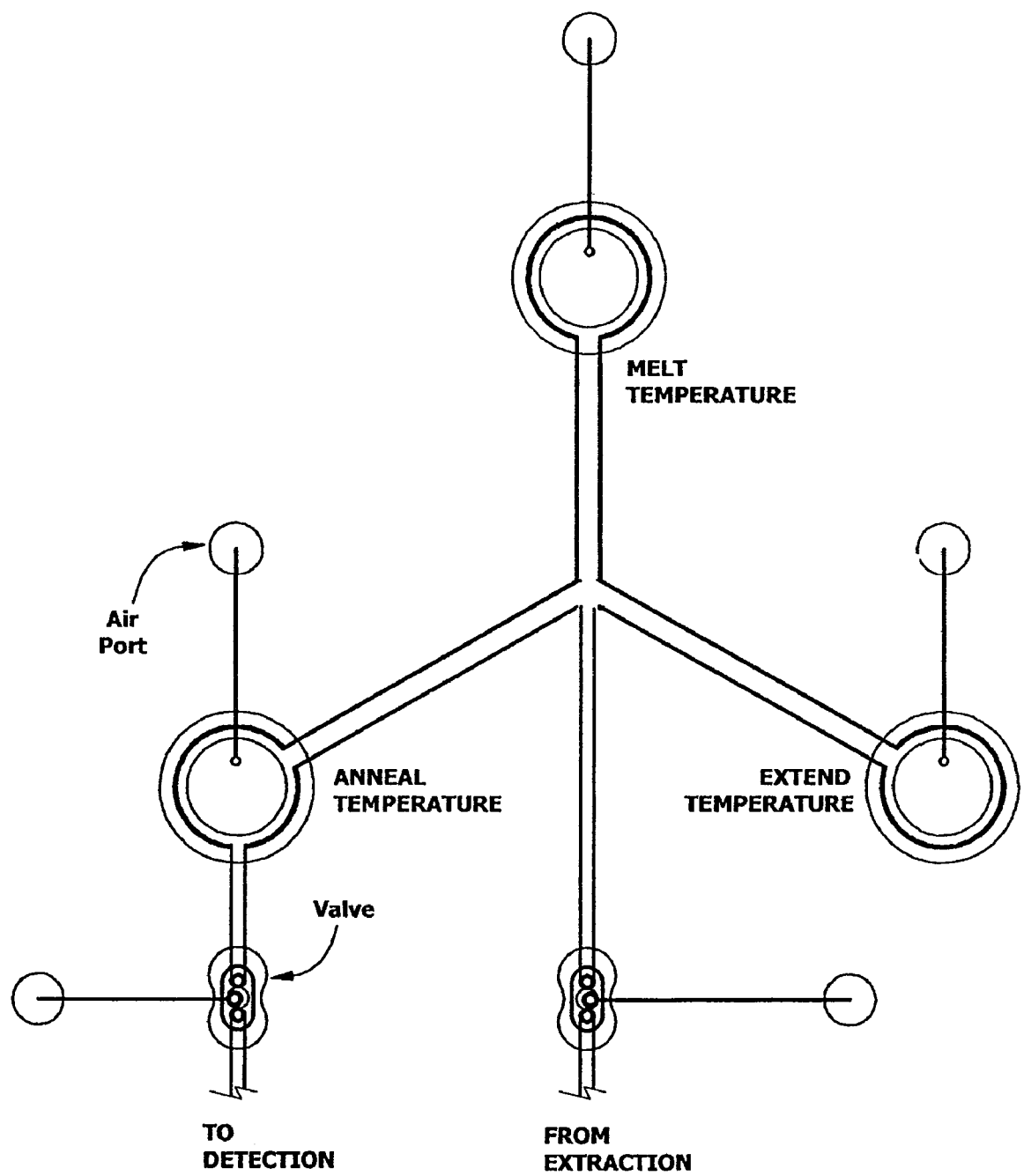
FIG. 18 is a plan view of an optional embodiment of an amplification subcircuit having three reciprocating bellows pump chambers with independently controllable fixed temperature thermal interfaces and with through-flow. Note that the denaturation chamber is distanced from the remaining bellows chambers and that fluidic communication between any two chambers is independent of the third chamber.

FIG. 18 shows a triplex bellows chamber embodiment, having three fixed temperature stations. This configuration does not require valves between the bellows chambers because fluid directional flow to any selected chamber can be controlled by applying the right combination positive and negative pressure to the bellows diaphragms. The PCR cycle begins with entry of test fluid from the extraction (bottom) directly into the melt temperature vessel at the top of the figure. After strand denaturation and dry dissolution of primer pairs and reagents in the interconnecting microchannel, the reaction mix is then directed to the anneal chamber. After reaching annealing temperature, as can be measured with on-board RTDs, thermocouples, or by laser thermometry, the reaction mixture is then transferred to the extension temperature chamber or vessel for an effective period of time, and the cycle repeats. Cycle time is generally less than a minute. Because all chambers are interconnected, flow from melt to anneal, anneal to extend, and extend to melt all occur without passage through an inappropriate temperature regime. Upon completion of the required number of cycles, the reaction mixture is cooled and double stranded product is formed in the anneal chamber before it is expelled to the detector through a valved microchannel (bottom left). All these processes are controlled by air ports associated with the bellows and valve diaphragms.

The embodiment of FIG. 18 lends itself to the "Hot Start" protocol for PCR amplification. Target DNA enters the amplification subcircuit from the extraction subcircuit. In the PCR fluidics of FIG. 16, the sample first encounters dried primer mix, with a magnesium salt and sufficient nucleobase triphosphates for the amplification. These reagents may optionally be dried in place by manual spotting or automated printing device, and may include a matrix such as bovine serum albumin, trehalose, or PEG 3000, for example, to improve wetting, passivation and rehydration.

The target mix with primers is immediately directed into the denaturation chamber under the control of valve logic. Here target DNA dissociates to free single stranded template, so that when the reaction mixture is transported to the annealing temperature, primer-target hybrids are formed with the proper complementarity. The mixture then enters the primer extension chamber, where polymerase has been deposited in dehydrated form. As the polymerase is rehydrated, primer extension begins. This is the 'hot start' method, which has previously been suggested by others to improve product yield and specificity (D'Aquila et al, 1991. Nucleic Acids Res 19:37-49; Chou et al, 1992. Nucleic Acids Res 20:1717-1723; Kellogg et al, 1994. Biotechniques 16: 1134-1137).

Other PCR fluidics configurations include a circular microchannel spanning two temperature blocks so that fluid is thermocycled as it flows along a circular path. Isothermal designs are also contemplated for isothermal amplification protocols.

Figure 19A:
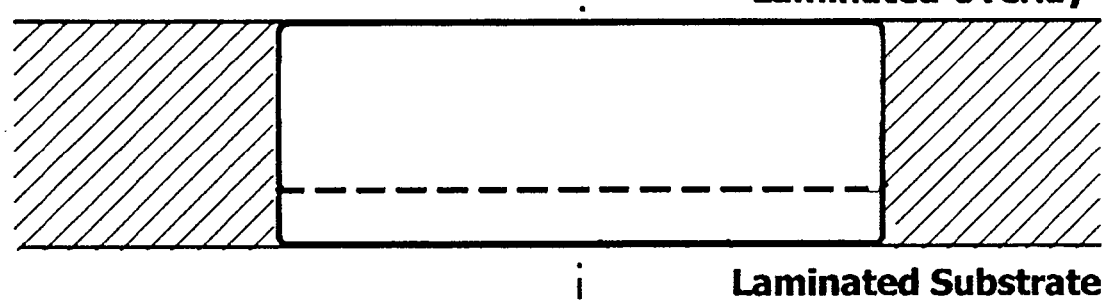
FIG. 19 shows an elevation and section of a microfluidic in-line mixer with narrowest dimension approaching diffusional free path length.
Figure 19B:
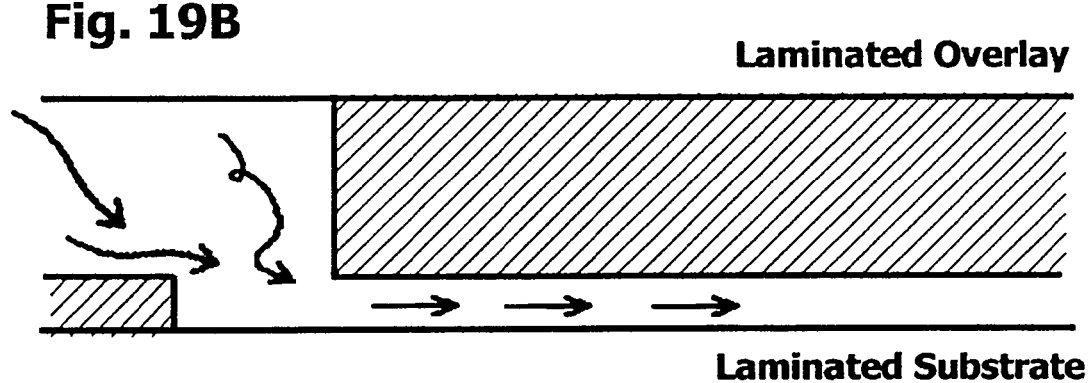

FIG. 19 illustrates a microfluidic mixer. Turbulent mixing in microfluidic channels is limited. Mixing in microfluidic flow regimes can be accomplished by reducing the height of a microchannel to a dimension approaching the diffusional path length of the molecules of interest. For typical solutes, this dimension is in the range of 25 microns (about 1 mil). Therefore a step reduction in a channel as shown in FIG. 19, for example, can be used to bring fluid streams into contact at dimensions where diffusional mixing suffices.

Figure 20A:
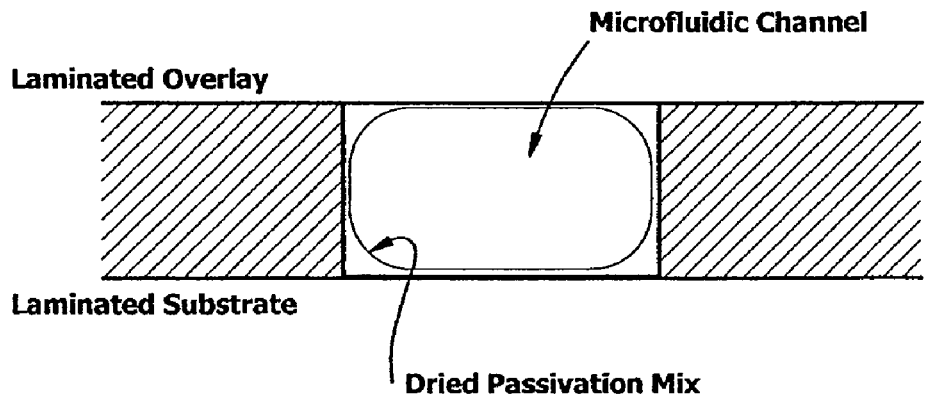
FIG. 20 is a sectional view of a microfluidic channel, reservoir and chamber having deposited dehydrated reagents

FIG. 20A illustrates methods for passivating the internal fluid-contacting surfaces of microfluidic devices, for example microchannels. Suitable surface active passivators include for example serum albumin, Poloxamers, polyvinylpyrrolidinone, PEGylated surfactants, Tween-80, Triton X-100, and mixtures thereof. In some cases, silane coatings are used as hydrophobes. Hydrophobic materials may also be applied at microfluidic junctions to prevent passage of aqueous solutions, for example at a "Tee" to direct the fluid down one arm of the Tee and not the other.

Figure 20B:
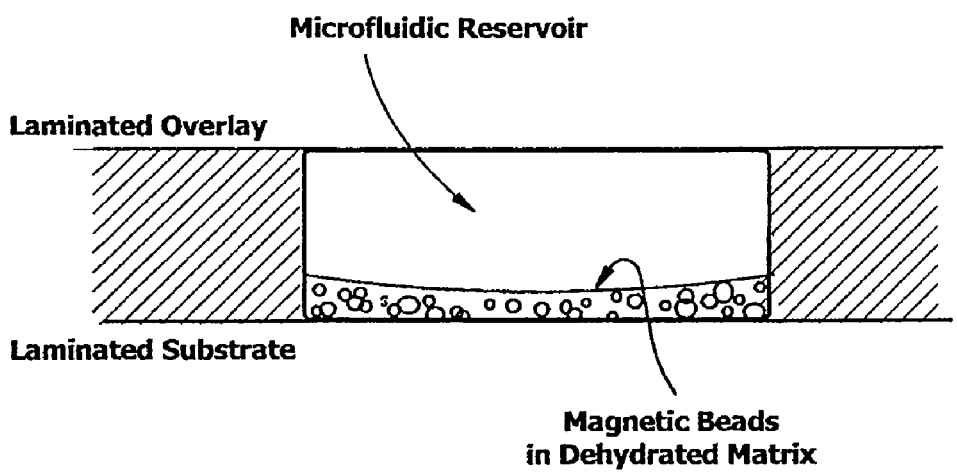

FIG. 20B illustrates the process of depositing magnetic beads in a suitable matrix for reconstitution inside a chamber or reservoir prior to final assembly of the microfluidic device. Rehydration of beads is generally accomplished with a rehydration buffer.

Figure 20C:
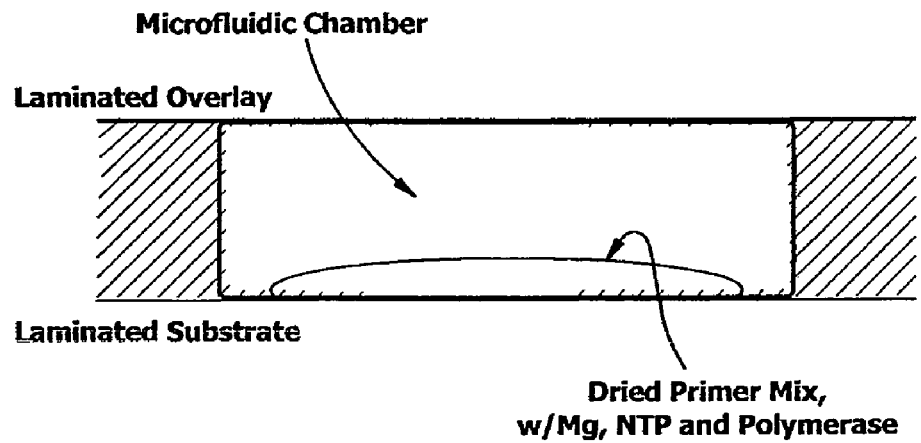

FIG. 20C illustrates deposition of a "PCR mix" in an amplification chamber as part of or in proximity to the PCR fluidics assembly. Dried mix typically contains primers, magnesium, dNTPs, and polymerase, optionally with surface active agents. Elution buffer can be used to rehydrate the PCR mix. Convective heat-forced fluid mixing in the PCR fluidics aids in reconstitution of the dehydrated PCR mix. Similarly, reverse transcriptase and associated cofactors can be deposited as dried reagents in a secondary chamber. Other enzymes or reagents may also find utility in this way.

FIG. 21 shows a rendering of a detection chamber 2100 or station in the form of a broadened microfluidic channel, the bottom of which has been masked and treated to form pads 2102 for immobilized antibody 2103. The ceiling of the chamber forms an optical window 2104. Magnetic beads entering the detection channel in a fluid stream at 2101 are subjected to a magnetic force that brings the beads into proximity to the antibody and moves them through the channel. Early washes can be performed by holding the beads against the ceiling or floor of the chamber while flushing with buffer. After the beads are immobilized on the test pads, added washes can be performed as needed to clear the chamber of free beads and aid in a clear view of the endpoints. Unbound beads and reaction materials may be magnetically moved to waste, or rinsed to waste.

Figure 22:
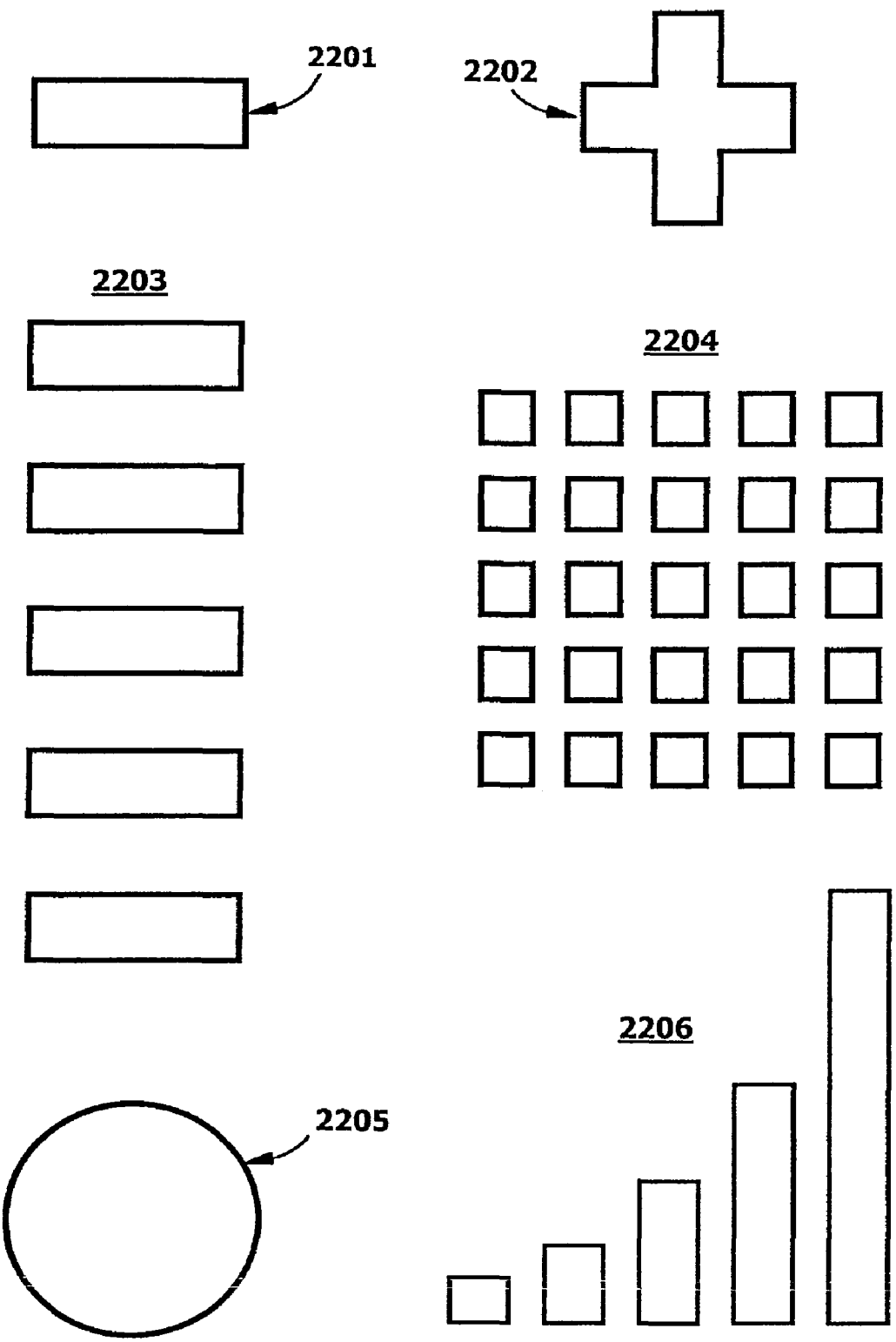
FIG. 22 is a plan view of representative test pad geometries.

In FIG. 22 we show test pad geometries. Test pads are a feature of the detection step of the method described herein. Test pads 2201 and 2202 constitute for example a negative and positive detection field for an assay. Test pad array 2203 is a linear banded or striped array not unlike that shown in FIG. 21. Test pad array 2204 is a rectangular array of individual test squares, each treated with a unique capture agent. Test pad 2205 is circular and is adapted to inkjet printing. Test pad 2206 is treated with a gradient of a capture agent so as to display a readily interpretable semi-quantitative endpoint.

Test pads have in common a field bounded by an edge inside of which a bioactive capture agent is immobilized. While not a comprehensive list, the capture agent may be a protein such as an antibody, an anti-antibody, an anti peptidyl hapten antibody, Protein A, Protein G, or antigen, or a non-protein such as an aptimer, a carbohydrate antigen, a mucopolysaccharide, or an oligomer. Capture agents may also include denatured viral antigens and microbial antigens in general and cellular components or whole cells in general.

Note that test pads are not necessarily impermeable substrates, and may be porous or fibrous in character. The analyte fluid path in the magnetic field may be across or through the test pad area, as in from side-to-side or from front-to-back. The test pad architecture, at a molecular level, is essentially three-dimensional, although it may be represented as a two-dimensional plane.

Solid substrates for test pads include olefin or other thermoplastic materials such as polystyrene, polycarbonate, polypropylene, polyethylene terephthalate, polyether sulfone, polyvinyl chloride, polyvinyl acetate, copolymers of vinyl acetate and vinyl chloride, and polyamides and also inorganic materials such as glass. Certain fibrous or porous supports such as nitrocellulose, nylon, hydrogel, and polyethylene may also be applied as test pads, and may be pretreated with capture agent for ease of assembly. To enhance binding of capture agents, crosslinked proteins are sometimes employed. Drying also promotes irreversible binding of the capture agent. Other capture agents may require modified protocols as are known in the art.

A preferred method for pretreating plastic prior to adsorbing the capture agent is low pressure gas plasma treatment. Exposure of the surface to pure oxygen or nitrogen produces an activated hydroxylated and carboxylated substrate layer or an activated aminated and nitroxidated layer, respectively. Argon may also be used. In one embodiment, polystyrene plastic is used as the substrate for immobilizing capture agent. Masking, followed by gas plasma treatment is used to activate designated areas as test pads. The capture agent is applied, dried in place, and the mask is removed. When antibody is used as the capture agent, application by hand or with an automated printer is followed by drying and blocking. Other capture agents require modified protocols as are known in the art.

Techniques for surface activation are reviewed in Chan et al (1996) Surface Science Reports 24:1-54 and in Garbassi et al. (1998) Polymer Surfaces—From Physics to Technology (John Wiley pp 238-241), and in U.S. Pat. No. 6,955,738, which describes hydrophilization and functionalization of polymer surfaces and is incorporated herein in its entirety by reference.

The use of multiple capture pads in the detection chamber permits multiplexing of results, i.e., multiplex detection in a multiplex detection chamber. In a preferred embodiment, visual presentation offers convenience to the user, but instruments for detection of positive results on arrays smaller than can be visually discriminated are also contemplated. Instrumental detection of non-visual detection events are also within the scope of this invention.

It is understood that microfluidic devices optionally may include RFID, microchips, or bar code labels as an aid in processing analytical data.

Variants of the embodiments described above are now illustrated.

Figure 23:
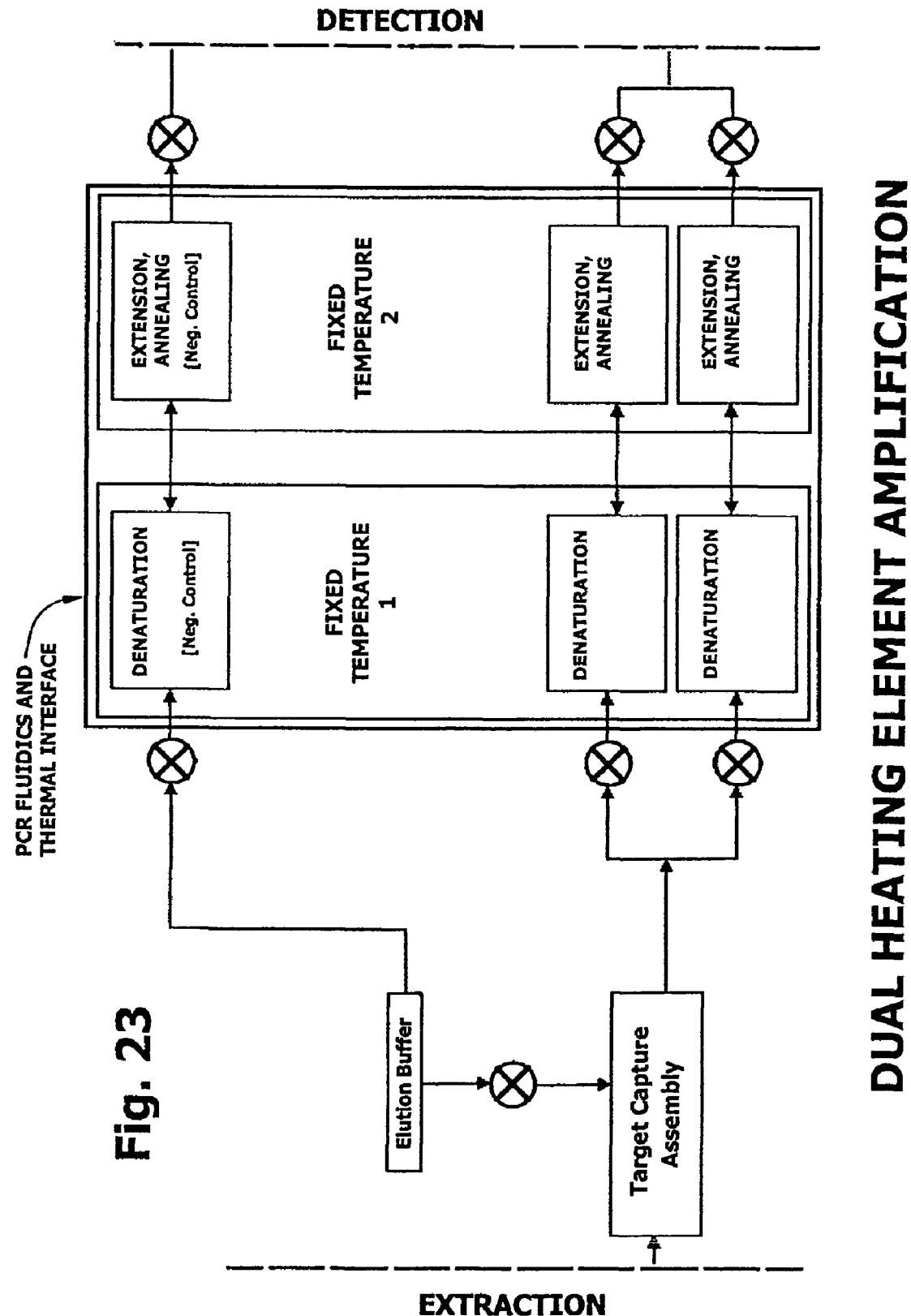
FIG. 23 is a schematic of an amplification subcircuit having two fixed-temperature thermal interfaces.

FIG. 23 depicts an optional duplex amplification assembly having two interconnecting fixed temperature chambers, an annealing chamber (50 C) on the left and a denaturation chamber (96 C) on the right. Each is an automated bellows chamber in series, as in FIG. 15. Flexible elastomeric diaphragms of polyurethane are used to pull the fluid back and forth under vacuum and pressure. By applying vacuum to one chamber while pressurizing the other chamber, near quantitative fluid transfer from chamber to chamber can be achieved. Mixing is achieved in the interconnecting microchannel. By controlling the temperature in each of the chambers at a fixed point, a cycle of denaturation, annealing and extension is completed each time the fluid is moved from one chamber to the other and back.

Figure 24:
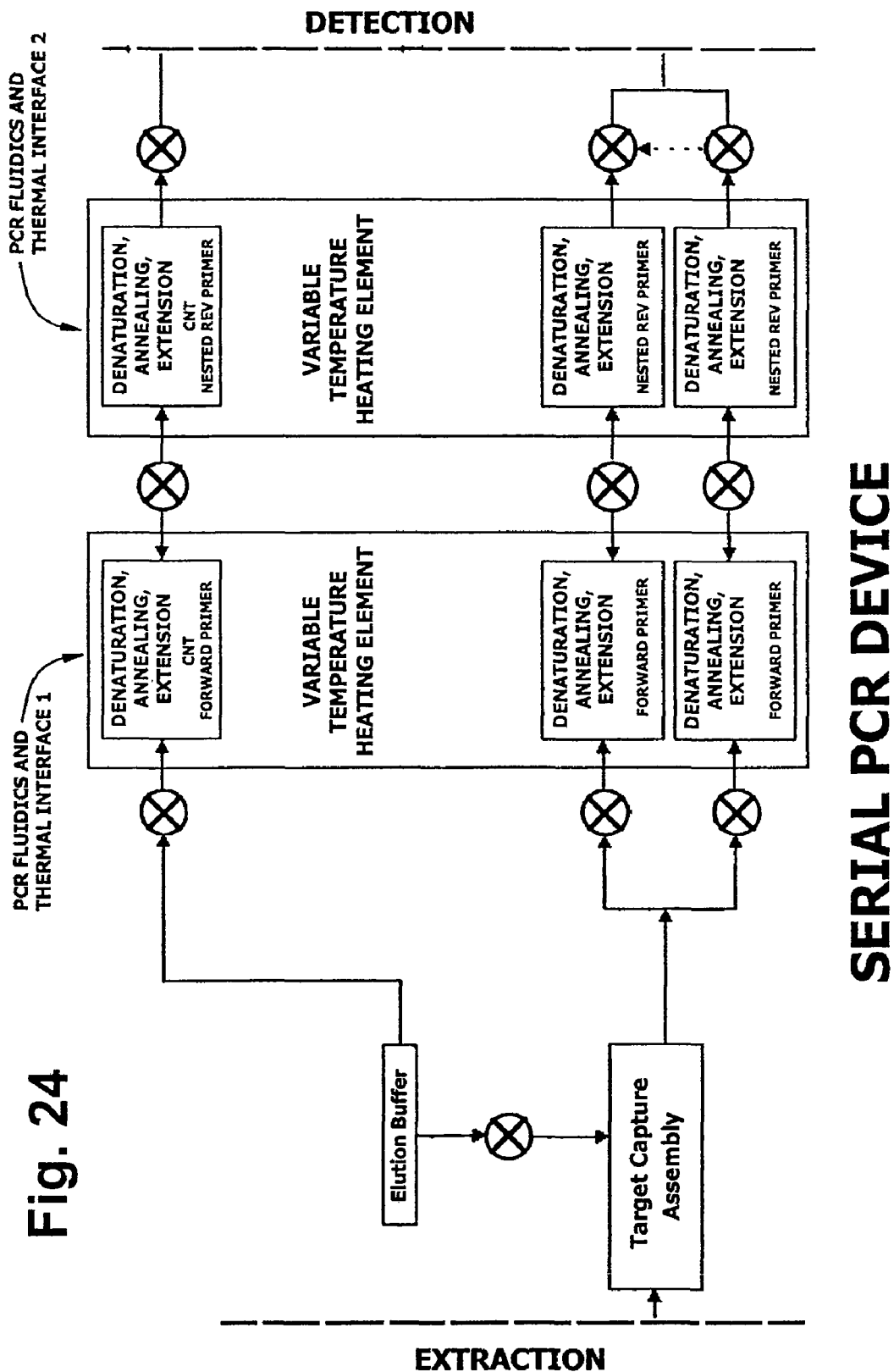
FIG. 24 is a schematic showing a device for an assay protocol relying on sequential PCR reactions.

FIG. 24 depicts a schematic having two tandem PCR fluidics and thermal interface assemblies so that serial PCR may be performed. PCR products from first round PCR in Assy 1 (left) are transferred through interconnecting valves to assy 2 (right), where PCR is again conducted with fresh reagents and primers. This for example is useful in performing asymmetric PCR, or hemi-nested PCR where the products of a first primer pair are then amplified by a primer pair consisting of at least one primer selected from the amplified sequence proximal to the distal 3' end of the amplicons of the first reaction.

A two-tailed amplicon of the invention is obtained after two rounds of PCR.

Only one of the primers used in the first round amplification is tagged, but the third nested primer used in second round PCR, carries the second tag. Other variants are possible.

Figure 25:
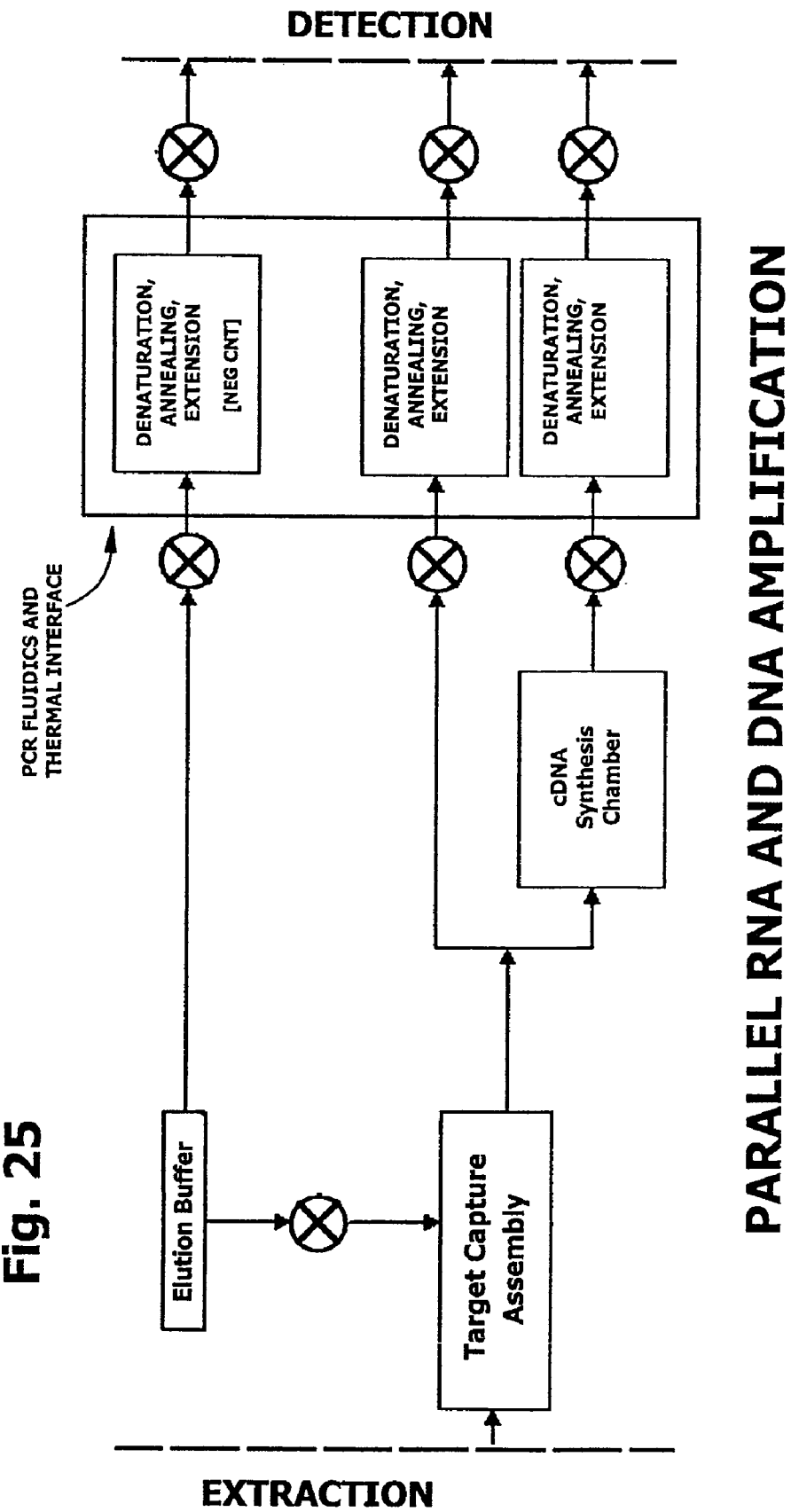
FIG. 25 is a schematic of an extraction and amplification subcircuit with provision for analysis of RNA.

Turning now to FIG. 25, we see the sample path branches at a "Tee" after elution from the Target Capture Assembly. A "cDNA Synthesis Fluidic Assembly" is interposed on one arm of the branch. In this option, the two parallel paths serve different analytical functions. One path is used to analyze the DNA content of the sample, which may treated with RNAase. The other branch is directed to a microfluidic element for synthesis of cDNA from RNA by any of several prior art methods well known to those skilled in the art, but usually involving one of the reverse transcriptases. It is the cDNA that is then analyzed by PCR.

Figure 26:
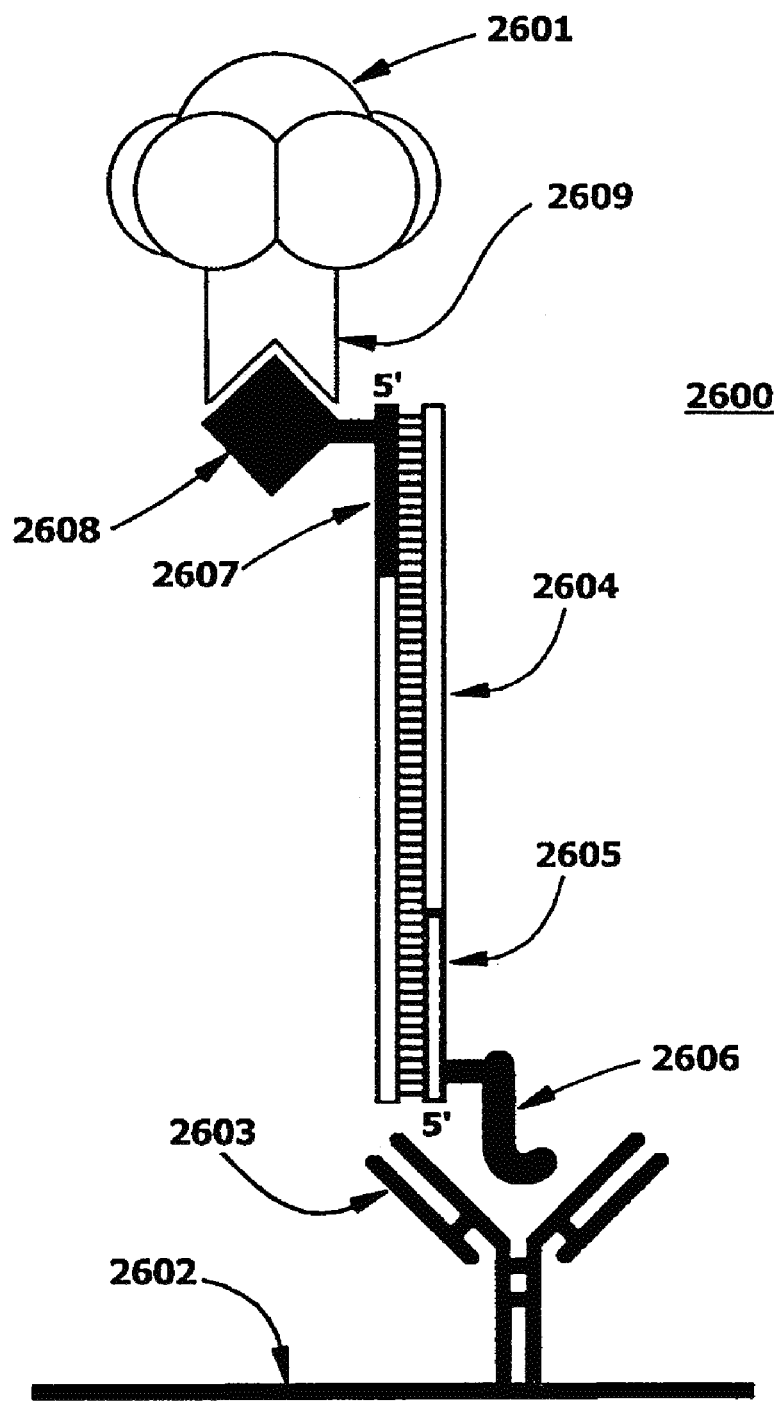
FIG. 26 is a conceptual model of a single-entry device with sealable sample port for swab with breakaway handle.

In FIG. 26, a molecular detection complex 2600 comprising a phycoerythrin-avidin reporter complex 2601 is shown tethered to a solid substrate 2602 by an antibody 2603 and two-tailed amplicon 2604. First primer 2605 is conjugated with a peptidyl hapten 2606 complementary to the immobilized antibody 2603. Second primer 2607 is conjugated with biotin 2608, and the biotin is used to capture the reporter complex 2601 before immunocapture on the solid substrate (thus avoiding the "hook" effect).

It should be seen from this figure that variants of the unique molecular detection complex are readily constructed. The phycoerythrin-avidin reporter complex (2601) was chosen here because it is readily available and has strong fluorescent signal. But numerous other reporter groups or particles may be substituted.

The common elements are the two tailed amplicon with peptidyl hapten on the first primer, the complementary anti-peptidyl hapten antibody immobilized on a detection surface such as a test pad, and a reporter group of some kind bound to a complementary ligand on the second primer.

Use of anti-epitope haptens for immunocapture takes advantage of the high degree of specificity of antibody binding and the near infinite variability of the peptide peptidyl hapten tags that can be conjugated to the first primer. This permits construction of amplicon libraries by amplification with conjugated primer pairs and subsequent interrogation of those libraries in the bioassay.

Reporter groups include fluorophores, biotin, digoxins, peptides, quenchers, proteins, beads, particles, microspheres, magnetic microbeads, proteins, and so forth.

FIG. 27 is a conceptual sketch of a fully self-contained, stand alone, single entry analytical device for patient care. In A, a sample swab is inserted into the sample port. In B, C and D, the use of a breakaway notch in the swab is illustrated to describe how the sample can be completely isolated. After the swab handle is broken away, locking cover is slid in cover slide to seal the sample port. This cover locks and cannot be reopened without force and a sharp tool. A button is then pressed to start the assay. Manual or automated versions are conceived. At the end of the assay, a detection event is displayed in an optical window. The detection event involves the molecular construct of the present invention, but is not limited to such.

Optionally, once the locking cover is in place, the underside of the cover can be flooded with disinfectant so that the device is fully disposable without special precautions. We envisage devices of this kind for analysis of nasal and rectal swabs, and for other biological specimens.

FIG. 28 is a key to the graphical symbols used in FIGS. 1-4.

Temperature Control

A single block TEC with ramp temperature control was used in early development of the assay. In this embodiment, Peltier chips are used to control heat transfer to and from a suitably sized heat sink under control of a PID controller. Rapid response of the amplification channel or chamber was engineered by reducing the thermal mass and thermal diffusion barrier of the microfluidic device and associated heating block. Subsequently, dual fixed temperature blocks were used in PCR protocols. Because of the relatively small volumes required for amplification, mixing in the amplification chambers is achieved by thermal convection of the fluid. No mechanical mixing element is required.

Other aspects of the invention relate to sample preparation and primer design.

Sample Preparation

Extraction of nucleic acids from the sample is critical in developing clinical assays. Difficult specimens include stool and sputum. Blood, because hemoglobin interferes with the activity of polymerases used in amplification, may also be problematic.

However, we have been successful with a very rapid means to a) prefilter clinical samples to remove gross particulate, b) lyse the target pathogens in a chaotrope such as guanidinium thiocyanate, c) trap the nucleic acids, and then d) after serial washing on a nucleic acid trapping member, e) elute directly into the PCR fluidics assembly for amplification. Surprisingly good results are obtained by this rapid method, which avoids chloroform:phenol extraction, treatment with proteinase K, centrifugation, and other more complex and time consuming prior art means described in the literature.

From the amplification subcircuit, the amplification mixture is transported directly into the detection subcircuit, where results are visualized in 2 to 6 minutes, most preferentially in about 4 minutes. In accomplishing this, by combining fluidic subcircuits for extraction, amplification, and detection in a microfluidic device, we have developed a seamless interface between sample preparation, amplification, and diagnostic result. Total assay time, sample volume, reagent volumes, labor and expense are significantly reduced.

Optimization of Amplification

Lysis of microorganisms and virus particles in a sample may require partial solubilization of nucleocapsid, lipids and mucopolysaccharides in the sample. Optional pre-treatments include use of mercaptoethanol or n-acetyl-cysteine to break disulfide bonds, use of "universal solvents" such as n,n-dimethylformamide and n-methylpyrrolidinone to disrupt nucleic acid: protein and nucleic acid:lipid associations, as well as freeze-thaw or mechanical pre-treatments, such as with a dounce homogenizer, sonication, or french press for tissue samples. A mini-bead impact mill or sonicator also can be used for samples containing gram positive cocci, rods or endospores.

Lysis yields mixed nucleic acids generally consisting of significant amounts of ribosomal and messenger RNA. Many viruses of interest may be RNA viruses, but for large numbers of bacteria, the targets of interest are plasmid or genomic DNA. Therefore, treatment of the lysate with an RNAase (thus removing rRNA and mRNA that compete for binding and elution) can aid in maximizing the amount of DNA bound on the nucleic acid target capture assembly.

It is also possible to amplify intron sequences rather than the customary open reading frames (exons), and by doing so avoid competition of mRNA for primer binding.

As describe earlier, hot start PCR has been suggested to improve sensitivity and amplification yield, reducing primer dimers and nonspecific amplification. This is especially important in first round extensions, which can set the stage to dominate subsequent amplification.

Also suggested for multiplex amplification protocols has been a two-stage amplification in which first round amplification with a mixed primer pool to amplicon copy numbers of about a thousand or less is followed by amplification of aliquots of the reaction mixture in separate chambers with individual primer pairs. Detection can be multiplexed by the method of the present invention.

Another amplification means is to perform asymmetric amplification in which a peptidyl haptenized primer is used to make a high copy number of the complementary strand, and then the reverse haptenized primer is added and amplification is repeated to complete the synthesis of both of the duplex target sequences. The net result is the same, duplex amplicons are labeled at one end with one hapten and at the other end with biotin or the like. Since the primers do not see each other at high concentration, minimal primer dimer is formed. In a variant of asymmetric amplification, a third primer can be used which is selected from a sequence upstream from the second primer, and it is the third primer, not the second primer, that is peptide haptenized. This hemi-nested variant of PCR aids in reducing doubly tagged primer dimer formation.

Preferred primers are 10 to 30 bases in length; more preferred primers are 17-28 bases in length. Shorter primers may result in nonspecific amplification. Sequence distance between forward and reverse primers should be on the order of 70 to 600 bp, more preferably 100 to 300 bp. Base composition of the primers should be 40 to 60% G+C, more preferentially 50 to 60% G+C, with no clustering of the purines, particularly at the 3' end.

Devices, apparatus, and methods for both simplex and multiplex amplification of nucleic acid targets are contemplated here. Simplex amplification, which is easily accomplished in parallel PCR fluidics and thermal interface assemblies under ganged valve control, is a preferred embodiment.

Both simplex and multiplex detection devices are contemplated here. Multiplex detection is a preferred embodiment. Visual means of multiplex detection are preferable among the means disclosed here, although machine means, manual means, and automated detection means are also contemplated.

Assay Targets

Diagnostic detection of various pathogenic agents is contemplated. Blood-borne pathogens include *Salmonella typhosa, Salmonella paratyphi, Bacillus anthracis, Brucella abortus, Brucella suis, Brucella melitensis, Yersinia (Pasteurella) pestis, Pasteurella multocida, Francisella tularensis, Spirillum minus, Burkholderia mallei, Leptospirum ictohaemorrhagiae, Coxiella burnetii, Rickettsia typhi*, Hantavirus, Dengue fever virus, Yellow fever virus (and other viruses of the Flavivirus group), West nile virus, Japanese B encephalitis virus, St Louis encephalitis, Western equine encephalitis, Human immunodeficiency virus 1 and 2, Human T-cell leukemia virus 1 and 2, *Dirofilaria immitis* in dogs, *Plasmodium vivax*, falciparum, malaria, ovale and berghei, to name a few. Quantitative detection of *P. falciparum*, the cause of blackwater fever, may be important in blood.

Wound and bite pathogens include *Staphylococcus aureus, Streptococcus pyogenes* serotypes responsible for necrotizing fasciitis, *Pseudomonas aeruginosa, Clostridium perfringens, Clostridium tetani, Yersinia pestis, Bacillus anthracis*, and *Bacteroides fragilis*.

Central nervous system and CSF pathogens include *Neisseria meningitides, Streptococcus pneumoniae, Listeria* monocytogenes, syphilis, *Haemophilus influenza* serotype B, *Acinetobacter* spp, *Escherichia coli, Enterobacter* spp, *Pseudomonas aeruginosa, Staphylococcus aureus*, viral encephalitis such as Japanese B encephalitis, Mumps virus, Polio virus, herpes viruses (HSV-1, HSV-2), varicella zoster virus, and Rabies virus.

Representative urinary pathogens are dominated by gram negative rods, and include *Proteus mirabilis, Proteus vulgaris, Escherichia coli, Klebsiella pneumoniae, Enterobacter cloacae*, and occasional *Pseudomonas* infections, for example.

A panel for sexually transmitted diseases is contemplated. Pathogens of clinical interest include *Neisseria gonorrhoea, Treponema pallidum*, Herpes simplex, *Chlamydia trachomatis, Papilloma virus, Candida albicans*, and the like.

Enteric pathogens include Enterobacteriaceae of the genera *Salmonella, Shigella* and certain serovars of *E. coli*, among others. Also pathogenic are a broad swath of parasites and viruses.

Selected pathogens may be detected individually or in panels by the devices of the invention. Kits for detection of selected pathogens or pathogenic conditions are anticipated.

Detection of gram positive cocci, gram positive rods, yeasts, and endospores, may require sample pretreatment in a mini-bead impact mill, ultrasound, or by peptidoglycanase or chitinase prior to analysis. Diagnosis of subacute bacterial endocarditis is contemplated.

In other embodiments, detection of cancer cells in blood or tissues is contemplated. Protocols for adapting mammalian cell lysis to a microfluidic card of the present invention are anticipated. Primer pairs may be selected from oncogene sequences. Diagnosis for pathogenic conditions of the cardiac, immune and vascular systems are also contemplated.

The cartridges are particularly adapted to assay panels run in parallel. In a preferred embodiment, an on-board multiplex detection chamber permits simultaneous presentation of multiple results.

Use of peptidyl primer tagged amplicons in assays of this kind is another aspect of the invention. A number of methods are now available for manufacture of specific peptide epitopes attached to oligonucleotide probes or primers (see C.-H. Tung and S. Stein, Bioconjugate Chem., 2000, 11, 605-618; E. Vives and B. Lebleu, Tetrahedron Lett., 1997, 38, 1183-1186; R. Eritja, A. Pons, M. Escarcellar, E. Giralt, and F. Albericio, Tetrahedron Lett., 1991, 47, 4113-4120; J. P. Bongartz, A. M. Aubertin, P. G. Milhaud, and B. Lebleu, Nucleic. Acids Res., 1994, 22, 4681-4688; C.-H. Tung, M. J. Rudolph, and S. Stein, Bioconjugate Chem., 1991, 2, 461-465; J. G. Harrison and S. Balasubramanian, Nucleic. Acids Res., 1998, 26, 3136-3145; S. Soukchareun, J. Haralambidis, and G. Tregear, Bioconjugate Chem., 1998, 9, 466-475; K. Arar, A.-M. Aubertin, A.-C. Roche, M. Monsigny, and M. Mayer, Bioconjugate Chem., 1995, 6, 573-577; and, for an example of the use of the native ligation technique see: D. A. Stetsenko and M. J. Gait, J. Organic Chem., 2000, 65, 4900-4908). See also U.S. 20006/0263816, incorporated herein in full by reference.

The peptidyl hapten primers of this method are synthesized by these chemistries. We disclose here that these primers are compatible with PCR methods and with molecular biological nucleic acid amplifications in general. For use in assays, the amplification product with amplicon incorporating peptide-tagged primer is first captured by an affinity capture agent specific for a ligand on the second primer of the amplification primer set and thereby bound to a magnetic microbead. The amplicon-bead complex is then interacted with peptide-specific antibodies on the testpad and only those bead complexes with the peptidyl hapten amplicon molecular complex are captured by the testpad (see FIGS. 5 and 26 for illustrations). This method permits screening of peptidyl-amplicon libraries by heterogeneous binding assays using magnetic bead technology. Because of the enormous immunological variability possible with peptide-tagged oligomers, we believe that methods for interrogating libraries of this type provide a previously unrecognized tool of use in molecular biological assays, with or without magnetic beads.

These compositions may be generally described as a molecular detection complex for detection of a pathogen or pathogenic condition, comprising a two-tailed amplicon with first end and second end, said first end comprising a first primer covalently conjugated with a peptidyl hapten, and said second end comprising a second primer covalently conjugated with a ligand, said first end further comprising a ligand-bound ligand binding agent-coated reporter group, and said second end further comprising a peptidyl hapten bound anti-peptidyl hapten antibody, said complex further being immobilized on a test pad, where test pad and ligand are defined broadly.

It should be noted that fluorophore dyed latex beads may be used as "test pad", in a sort of liquid array. By barcoding the fluorophore beads and coating uniformly labeled bead populations with peptidyl-hapten specific antibodies, bead libraries can be synthesized for analysis of mixed populations of two-tailed amplicons or of two-tailed amplicon libraries, and the resulting affinity binding complexes with pairs of beads tethered by the two-tailed amplicons can then be sorted or assayed quantitatively using dual excitation fluorometry.

The devices and apparatuses described herein are generally amenable to the performance of bioassays for nucleic acid targets, and may be combined as kits for the performance of the bioassays by the methods disclosed herein.

A general multiplex nucleic acid target bioassay method has the following steps:

1) selecting a first primer having a hybridization specificity for the 5' end of a first target nucleic acid sequence, and synthesizing a peptidyl hapten-conjugated first primer;

2) selecting a second primer having a hybridization specificity for the 3' end of the first target nucleic acid sequence, and synthesizing a ligand-conjugated second primer, said first and second primers forming a primer pair;

3) repeating steps a) and b) for each of a plurality of target nucleic acid sequences, and pooling the primer pairs;

4) synthesizing two-tailed amplicon products in the presence of the pool of primer pairs;

5) contacting the amplification mixture products with ligand binding agent-coated magnetic beads to capture any resulting two-tailed amplicons comprising said ligand-conjugated first primers;

6) contacting the amplification mixture products with a plurality of test pads, wherein each test pad comprises an immobilized anti-peptidyl hapten antibody, and capturing the two-tailed amplicons on the test pad in the form of a molecular detection complex;

7) scoring the assay as positive for a plurality of pathogens or pathogenic conditions by detecting one or more molecular detection complexes.

Methods for nucleic acid detection as described herein may involve amplification by various means. These include simplex amplification, multiplex amplification, nested amplification, serial amplification, and "hot start" amplification.

Example 1

A) Preparation of Primer Sets

Reverse primers were first prepared and HPLC purified. Peptides were modified with n-terminal hydrazine before use. Oligonucleotides were treated with succinimidyl 4-formylbenzoate in formamide and then reacted with the hydrazine derivatized peptides to form hapten-tagged primers.

The following peptidyl hapten-tagged primers were used.

| 5'-Peptidyl Oligomers | | |
|---|---|---|
| Primer | Primer Sequence* | Peptide Sequence** |
| A | CGCCAGTACGATATTCAG (SEQ ID NO: 1) | (HNA) EQKLISEEDL (NH2)(SEQ ID NO: 8) |

-continued

5'-Peptidyl Oligomers

| Primer | Primer Sequence* | Peptide Sequence** |
|---|---|---|
| B | ACCTGGACATCACGGCTTTCAAC (SEQ ID NO: 2) | (HNA) YPYDVPDYA (NH2)(SEQ ID NO: 9) |
| C | CCTATTGCAGAGCGAATGAC (SEQ ID NO: 3) | (HNA) YTDIEMNRLGK (NH2)(SEQ ID NO: 10) |
| D | TGAACTCCATTAACGCCAGA (SEQ ID NO: 4) | (HNA) CEEEEYMPME (NH2)(SEQ ID NO: 11) |
| E | CGACCTGACCAAATGCCAG (SEQ ID NO: 5) | (HNA) TDFYLK (NH2) (SEQ ID NO: 12) |
| F | CCTATAACAGCACCCACTATACGG (SEQ ID NO: 6) | (HNA) DTYRYI (NH2) (SEQ ID NO: 13) |
| G | CTCTGCGAGCATGGTCTGG (SEQ ID NO: 7) | (HNA) QPELAPEDPED (NH2)(SEQ ID NO: 14) |

These peptide epitopes were selected based on the availability of complementary antibodies. Alternate peptide conjugation chemistries may also be used. Forward primers were all conjugated with biotin.

B) Preparation of Paramagnetic Microbeads

Monodisperse streptavidin-coated magnetic beads (MyOne Streptavidin C1 Dynabeads) were purchased from Dynal, Carlsbad Calif. and washed and resuspended in 0.9× PBS, 30 mg/mL BSA and 1% TritonX100 with 5% (v/v) of a solution of 80 mM $MgCl_2$, 0.24% TritonX100, 1% BSA, in 0.5M TRIS pH 8 before use.

C) Preparation of Test Pads

A microfluidic device was built from stencil-cut laminates and contained multiple detection chambers of the form illustrated in FIG. 9. Each detection chamber was formed with an inlet port and outlet port fluidically connected to the detection chamber by microfluidic channels. Sufficient detection chambers were built for the experiment.

Before final assembly, test pads in the detection chamber were masked and plasma treated with oxygen gas. Peptidyl hapten-specific antibodies (Research Diagnostics, Flanders N.J.) and negative control solution were spotted on the test pads, 1 uL per pad, and dried in place under vacuum. Each detection chamber contained one test pad corresponding to each primer set and a negative control. The fully assembled device was treated with blocking/wash solution consisting of 0.9×PBS, 30 mg/mL BSA and 1% TritonX100 to passivate untreated plastic surfaces. The blocking solution was removed before use and the chambers were dried.

D) Assay Protocol

Using known DNA samples from enteric pathogens, PCR was performed with the prepared primer sets (above) for 35 cycles. Platinum Quantitative RT-PCR Thermoscript One-Step System reagents were used for the amplification. Successful amplification was confirmed by 5% agarose gel electrophoresis. Amplicon 10 uL was then resuspended with 5 uL of beads (above) in about 20 uL of buffer containing 10 mM $MgCl_2$, 0.5% BSA, 0.1% TritonX100 and 5 mM TRIS Buffer pH 8 and the bulk of this solution was loaded into a detection chamber. Each amplicon product corresponded to a single primer set and was loaded into a separate detection chamber.

The beads were first captured with a magnet positioned on the bottom of the detection chamber and the excess solution was removed. The magnet was then used to smear the bead paste onto, through and across the test pads, and the mixture was then allowed to incubate 1 min. With the magnet positioned on the bottom of the well, the well was gradually filled with blocking solution. The magnet was moved along the flow of the buffer, creating a bead front on the bottom layer of the detection chamber. The magnet was then shifted to the top of the detection chamber, lifting unbound beads out of the test pad areas. The unbound material could be resuspended in flowing buffer and rinsed to waste. The test pads were then rinsed with 1 volume of fresh buffer. Bright orange test pad "stripes" were immediately visible and were determined to correctly reflect specificity of binding of the hapten-tagged amplicon to the test pad containing the complementary antibody. Because the detection chambers were aligned in parallel when constructed, a stairstep pattern was evident after all the amplicon bead mixtures were processed because each tagged amplicon was bound by only one test pad in each detection chamber.

Upon clearing, positive tests were immediately visible as bright orange bands corresponding to the location of particular test strips. Negative test strips and negative controls remained translucent and uncolored. The results could be easily decoded by matching the location of the stained test pad with a key of the antibodies used in spotting.

Example 2

PCR amplification was performed in a microfluidic device as follows:

A microfluidic device was built from stencil-cut laminates. Before final assembly, biotin- and hapten-tagged primer pairs, dATP, dCTP, dGTP and dTTP, TAQ polymerase, and a matrix consisting of Triton X100, BSA, PEG and Trehalose plus magnesium chloride were deposited in the amplification channel or chamber and dried in place under vacuum. Streptavidin-coated magnetic beads (Dynal MyOne Streptavidin C1, Carlsbad Calif.) were spotted and dried in a chamber adjoining the amplification channels or chambers. Test pad areas in the detection chamber were stenciled (see FIG. 21 for general approach) and gas plasma treated, before antibody solutions were applied and dried in place. Antibody spots were blocked with StabilCoat (SurModics, Eden Prairie Minn.). The device was then treated with a Triton X100:BSA buffer to passivate untreated plastic surfaces.

The following reagents were also prepared:
Lysis Buffer
    4.5M Guanidinium thiocyanate
    5% Triton X100
    1% Sarcosine
    50 mM MES, pH 5.5
    20 mM EDTA
Wash Reagent
    Anhydrous ethanol
Elution Buffer E11
    1% Triton X100
    0.1 mM EDTA
    20 mM TRIS pH 8.0
    50 U RNAsin (Promega)
Rehydration Buffer
    1% Triton X100
    0.5% NaCl 10 mg/mL Bovine Serum Albumin
50 mM TRIS pH 8.0

Lysis Buffer, Wash Reagent, Elution Buffer, and Rehydration Buffer were aliquoted into sealed blister packs in designated chambers of the device. The device was then fully assembled and placed in a pneumatic controller with variable temperature TEC heating blocks positioned under the PCR fluidics and thermal interface assembly.

Clinical swab samples from diarrhoeal patients known to contain pathogenic microorganisms were handled with gloves in a biosafety cabinet. Each rectal swab was mixed vigorously with 400 uL of TE to solubilize the contents. Using filter-plugged pipet tips, about 400 uL of homogenate was then transferred to the sample port of the microfluidic device and the sample port was closed. All other steps were performed in the single-entry device, with no other operator exposure.

The remaining assay steps were automated.

An on-board sanitary bellows pump was used to pull sample through a pre-filter consisting of a depth filter element, made of polypropylene for example, supported on a laser-cut plastic ribs. A valve was then used to close the sample port. The crude filtrate was then mixed with lysis buffer and drawn through a glass fiber filter to trap nucleic acids, and the filter retentate was rinsed thoroughly with ethanol. All rinses were sequestered in an onboard waste receptacle which vents through a 0.45 micron hydrophobic membrane filter. The nucleic acids on the glass fiber membrane were then eluted with elution buffer and ported into the reaction channel containing primers, dNTPs, polymerase, magnesium, buffer and surface active agents in dehydrated form. The reaction mixture, in a volume of about 50 uL, was then heated to 95° C. in the PCR fluidics and thermal interface assembly for about 10 sec to effect denaturation of double stranded sequences and secondary structure in the sample. Heating and cooling was supplied by external Peltier chips mounted on suitable heat sinks and PID controlled within a 1° C. range from setpoint. Immediately thereafter, the temperature was returned to about 60° C. for a first round of annealing and extension, which was continued for about 20 sec. Thermocycling was repeated for 40 cycles over an 18 min period.

Following extraction and amplification, the amplicon products were moved to a mag mix chamber for mixing streptavidin-labeled magnetic beads (Dynal, MyOne Streptavidin C1) which had been rehydrated in Rehydration Buffer. This mixture was incubated with gentle mixing and then transferred to a MagnaFlow chamber. Optionally the reaction mix can be rinsed to remove unreacted hapten-conjugated primer while holding the magnetic beads in place. Using permanent magnets mounted on an X-Y stage, the coated beads with putative target amplicon were brought into contact with the capture antibody test pads or array in the detection chamber, and unbound beads were moved away from the test pads with a moving magnetic field and sent to waste. Primers and non-specific amplicons were rinsed from the chamber with an excess of rehydration buffer, which again was discarded into on-board waste.

Upon clearing, positive tests were readily visible as orange bands corresponding to the location of particular test strips. Negative test strips remained translucent and uncolored. Time following transfer of amplification mixture to detection event was about 4 min. Knowing the identity of each immobilized antibody, the results could be easily decoded. In best practice to this date, the time from amplification to data presentation is less than 4 minutes.

In a test run with clinical samples, pathogens in 46 out of 47 stools were scored correctly in screening with the Magnaflow device. One sample previously identified as containing Salmonella by culture was identified as also containing enterotoxigenic Ecoli O157H1 by Magnaflow, (i.e., a double infection). For this example, the following primer pairs were obtained by custom synthesis and chemically conjugated by methods known in the art.

| 5'-Peptidyl Oligomers | | |
|---|---|---|
| Target | 3' Target Gene Primer Sequence | Hapten conjugate |
| InvA | CAATGTAGAACGACCCCATAAACA (SEQ ID NO: 15) | EQKLISEEDL' (SEQ ID NO: 8) |
| Gyrase A | GCCATTCTAACCAAAGCATCATA (SEQ ID NO: 16) | DTYRYI' (SEQ ID NO: 13) |
| ipaH | ACTCCCGACACGCCATAGAA (SEQ ID NO: 17) | QPELAPEDPED' (SEQ ID NO: 14) |
| Eae | CTATCCAACAAGTTCAATTCATCC (SEQ ID NO: 18) | TDFYLK' (SEQ ID NO: 12) |
| Stx1 A | AGACGTATGTAGATTCGCTGAA (SEQ ID NO: 19) | YTDIEMNRLGK' (SEQ ID NO: 10) |
| Stx2 A | CTGGATGCATCTCTGGTCAT (SEQ ID NO: 20) | CEEEEYMPME' (SEQ ID NO: 11) |
| MalB | GGCGAATACCCAGCGACAT (SEQ ID NO: 21) | YPYDVPDYA' (SEQ ID NO: 9) |

| 5'-Biotinylated Oligomers | | |
|---|---|---|
| Target | 5'-Target Gene Primer Sequence | Primer Conjugate |
| InvA | TATCTGGTTGATTTCCTGATCGC (SEQ ID NO: 22) | Biotin |
| Gyrase A | AAATGATGAGGCAAAAAGTAGAACA (SEQ ID NO: 23) | Biotin |
| ipaH | GGACATTGCCCGGGATAAA (SEQ ID NO: 24) | Biotin |
| Eae | TTACCCGACGCCTCAAAC (SEQ ID NO: 25) | Biotin |
| Stx1 A | AGACGTATGTAGATTCGCTGAA (SEQ ID NO: 26) | Biotin |
| Stx2 A | GGAATGCAAATCAGTCGTCA (SEQ ID NO: 27) | Biotin |
| MalB | GCCGATGCCAAATCGTCAG (SEQ ID NO: 28) | Biotin |

Forward primers for this example were conjugated with biotin. Reverse primers were conjugated with peptide haptens for which antibodies were available (Research Diagnostics, Flanders N.J.). Covalent attachment of the haptens was at the 5' terminus of the oligomer. Peptides were activated at the amino terminus for coupling.

Example 3

A result of an assay in which the targets of Example 2 were extracted, amplified and detected is shown in FIG. 6.

Example 4

A respiratory panel containing biotinylated and hapten-tagged primer pairs is designed. The primers are synthesized and then deposited in separate amplification channels or chambers of a device. Following the procedure of Example 2, throat swab washings are analyzed. A mini-bead impact mill is used to prepare the sample prior to analysis. A result is displayed in the detection chamber. The product is packaged as a kit.

Example 5

A sexually transmitted disease panel containing biotinylated and peptidyl hapten-tagged primer pairs is designed and the primers are synthesized. The primers are then deposited in separate amplification channels or chambers of a device. Following the procedure of Example 2, vaginal swab washings are analyzed. A detection endpoint is displayed in the detection chamber. The product is packaged as a kit.

Example 6

An oncogene panel containing biotinylated and peptidyl hapten-tagged primer pairs is designed and the primers are synthesized. The primers are then deposited in a common amplification channel or chamber. Following PCR amplification, the amplification products are detected in a detection station. The product is packaged as a kit.

While the above description contains specificities, these specificities should not be construed as limitations on the scope of the invention, but rather as exemplifications of embodiments of the invention. That is to say, the foregoing description of the invention is exemplary for purposes of illustration and explanation. Without departing from the spirit and scope of this invention, one skilled in the art can make various changes and modifications to the invention to adapt it to various usages and conditions without inventive step. As such, these changes and modifications are properly, equitably, and intended to be within the full range of equivalence of the following claims. Thus the scope of the invention should be determined by the appended claims and their legal equivalents, rather than by the examples given.

What is claimed is:

1. An apparatus for performing a nucleic acid assay on a biological sample, said apparatus comprising:
   (a) a plastic disposable cartridge body with external surface, said body containing dry and fluid reagents for said nucleic acid assay, wherein said cartridge body comprises:
      (i) a first fluidic subcircuit for extracting a nucleic acid from said sample;
      (ii) a second fluidic subcircuit for synthesizing an amplicon product, wherein said second fluidic subcircuit is configured for receiving said nucleic acids from said first fluidic subcircuit;
      (iii) a third fluidic subcircuit for detecting said amplicon product, wherein said third fluidic subcircuit is configured for receiving said amplicon product from said second fluidic subcircuit;
      (iv) a sanitary waste collection chamber having a fluid inlet and valve with fluidic connection to said first fluidic circuit, a bibulous pad within said chamber, and a film covering said bibulous pad and separating said fluid inlet from an outside vent, said outside vent for venting said chamber through said external surface; and
      (v) a pneumatic interconnect subcircuit with control arms for pneumatically actuating said first, second and third fluidic subcircuits; and
   (b) an off-cartridge pneumatic actuation manifold configured with pneumatic interface to said cartridge body and programmed to actuate said first, second and third fluidic subcircuits according to a train of positive and negative pneumatic pressure pulses delivered to said pneumatic interconnect subcircuit under control of a microprocessor.

2. The apparatus of claim 1, wherein said first fluidic subcircuit comprises:
 (a) a sample inlet port;
 (b) a first bellows pump fluidly and valvedly interconnected by a first fluidic channel to said sample inlet port and by a second fluidic channel to a second bellows pump, wherein said second bellows pump comprises a frangible lysis buffer reagent pack for programmable admixture of lysis buffer to said sample and wherein said pneumatic interconnect subcircuit is configured for programmable rupture of said lysis buffer reagent pack by compressing said lysis buffer reagent pack between a diaphragm and an opposing sharp in said second bellows pump; and
 (c) a solid-phase nucleic acid target capture assembly for extracting a nucleic acid, wherein said target capture assembly is fluidly and valvedly interconnected to said first bellows pump and to said inlet port.

3. The apparatus of claim 2, wherein said first fluidic subcircuit further comprises:
 (a) a third bellows pump fluidly and valvedly interconnected to said target capture assembly, wherein said third bellows pump comprises a frangible wash reagent pack for programmable delivery of a wash reagent to said target capture assembly and wherein said pneumatic interconnect subcircuit is configured for programmable rupture of said wash reagent pack by compressing said wash reagent pack between a diaphragm and an opposing sharp in said third bellows pump.

4. The apparatus of claim 3, wherein said first fluidic subcircuit further comprises:
 (a) a fourth bellows pump fluidly and valvedly interconnected to said target capture assembly, wherein said fourth bellows pump comprises a frangible elution reagent pack for programmable delivery of an elution buffer to said target capture assembly and wherein said pneumatic interconnect subcircuit is configured for programmable rupture of said elution reagent pack by compressing said elution reagent pack between a diaphragm and an opposing sharp in said fourth bellows pump; and
 (b) a second fluidic channel for interconnecting said target capture assembly with said second fluidic subcircuit, whereby a nucleic acid eluate is conveyed to said second fluidic subcircuit for amplification.

5. The apparatus of claim 4, wherein said second fluidic subcircuit comprises:
 (a) a PCR fluidics and thermal interface comprising a first and second bellows pump fluidly interconnected by a microchannel, wherein said PCR fluidics and thermal interface is configured for holding said first bellows pump at a fixed temperature for denaturing said nucleic acid eluate and said second bellows pump at a fixed temperature for annealing said nucleic acid eluate, and wherein said programmable train of positive and negative pneumatic pressure pulses is configured for reciprocally pumping of said nucleic acid eluate between said first and second bellows pumps, thereby thermocycling said nucleic acid eluate;
 (b) a dehydrated PCR mix reagent with primers for reconstitution in said nucleic eluate; and
 (c) a third fluidic channel with valve for valvedly interconnecting said second fluidic circuit with said third fluidic subcircuit, whereby said amplicon product of said second fluidic circuit is conveyed to said third fluidic subcircuit for detection.

6. The apparatus of claim 5, wherein said dehydrated PCR mix reagent is directly reconstituted in said nucleic acid eluate.

7. The apparatus of claim 5, wherein said first and second bellows pumps of said PCR fluidics and thermal interface are held at said fixed temperatures by a first and a second heating blocks contacting said thermal interface, wherein said first block operatively contacts said first bellows pump and said second block operatively contacts said second bellows pump.

8. The apparatus of claim 7, further comprising a cDNA synthesis chamber fluidically interposed between said target capture assembly and said first and second bellows pumps of said PCR fluidics and thermal interface.

9. The apparatus of claim 5, wherein said second bellows pump comprises a dehydrated polymerase.

* * * * *